United States Patent
Stulen et al.

(10) Patent No.: US 10,524,815 B2
(45) Date of Patent: *Jan. 7, 2020

(54) ULTRASONIC FORCEPS

(71) Applicant: ETHICON LLC, Guaynabo, PR (US)

(72) Inventors: Foster B. Stulen, Mason, OH (US); Michael R. Lamping, Cincinanti, OH (US); Cory G. Kimball, Hamilton, OH (US); Emron J. Henry, Seattle, WA (US); Michael J. Stokes, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 255 days.

This patent is subject to a terminal disclaimer.

(21) Appl. No.: 15/602,431

(22) Filed: May 23, 2017

(65) Prior Publication Data

US 2017/0319227 A1    Nov. 9, 2017

Related U.S. Application Data

(63) Continuation of application No. 14/222,943, filed on Mar. 24, 2014, now Pat. No. 9,675,374.

(51) Int. Cl.
*A61B 17/32* (2006.01)
*A61B 17/285* (2006.01)
(Continued)

(52) U.S. Cl.
CPC .... *A61B 17/285* (2013.01); *A61B 17/320068* (2013.01); *A61B 18/14* (2013.01);
(Continued)

(58) Field of Classification Search
CPC . A61B 17/28; A61B 17/2812; A61B 17/2841; A61B 17/285; A61B 17/320068;
(Continued)

(56) References Cited

U.S. PATENT DOCUMENTS

| | | |
|---|---|---|
| 3,636,943 A | 1/1972 | Balamuth |
| 3,862,630 A | 1/1975 | Balamuth |

(Continued)

FOREIGN PATENT DOCUMENTS

| | | |
|---|---|---|
| CN | 1826084 A | 8/2006 |
| DE | 20 2006 013608 U1 | 1/2008 |

(Continued)

OTHER PUBLICATIONS

International Search Report and Written Opinion dated Aug. 4, 2015 for Application No. PCT/US2015/019891, 18 pgs.

(Continued)

*Primary Examiner* — Ryan J. Severson
(74) *Attorney, Agent, or Firm* — Frost Brown Todd LLC

(57) ABSTRACT

An ultrasonic forceps comprises a housing, an acoustic assembly, and a tine. The housing joins the acoustic assembly and the tine to the forceps and permits the tine to pivot relative to the acoustic assembly. The acoustic assembly comprises a transducer, a waveguide, and ultrasonic blade, and a waveguide sheath. The transducer is configured to generate ultrasonic vibrations directing the ultrasonic vibrations to the waveguide. The waveguide communicates the ultrasonic vibrations distally to the ultrasonic blade. The ultrasonic blade is configured to vibrate in response to the ultrasonic vibrations generated by the transducer. When the tine is pivoted relative to the transducer, the tine is configured to move toward the ultrasonic blade. Tissue may be grasped between the tine and the ultrasonic blade. The tissue may be denatured when the ultrasonic vibrations generated by the transducer vibrate the ultrasonic blade, thus resulting in the tissue being cut and/or sealed.

20 Claims, 46 Drawing Sheets

(51) Int. Cl.
*A61F 7/00* (2006.01)
*A61B 18/14* (2006.01)
*A61B 17/28* (2006.01)
*A61B 18/00* (2006.01)
*A61B 17/00* (2006.01)

(52) U.S. Cl.
CPC ............ *A61B 18/1442* (2013.01); *A61F 7/00* (2013.01); *A61B 2017/0046* (2013.01); *A61B 2017/00473* (2013.01); *A61B 2017/2825* (2013.01); *A61B 2017/320069* (2017.08); *A61B 2017/320071* (2017.08); *A61B 2017/320089* (2017.08); *A61B 2017/320094* (2017.08); *A61B 2017/320095* (2017.08); *A61B 2018/0019* (2013.01); *A61B 2018/00172* (2013.01); *A61B 2018/00178* (2013.01); *A61B 2018/00202* (2013.01); *A61B 2018/00339* (2013.01); *A61B 2018/00434* (2013.01); *A61B 2018/00601* (2013.01); *A61B 2018/00607* (2013.01); *A61B 2018/00952* (2013.01); *A61B 2018/00994* (2013.01); *A61B 2018/1405* (2013.01); *A61B 2018/1457* (2013.01); *A61B 2018/1462* (2013.01); *A61F 2007/0054* (2013.01)

(58) Field of Classification Search
CPC ........ A61B 17/320092; A61B 18/1442; A61B 18/1445; A61B 18/1447; A61B 2017/0046; A61B 2017/00738; A61B 2017/2808; A61B 2017/2845; A61B 2017/320072; A61B 2017/320076; A61B 2017/320088; A61B 2017/320096; A61B 2018/0019; A61B 2018/00601; A61B 2018/00607; A61B 2018/145; A61B 2018/1452; A61B 2018/1462
See application file for complete search history.

(56) References Cited

U.S. PATENT DOCUMENTS

| | | | |
|---|---|---|---|
| 4,041,952 A | 8/1977 | Morrison, Jr. et al. | |
| 5,269,782 A | 12/1993 | Sutter | |
| 5,322,055 A * | 6/1994 | Davison | A61B 17/320068 601/2 |
| 5,810,805 A | 9/1998 | Sutcu et al. | |
| 5,873,873 A * | 2/1999 | Smith | A61B 17/320092 606/1 |
| 5,902,301 A | 5/1999 | Olig | |
| 5,980,510 A * | 11/1999 | Tsonton | A61B 17/320092 604/22 |
| 6,004,335 A | 12/1999 | Vaitekunas et al. | |
| 6,110,171 A | 8/2000 | Rydell | |
| 6,139,561 A | 10/2000 | Shibata et al. | |
| 6,193,709 B1 * | 2/2001 | Miyawaki | A61B 17/320092 601/2 |
| 6,210,411 B1 | 4/2001 | Hofmann et al. | |
| 6,267,761 B1 | 7/2001 | Ryan | |
| 6,325,811 B1 | 12/2001 | Messerly | |
| 6,425,907 B1 | 7/2002 | Shibata et al. | |
| 6,436,114 B1 | 8/2002 | Novak et al. | |
| 6,773,444 B2 | 8/2004 | Messerly | |
| 6,783,524 B2 * | 8/2004 | Anderson | A61B 17/320068 606/1 |
| 6,800,077 B1 | 10/2004 | Mucko et al. | |
| 6,860,882 B2 * | 3/2005 | Battles | A61B 18/1442 606/51 |
| 6,869,439 B2 | 3/2005 | White et al. | |
| 7,211,079 B2 | 5/2007 | Treat | |
| 7,223,267 B2 | 5/2007 | Isola et al. | |
| 7,235,073 B2 | 6/2007 | Levine et al. | |
| 7,285,895 B2 | 10/2007 | Beaupre | |
| 7,563,269 B2 | 7/2009 | Hashiguchi | |
| 7,854,735 B2 | 12/2010 | Houser et al. | |
| 7,914,529 B2 | 3/2011 | Bilski et al. | |
| 8,100,894 B2 | 1/2012 | Mucko et al. | |
| 8,328,834 B2 | 12/2012 | Isaacs et al. | |
| 8,430,898 B2 * | 4/2013 | Wiener | A61B 17/2202 606/169 |
| 8,461,744 B2 | 6/2013 | Wiener et al. | |
| 8,591,536 B2 | 11/2013 | Robertson | |
| 8,623,027 B2 | 1/2014 | Price et al. | |
| 8,652,132 B2 | 2/2014 | Tsuchiya et al. | |
| D707,816 S | 6/2014 | LaMontagne et al. | |
| D707,817 S | 6/2014 | Schallert | |
| D724,732 S | 3/2015 | Kimball et al. | |
| 8,986,302 B2 | 3/2015 | Aldridge et al. | |
| 9,023,071 B2 | 4/2015 | Miller et al. | |
| 9,023,044 B2 | 5/2015 | Emmerich | |
| 9,044,242 B2 | 6/2015 | Scheller et al. | |
| 9,095,367 B2 | 7/2015 | Olson et al. | |
| 9,381,058 B2 | 7/2016 | Houser et al. | |
| 9,393,037 B2 | 7/2016 | Olson et al. | |
| 9,662,513 B2 | 5/2017 | Sanai et al. | |
| 9,675,374 B2 * | 6/2017 | Stulen | A61B 17/320068 |
| 9,743,946 B2 | 8/2017 | Faller et al. | |
| 9,901,358 B2 | 2/2018 | Faller et al. | |
| 9,901,360 B2 | 2/2018 | Neurohr et al. | |
| 2003/0212422 A1 | 11/2003 | Fenton et al. | |
| 2004/0064151 A1 | 4/2004 | Mollenauer | |
| 2004/0215132 A1 | 10/2004 | Yoon | |
| 2005/0143769 A1 | 6/2005 | White et al. | |
| 2006/0079874 A1 | 4/2006 | Faller et al. | |
| 2007/0191713 A1 * | 8/2007 | Eichmann | A61B 17/1606 600/471 |
| 2007/0282333 A1 | 12/2007 | Fortson et al. | |
| 2008/0200940 A1 | 8/2008 | Eichmann et al. | |
| 2010/0094323 A1 | 4/2010 | Isaacs et al. | |
| 2010/0331873 A1 | 12/2010 | Dannaher et al. | |
| 2012/0078249 A1 | 3/2012 | Eichmann et al. | |
| 2012/0116265 A1 | 5/2012 | Houser et al. | |
| 2013/0345732 A1 | 12/2013 | Dannaher et al. | |
| 2014/0207163 A1 | 7/2014 | Eichmann et al. | |
| 2015/0080924 A1 | 3/2015 | Stulen et al. | |
| 2015/0080925 A1 | 3/2015 | Schulte et al. | |
| 2015/0141981 A1 | 5/2015 | Price et al. | |
| 2015/0148833 A1 | 5/2015 | Stokes et al. | |
| 2015/0148835 A1 | 5/2015 | Faller et al. | |
| 2016/0074060 A1 | 3/2016 | Messerly et al. | |
| 2017/0319227 A1 * | 11/2017 | Stulen | A61B 17/320068 |

FOREIGN PATENT DOCUMENTS

| | | |
|---|---|---|
| JP | H03-280945 A | 12/1991 |
| JP | 2000-254135 A | 9/2000 |
| JP | 2001-057985 A | 3/2001 |
| JP | 2001-104326 A | 4/2001 |
| JP | 2002-065689 A | 3/2002 |
| JP | 3 686765 B2 | 8/2005 |
| WO | WO 87/01276 A1 | 3/1987 |
| WO | WO 2012/149361 A1 | 11/2012 |

OTHER PUBLICATIONS

U.S. Appl. No. 61/410,603, filed Nov. 5, 2010.
Chinese Office Action, The First Office Action, and First Search Report dated Aug. 2, 2018 for Application No. CN 201580026880.2, 10 pgs.
Japanese Office Action, Notice of Reasons for Refusal, dated Dec. 25, 2018 for Application No. JP 2016-558582, 23 pgs.
Japanese Office Action, Decision to Grant a Patent, dated May 14, 2019 for Application No. JP 2016-558582, 5 pgs.

* cited by examiner

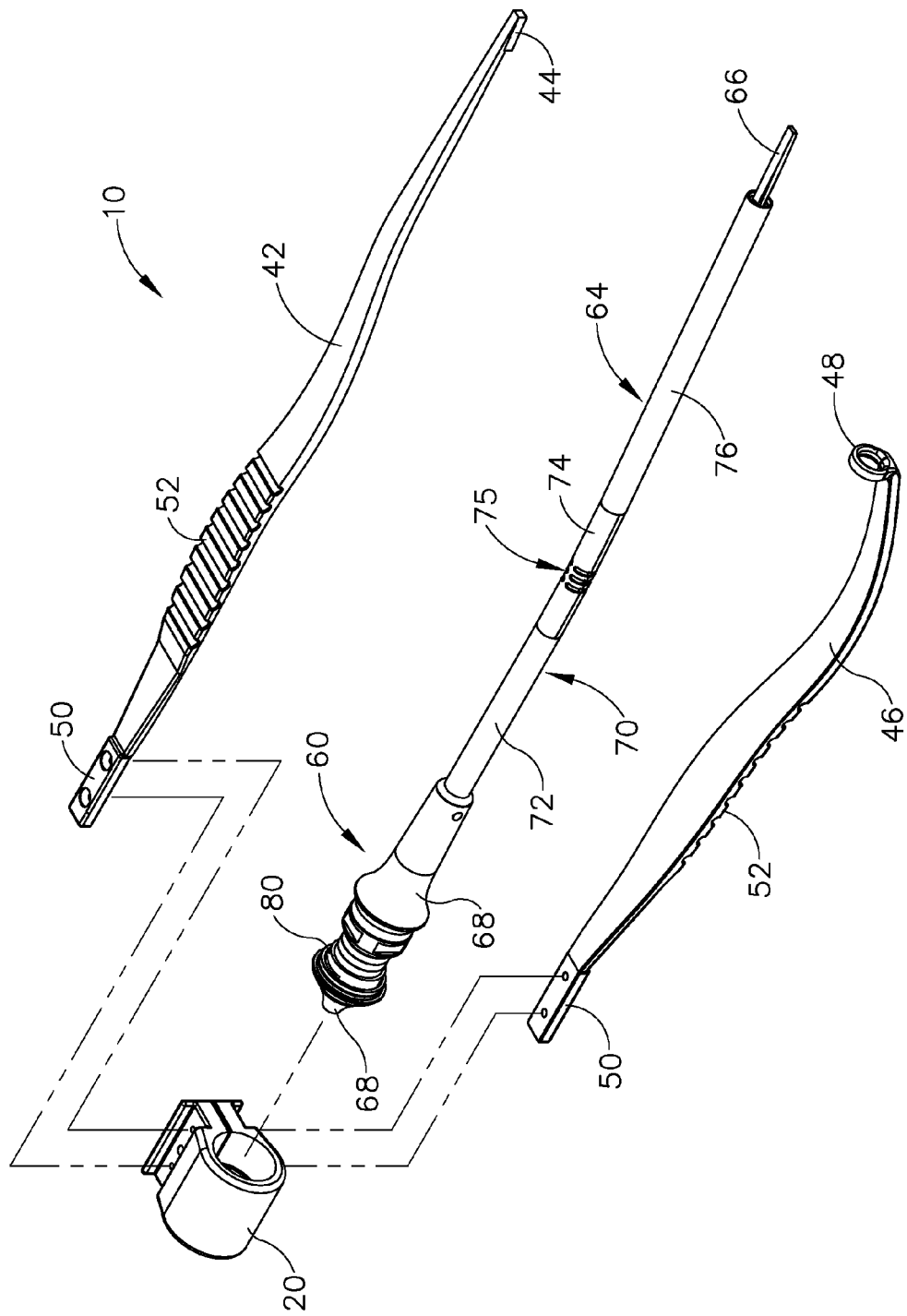

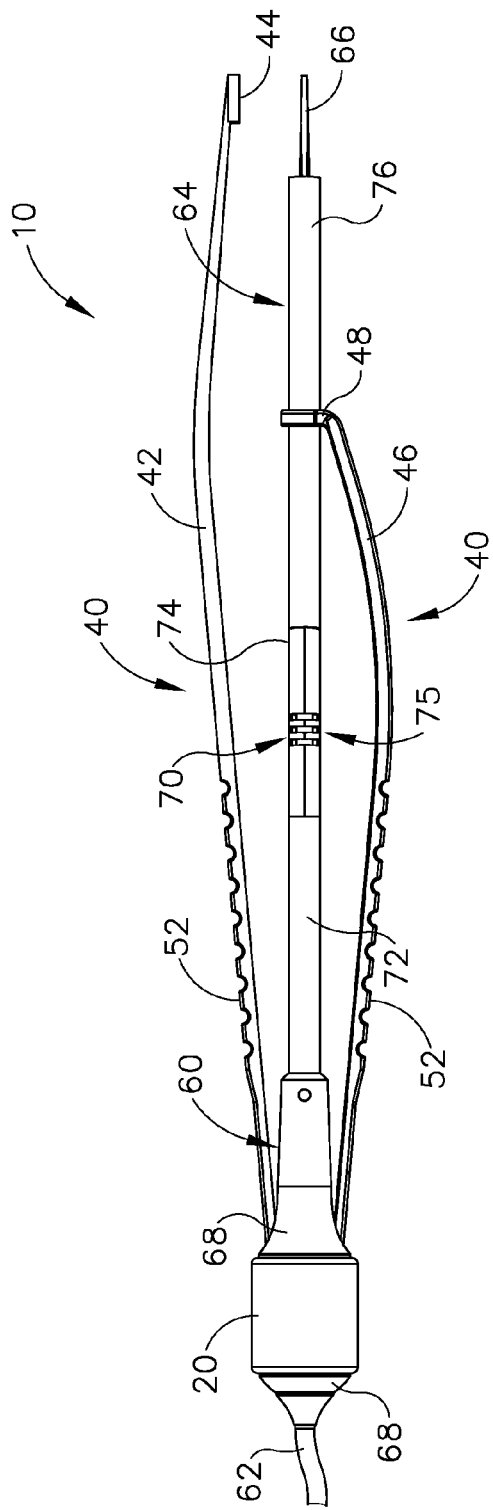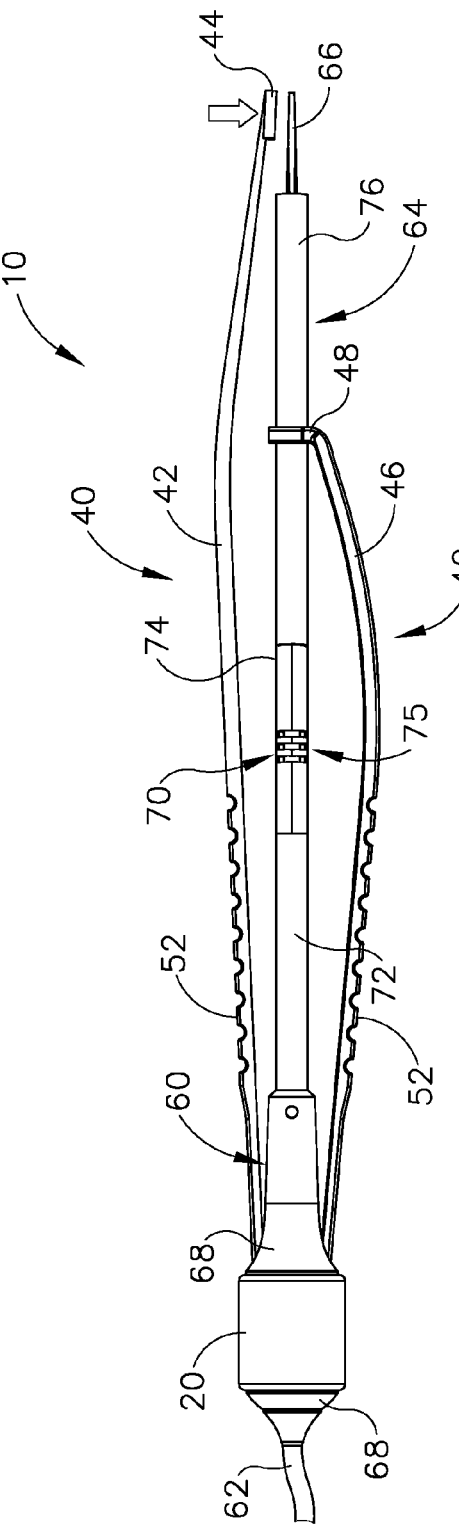
Fig. 3A
Fig. 3B

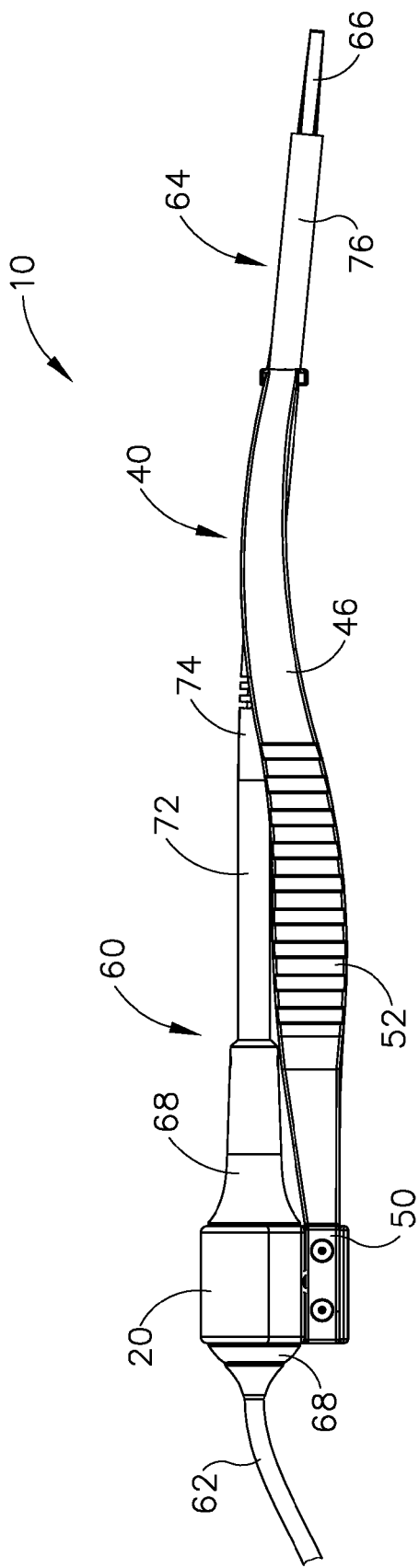
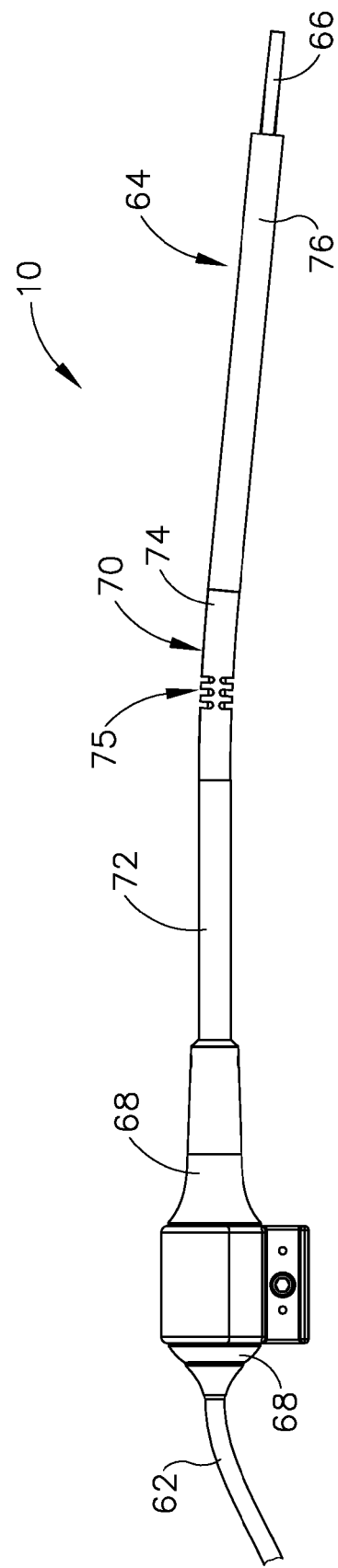
Fig. 4
Fig. 5

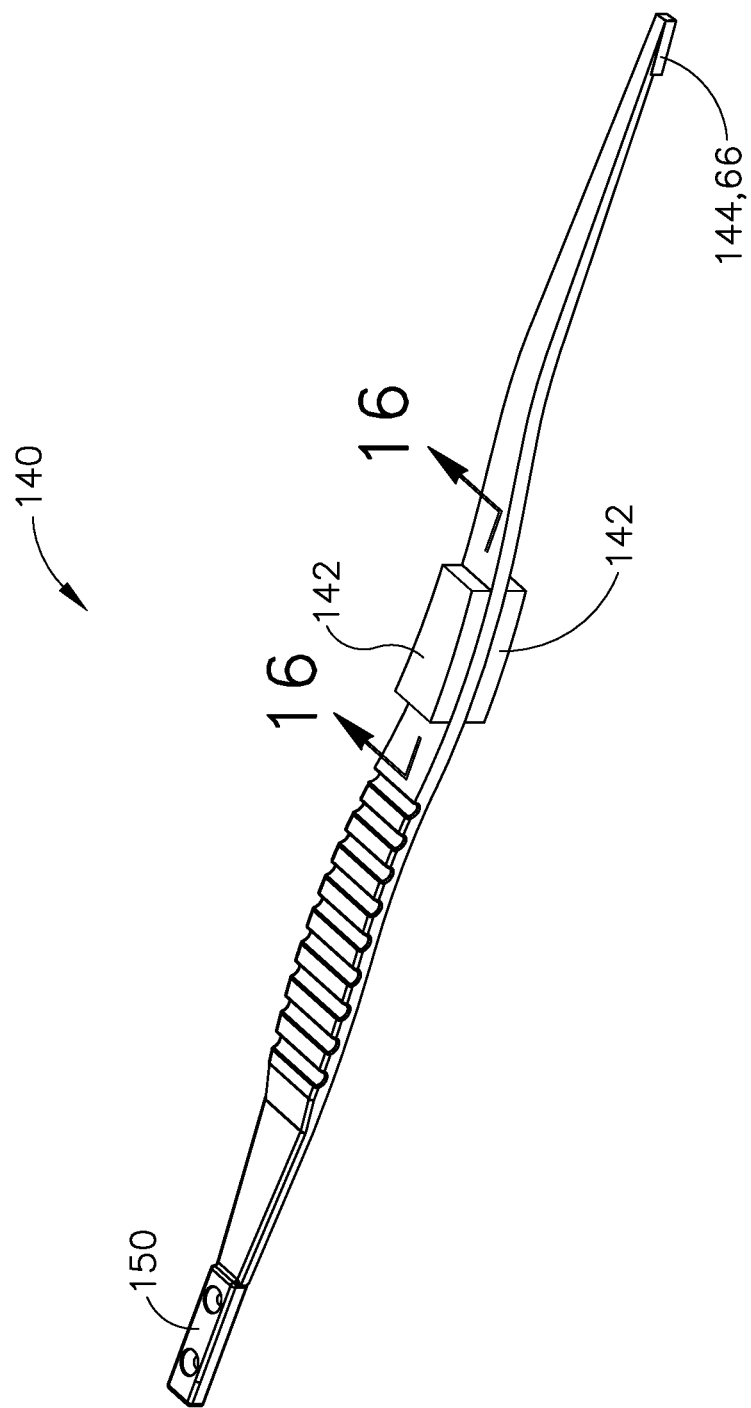

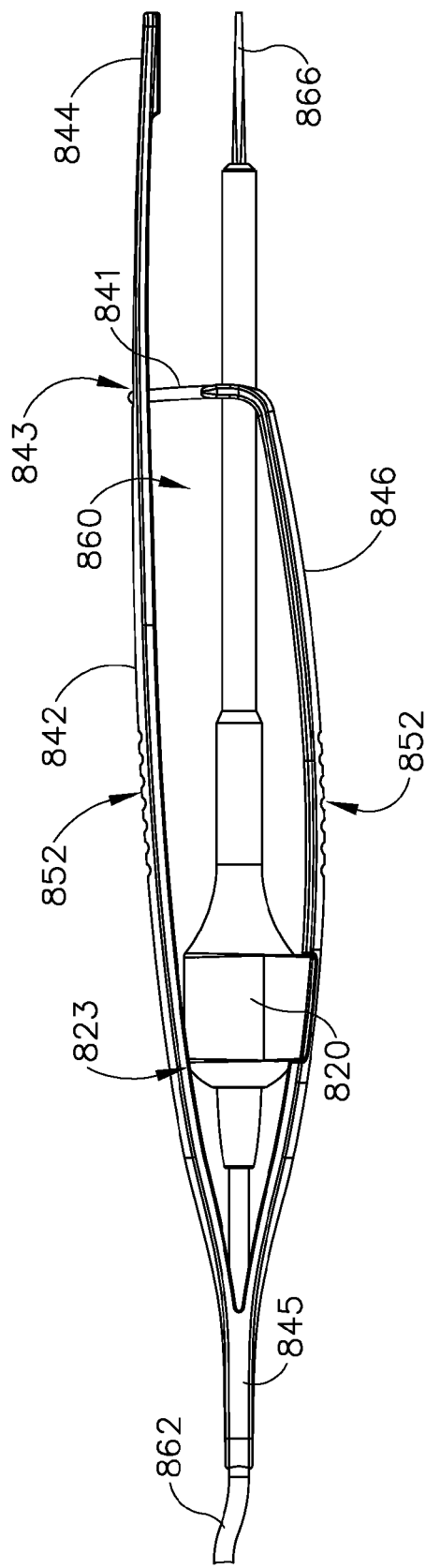
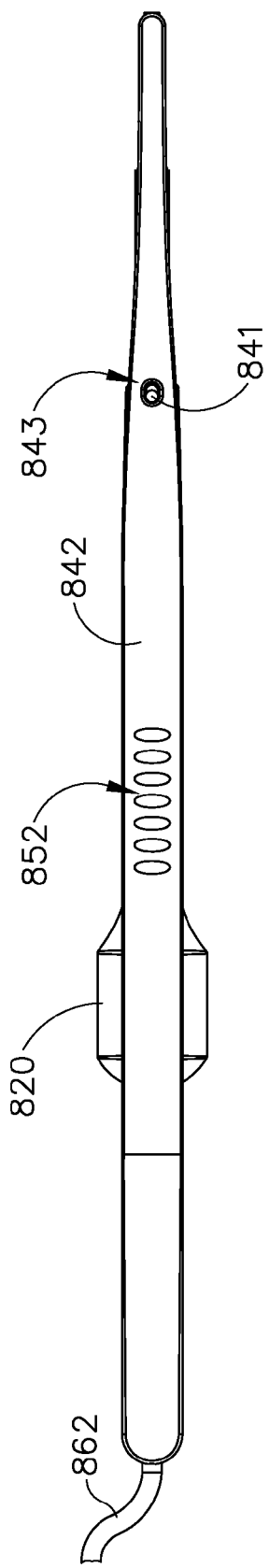
Fig. 32
Fig. 33

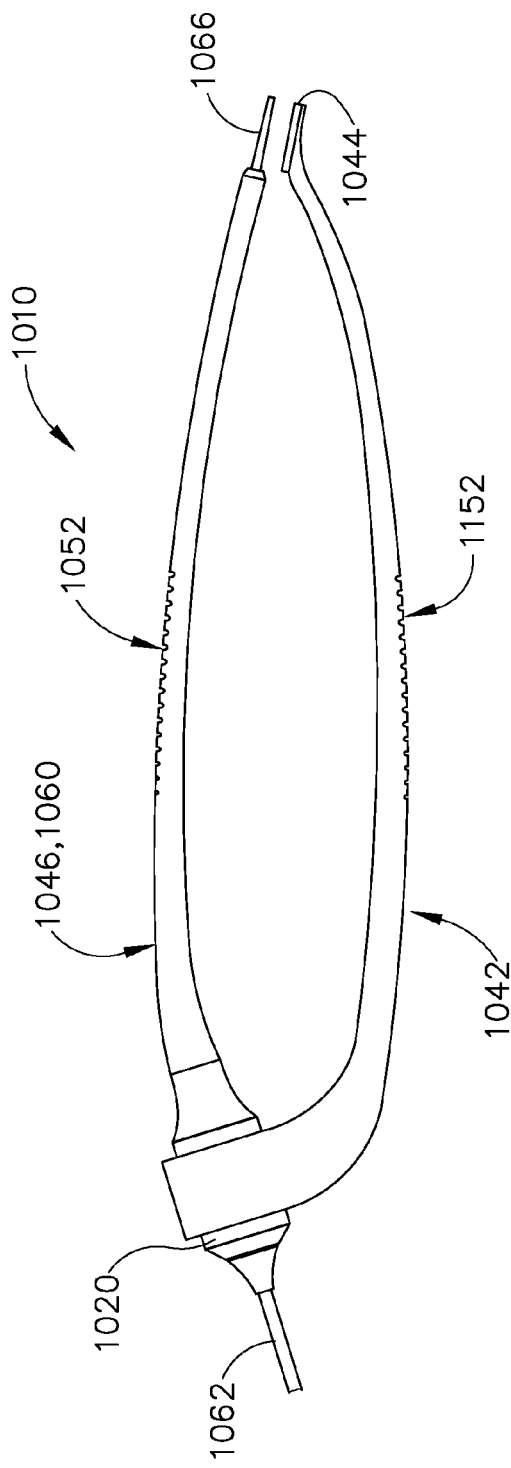
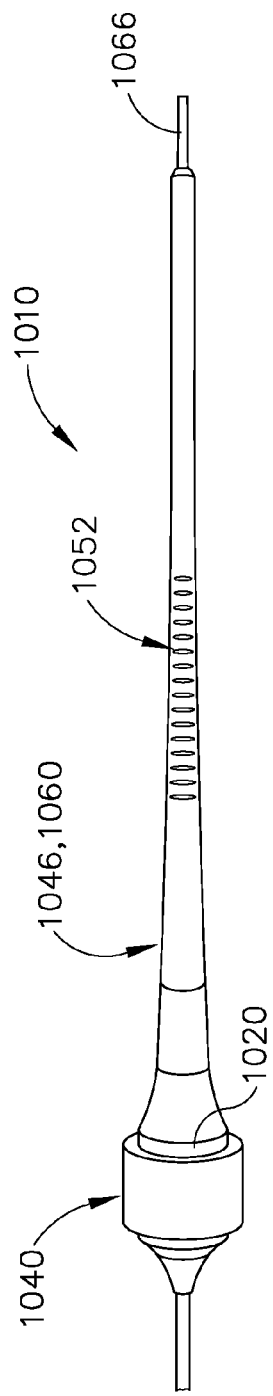
Fig.38
Fig.39

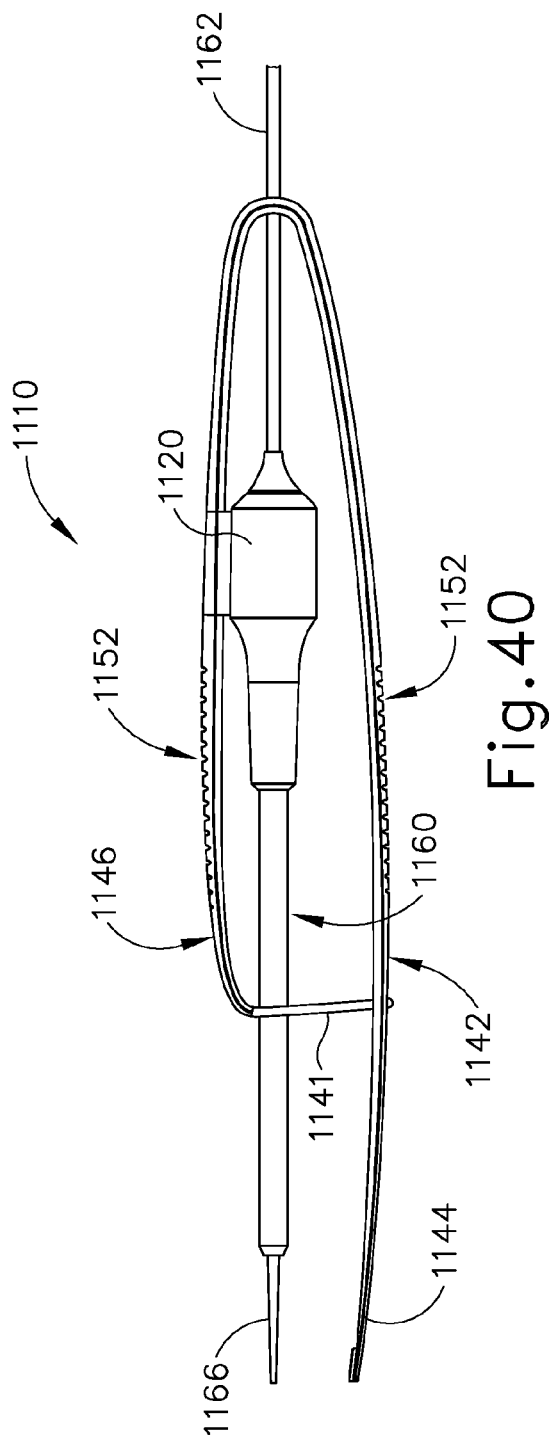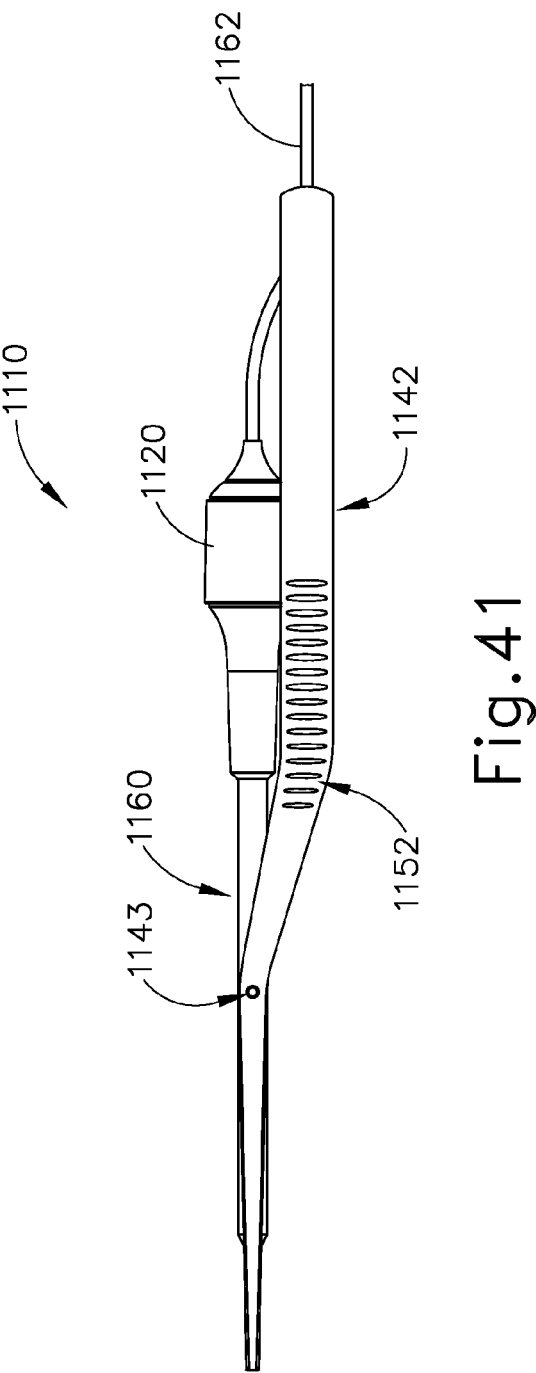

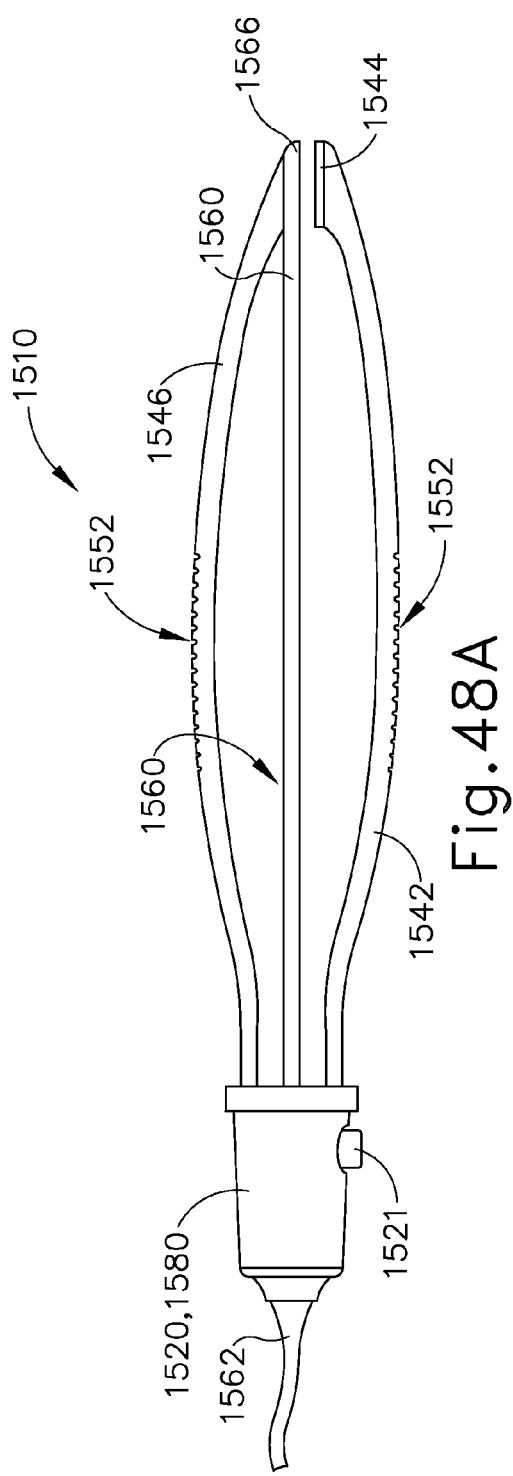
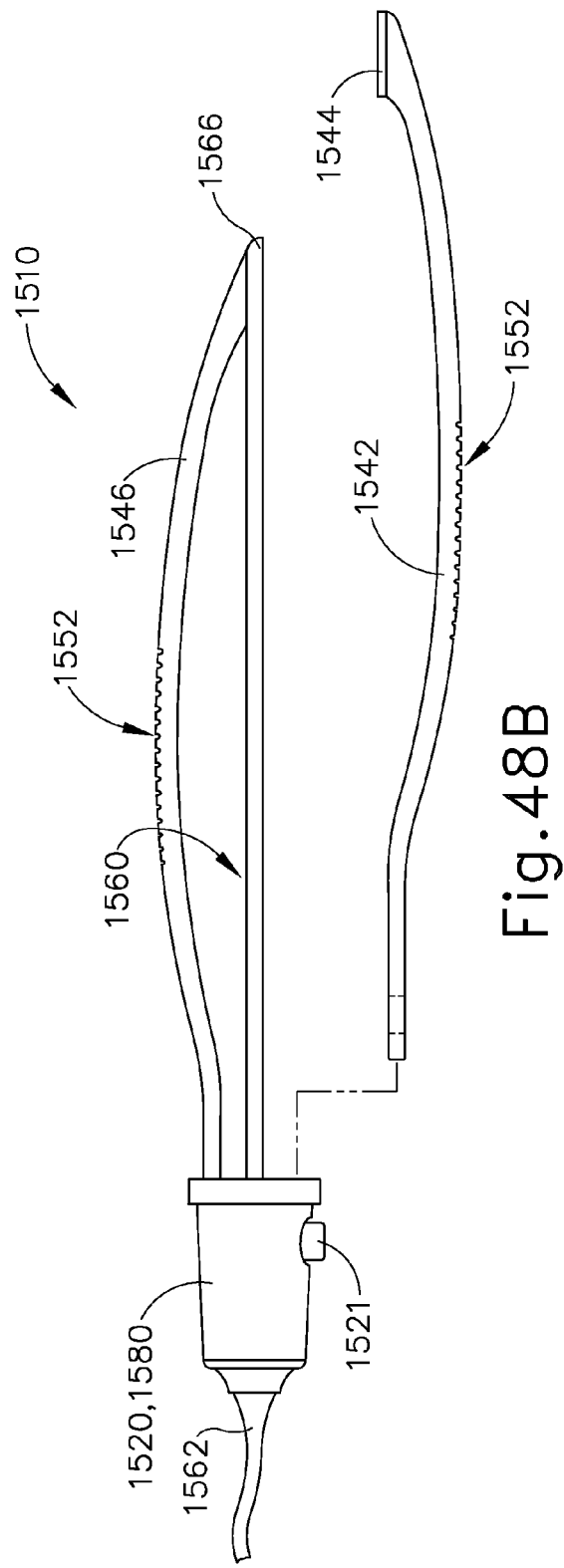
Fig. 48A
Fig. 48B

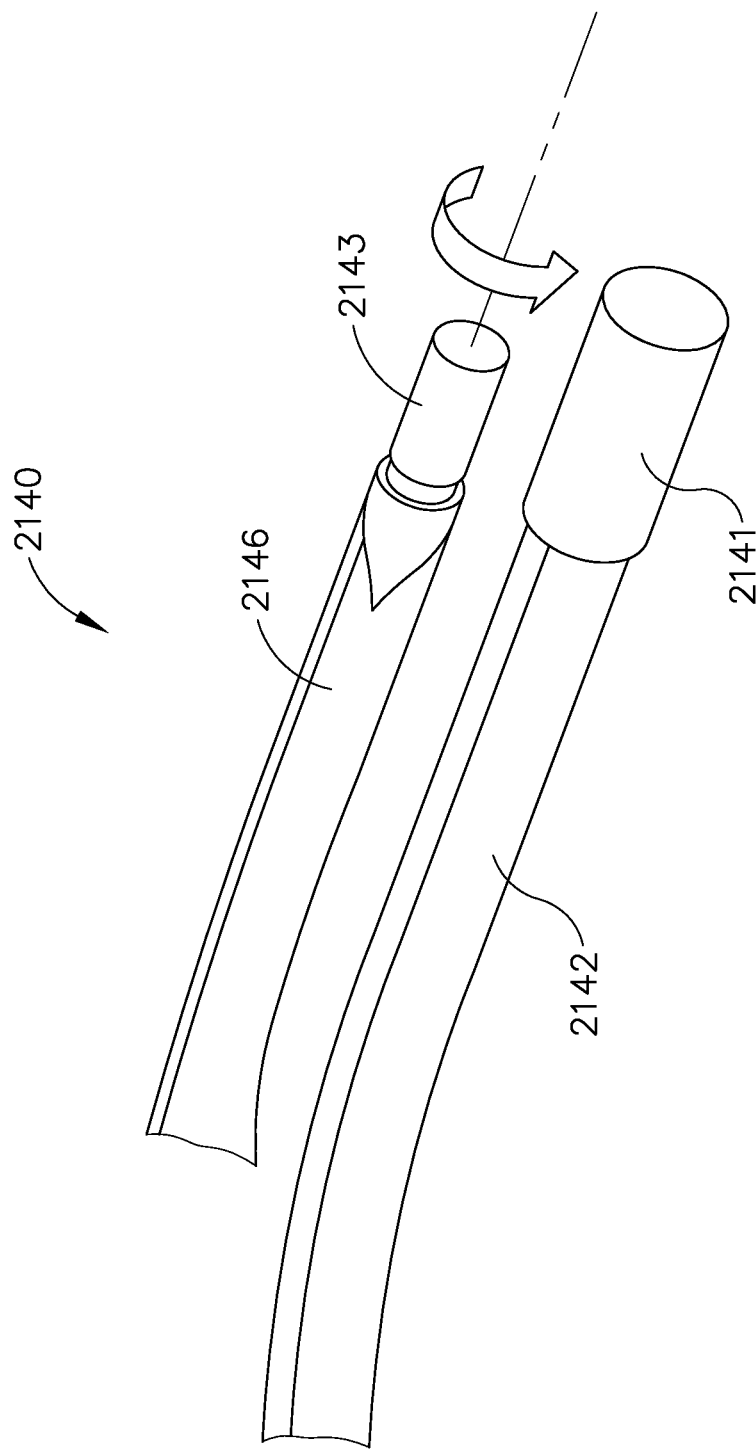

ULTRASONIC FORCEPS

This application is a Continuation of prior U.S. application Ser. No. 14/222,943, entitled "Ultrasonic Forceps," filed Mar. 24, 2014, issued as U.S. Pat. No. 9,675,374 on Jun. 13, 2017.

BACKGROUND

A variety of surgical instruments such as shears incorporate the use of ultrasonic elements to vibrate at ultrasonic frequencies to cut and/or seal tissue (e.g., by denaturing proteins in tissue cells). These surgical instruments include piezoelectric elements that convert electrical power into ultrasonic vibrations, which are communicated along an acoustic waveguide to a blade element. The precision of cutting and coagulation may be controlled by the surgeon's technique and adjusting the power level, blade edge, tissue traction and blade pressure. A variety of forceps instruments incorporate the use of radio frequency (RF) energy to cut and/or seal tissue. Such forceps may be used in surgical procedures requiring fine or precise surgical techniques. In particular, two tines of a forceps instrument may be used to precisely grasp tissue. RF energy (e.g., electrical current applied at a frequency within radio frequency ranges) may then be applied to a single tine (mono-polar) or both tines (bi-polar) to cut and/or seal tissue. Examples of forceps instruments that incorporate an ultrasonically vibrating feature are disclosed in U.S. Pub. No. 2009/0036912, entitled "Ultrasonic Surgical Instruments," published Feb. 5, 2009, issued as U.S. Pat. No. 8,430,898 on Apr. 13, 2013, the disclosure of which is incorporated by reference herein.

Other examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati. Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Dec. 18, 2013, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on Apr. 15, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on May 22, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 6, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, now expired, entitled "Energy-Based Surgical Instruments," the disclosure of which is incorporated by reference herein.

Additionally, examples of RF forceps are disclosed in U.S. Pat. No. 6,860,882, entitled "Electro-Surgical Bipolar Forceps." issued Mar. 1, 2005, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 2 depicts a partially exploded view of the ultrasonic forceps of FIG. 1;

FIG. 3A depicts a top plan view of the ultrasonic forceps of FIG. 1;

FIG. 3B depicts a top plan view of the ultrasonic forceps of FIG. 1, with a tine depressed;

FIG. 4 depicts a side elevational view of the ultrasonic forceps of FIG. 1;

FIG. 5 depicts a side elevational view of the ultrasonic forceps of FIG. 1, with the tines removed:

FIG. 15 depicts a perspective view of an exemplary alternative tine that may be incorporated into the ultrasonic forceps of FIG. 1;

FIG. 32 depicts a side elevational view of the ultrasonic forceps of FIG. 31;

FIG. 33 depicts a top plan view of the ultrasonic forceps of FIG. 31;

FIG. 38 depicts a side elevational view of an exemplary alternative ultrasonic forceps;

FIG. 39 depicts a top plan view of the ultrasonic forceps of FIG. 38;

FIG. 40 depicts a side elevational view of an exemplary alternative ultrasonic forceps;

FIG. 41 depicts a top plan view of the ultrasonic forceps of FIG. 40;

FIG. 48A depicts a side elevational view of an exemplary alternative ultrasonic forceps having a symmetrical grip;

FIG. 48B depicts a partially exploded view of the ultrasonic forceps of FIG. 48A;

FIG. 55 depicts a perspective view of exemplary alternative tines having a rotational active tine.

Figure 1:
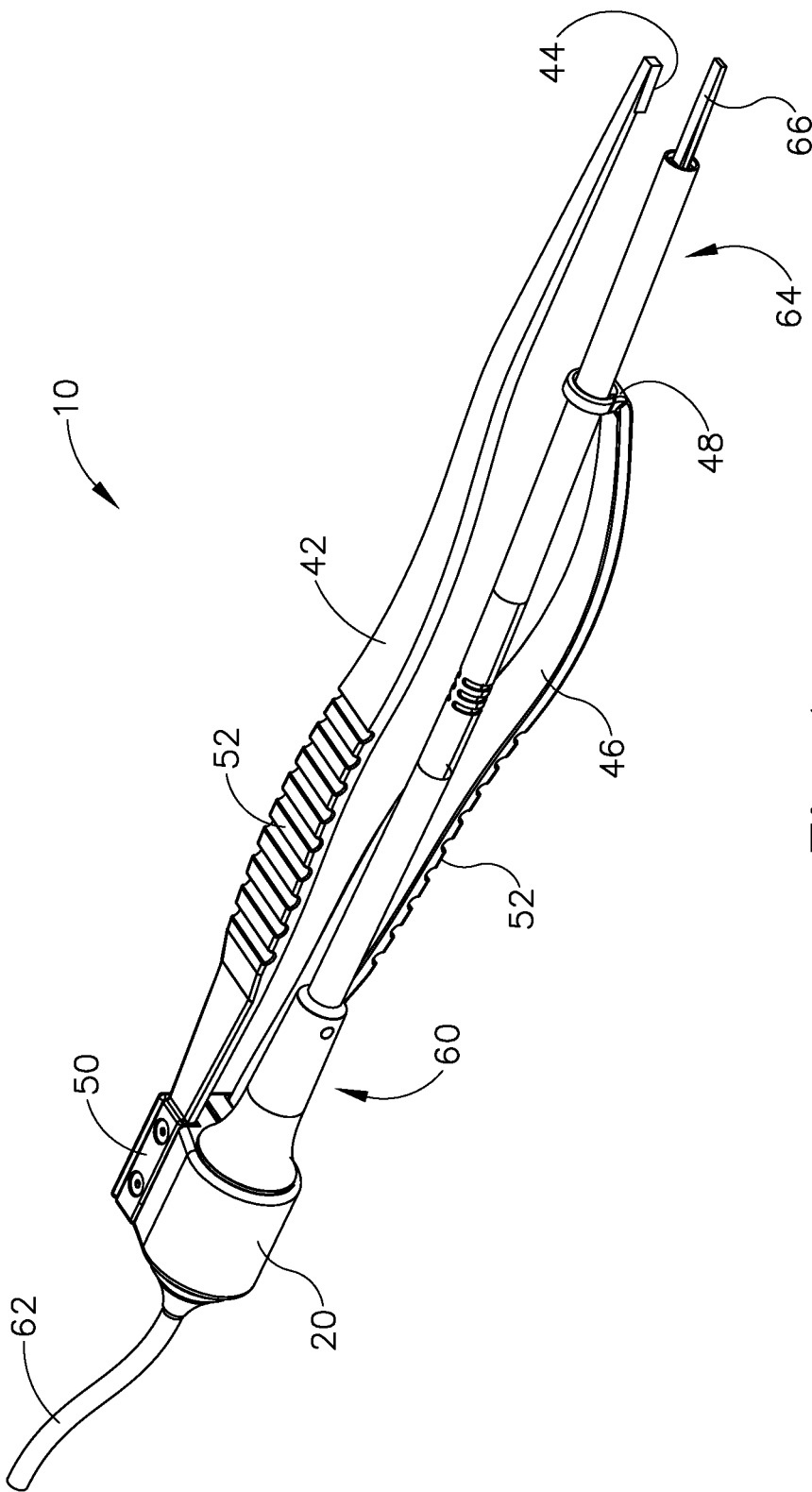
FIG. 1 depicts a perspective view of exemplary ultrasonic forceps.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Forceps

FIGS. 1-14 illustrate an exemplary ultrasonic forceps (10). At least a part of forceps (10) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, issued as U.S. Pat. No. 8,623,027 on Dec. 18, 2013; U.S. Pub. No. 2010/0069940, issued as U.S. Pat. No. 9,023,071 on Apr. 15, 2015; U.S. Pub. No. 2011/0015660, issued as U.S. Pat. No. 8,461,744 on May 22, 2013; U.S. Pub. No. 2012/0112687, issued as U.S. Pat. No. 9,381,058 on Jul. 5, 2016; U.S. Pub. No. 2012/0116265, now abandoned; U.S. patent application Ser. No. 13/538,588, issued as U.S. Pat. No. 9,393,037 on Jul. 19, 2016; U.S. patent application Ser. No. 13/657,553, issued as U.S. Pat. No. 9,095,367 on Jul. 15, 2015; U.S. Pat. App. No. 61/410,603, now expired; and/or U.S. patent application Ser. No. 14/028,717, published as U.S. Publication No. 2015/0080924 on Mar. 19, 2015, issued as U.S. Pat. No. 10,172,636 on Jan. 8, 2019. The disclosures of each of the foregoing patents, publications, and applications are incorporated by reference herein. As described therein and as will be described in greater detail below, forceps (10) is operable to cut tissue and seal or weld tissue (e.g., a blood vessel, etc.) substantially simultaneously. It should also be understood that forceps (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, forceps (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to forceps (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

FIG. 1 shows a perspective view of forceps (10) that is configured to be used in high precision surgical procedures (e.g., neurosurgery, spinal surgery, plastic surgery, etc.). Forceps (10) comprises a housing (20), a pair of tines (42, 46), an acoustic assembly (60) and a cable (62). As can best be seen in FIG. 2, housing (20) connects tines (42, 46) and acoustic assembly (60) to forceps (10). In the present example, tines (42, 46) comprise a passive tine (42) and an active tine (46). The terms "active" and "passive" are meant to differentiate between tines (42, 46) on the basis of whether they are configured to provide some form of energy to tissue, as will be discussed in more detail below. Passive tine (42) extends distally from housing with a slight curve as it extends from its proximal end to its distal end. The distal end of passive tine (42) is configured with a foot (44). As will be described in greater detail below, foot (44) has a geometry configured to cooperate with the end of a waveguide assembly (64) of acoustic assembly (60). Additionally, foot (44) may comprise a PTFE/Teflon tissue contacting pad, as will be described in greater detail below. In some versions, a PTFE/Teflon tissue contacting pad is joined with foot (44) through a mating dovetail configuration. As another merely illustrative example, a PTFE/Teflon tissue contacting pad may be configured and/or joined with foot (44) in accordance with at least some of the teachings of U.S. Pub. No. 2006/0079874, now abandoned, the disclosure of which is incorporated by reference herein. Other suitable ways in which a tissue contacting pad may be configured and/or joined with foot (44) will be apparent to those of ordinary skill in the art in view of the teachings herein. It should also be understood that any of the other passive tines disclosed herein may include a tissue contacting pad.

Active tine (46) similarly extends distally from housing (20) having a curvature corresponding to that of passive tine (42). Unlike passive tine (42), active tine (46) is configured with a waveguide receiving end (48). Waveguide receiving end (48) is configured to receive a portion of waveguide assembly (64) of acoustic assembly (60), as will be described in greater detail below. Each tine (42, 46) has an attachment member (50) on their respective proximal end configured to attach each tine (42, 46) to housing (20). Active and passive tines (42, 46) may attach to housing (20)

by any suitable means such as screws, mechanical fasteners, adhesives, or the like. In other examples methods of attachment may be omitted entirely and each tine (42, 46) may be of integral construction with housing (20).

Each tine (42, 46) may be configured with a curvature to provide an ergonomic grip for the user. It should be understood that in other examples, the curvature of each tine (42, 46) may be increased, reduced, or eliminated all together. Each tine (42, 46) is also shown as having gripping portions (52) consisting of a plurality of transverse grooves in the surface of each tine (42, 46). Gripping portions (52) may likewise be provided for an ergonomic grip for a user. Of course, gripping portions (52) may take on any suitable configuration, or may be omitted entirely. As also shown, housing (20) is located proximal to gripping portions (52) in this example. This positioning of housing (20) may provide a desirable balancing of forceps (10) in the operator's hand. This positioning of housing (20) may also facilitate routing of cable (62) away from the operator's hand, further enhancing the ergonomics of forceps (10).

As shown in FIG. 2, acoustic assembly (60) comprises a transducer (80), waveguide assembly (64), an ultrasonic blade (66) and transducer housing members (68). Acoustic assembly (60) connects to cable (62) on its proximal end. Cable (62) couples acoustic assembly (60) to a generator (not shown). The generator, may be configured to provide a power profile to acoustic assembly (60) that is particularly suited for the generation of ultrasonic vibrations through transducer (80), as will be described in greater detail below.

Acoustic assembly (60) is secured in place relative to tines (42, 46) by housing (20). Additionally, housing (20) houses a portion of transducer (80), preventing rotational and longitudinal movement of transducer (80) relative to housing (20). Waveguide assembly (60) extends distally from transducer (80). Ultrasonic blade (66) protrudes distally from waveguide assembly (60). As will be described in greater detail below, ultrasonic blade (66) is operable to cut through or seal tissue by means of ultrasonic energy communicated from transducer (80) through waveguide assembly (64) to ultrasonic blade (66). Transducer housing members (68) are configured to house the junction between cable (62) and acoustic assembly (60), and the junction between transducer (80) to waveguide assembly (64).

FIGS. 3A-B show the relationship between acoustic assembly (60) and tines (42, 46). In particular, the curvatures of passive and active tines (42, 46) may provide an ergonomic grip for a user, while acoustic assembly (60) extends along a relatively straight and central axis through a first dimension. As can be seen, active tine (46) does not contact passive tine (42). Instead, waveguide assembly (64) extends from waveguide receiving end (48) of active tine (46) to a point corresponding in length to passive tine (42). Passive tine (42) is resiliently biased to a position offset from ultrasonic blade (66), as can be seen in FIG. 3A. As shown in FIG. 3B, passive tine (42) may be deformed by a user to be in close proximity with ultrasonic blade (66), or to incidentally contact ultrasonic blade (66). Accordingly, passive tine (42), active tine (46) and acoustic assembly (60) may be collectively used to grasp tissue of a patient between passive tine (42) and ultrasonic blade (66) of acoustic assembly (60).

FIGS. 4 and 5 show a side view of forceps (10), further illustrating the relationship between acoustic assembly (60) and tines (42, 46). As can be seen, waveguide assembly (64) of acoustic assembly (60) has a bend along a second dimension as it extends distally relative to housing (20). The bend of waveguide assembly (64) corresponds to a bend in tines (42, 46). Such a configuration may be suitable to provide a user with ergonomic grip while limiting obstruction of view by forceps (10). Although a relatively gradual bend is shown in waveguide assembly (64), it should be understood that in other examples the bend may be more or less gradual, or may be omitted all together. Still in other examples, more than a single bend of waveguide assembly (64) may be incorporated into forceps (10). Other examples having different configurations of bend angles or number of bends will be apparent to those of ordinary skill in the art in view of the teachings herein.

A. Exemplary C-Clamp Housing

Figure 6:
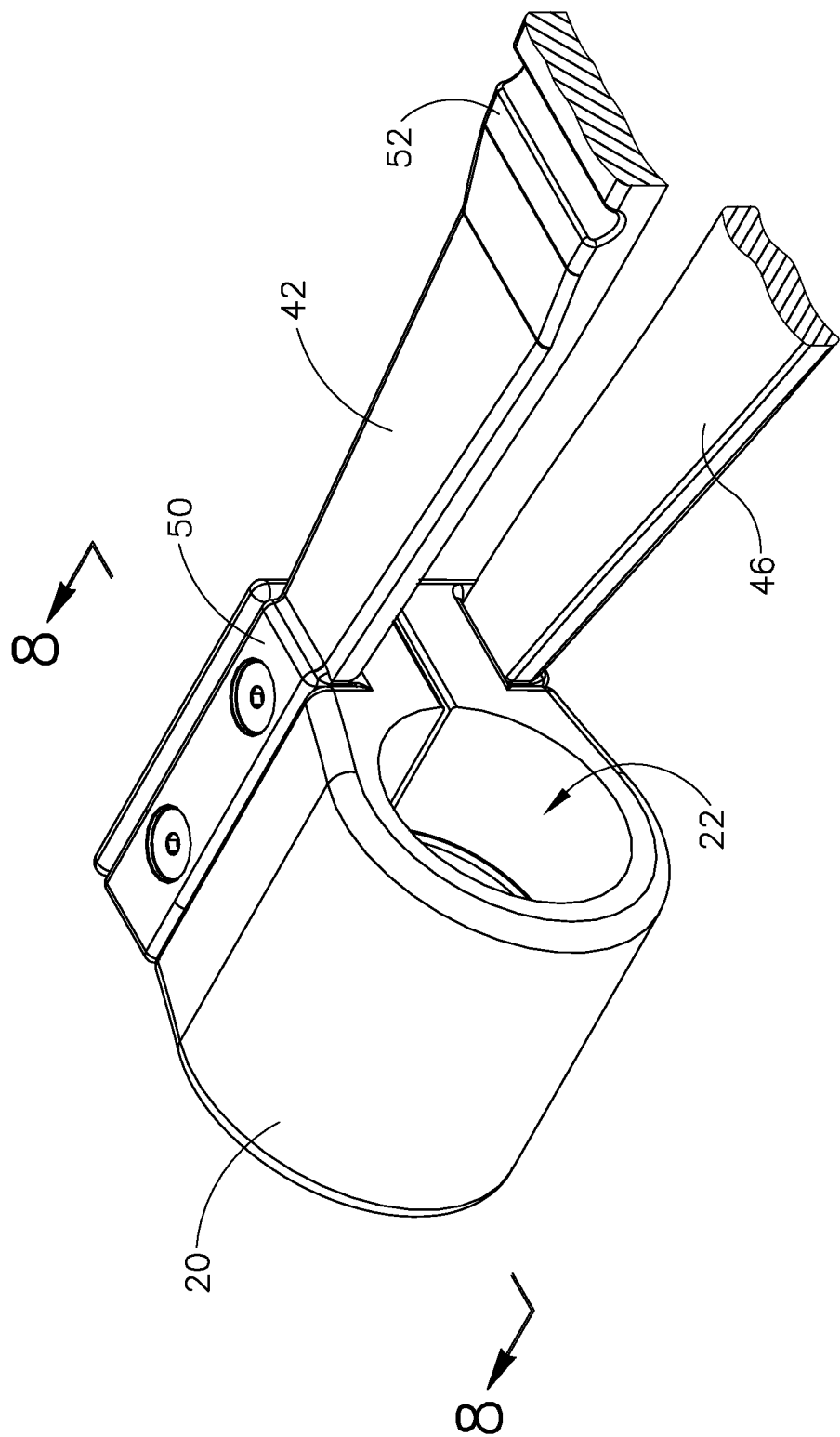
FIG. 6 depicts a detailed perspective view of a housing of the ultrasonic forceps of FIG. 1, with an acoustic assembly removed.
Figure 7:
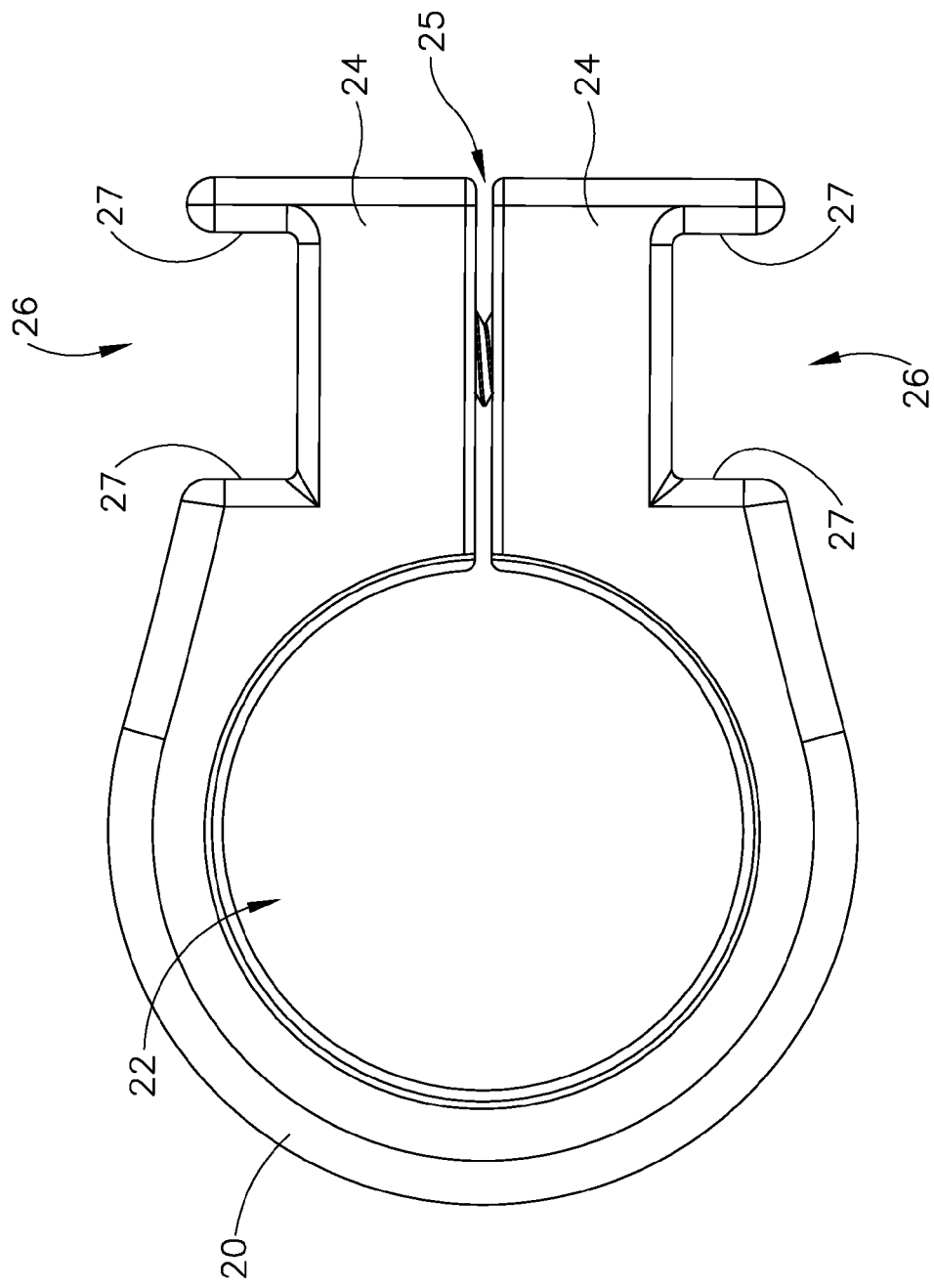
FIG. 7 depicts an end view of the housing of FIG. 6.

FIG. 6 shows a detailed perspective view of housing (20) with acoustic assembly (60) removed. Housing (20) comprises an acoustic assembly receiving bore (22) and two clamping portions (24). As can be seen in FIG. 7, acoustic assembly receiving bore (22) has a circular shape which corresponds to transducer (80) of acoustic assembly (60). The interior of acoustic assembly receiving bore (22) may be configured with any geometry suitable to fixedly secure transducer (80) within acoustic assembly receiving bore (22). For instance, acoustic assembly receiving bore (22) may comprise a series of grooves, recesses, or the like corresponding to the exterior geometry of transducer (80). Such external geometry of transducer (80) will be described in greater detail below.

Each clamping portion (24) has a groove (26) configured to receive attachment members (50) of each tine (42, 46). Grooves (26) generally correspond to attachment members (50) of each tine (42, 46). Each groove (26) defines two sidewalls (27). Sidewalls (27) ensure proper alignment of tines (42, 46) relative to acoustic assembly (60). As described above, tines (42, 46) are configured to attach to housing (20) by means of a screw fastening means. In other examples, different means of fastening tines (42, 46) to housing (20) may be used. It should be understood that such a different fastening means may necessitate a different attachment member (50) geometry leading to a grooves (26) of different sizes, shapes, or configurations. Differing configurations of attachment members (50) and grooves (26) will be apparent to those of ordinary skill in the art in view of the teachings herein.

Figure 8:
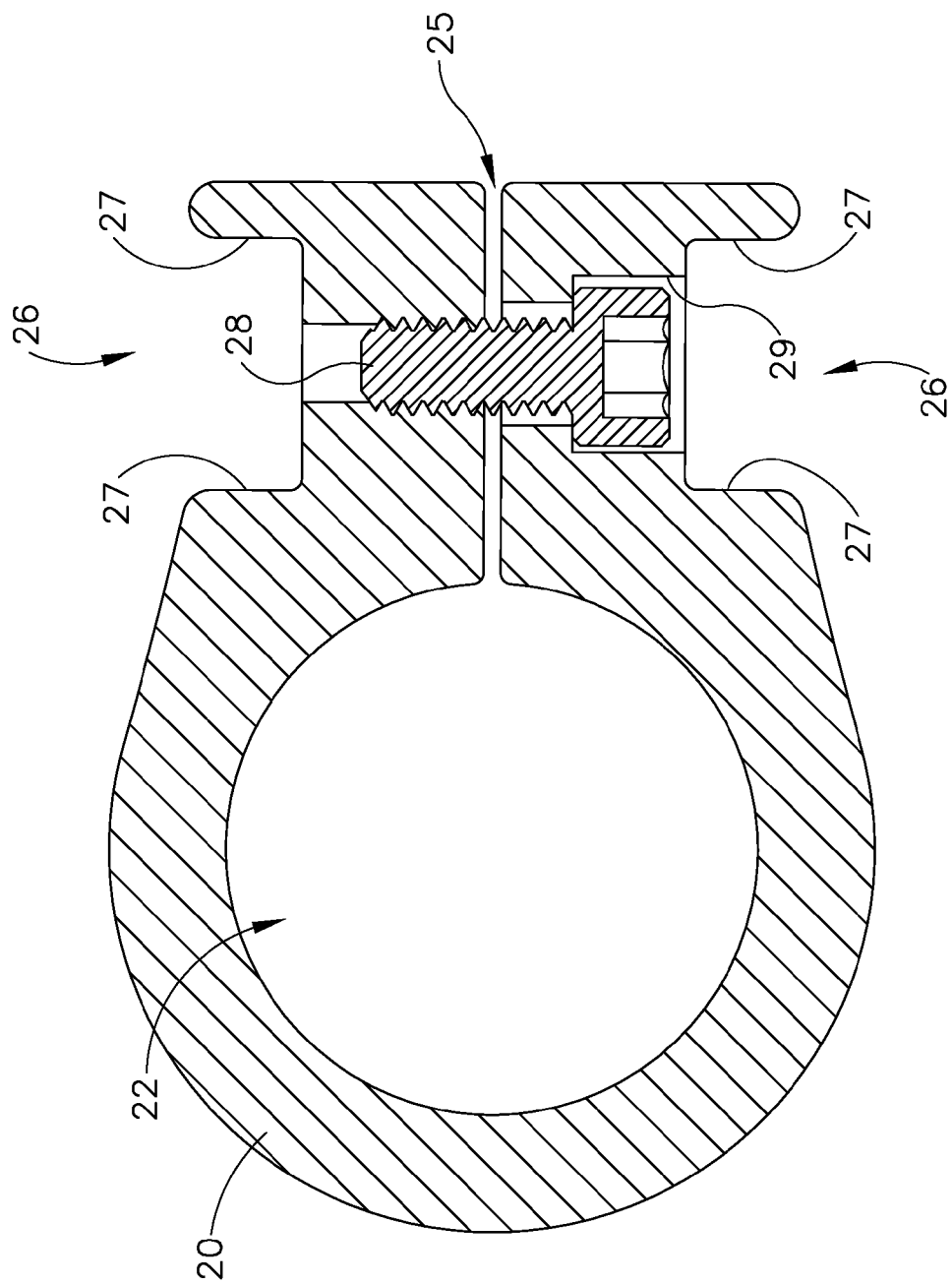
FIG. 8 depicts a cross-sectional view of the housing of FIG. 6, with the cross section taken along line 8-8 of FIG. 6.
Figure 9:
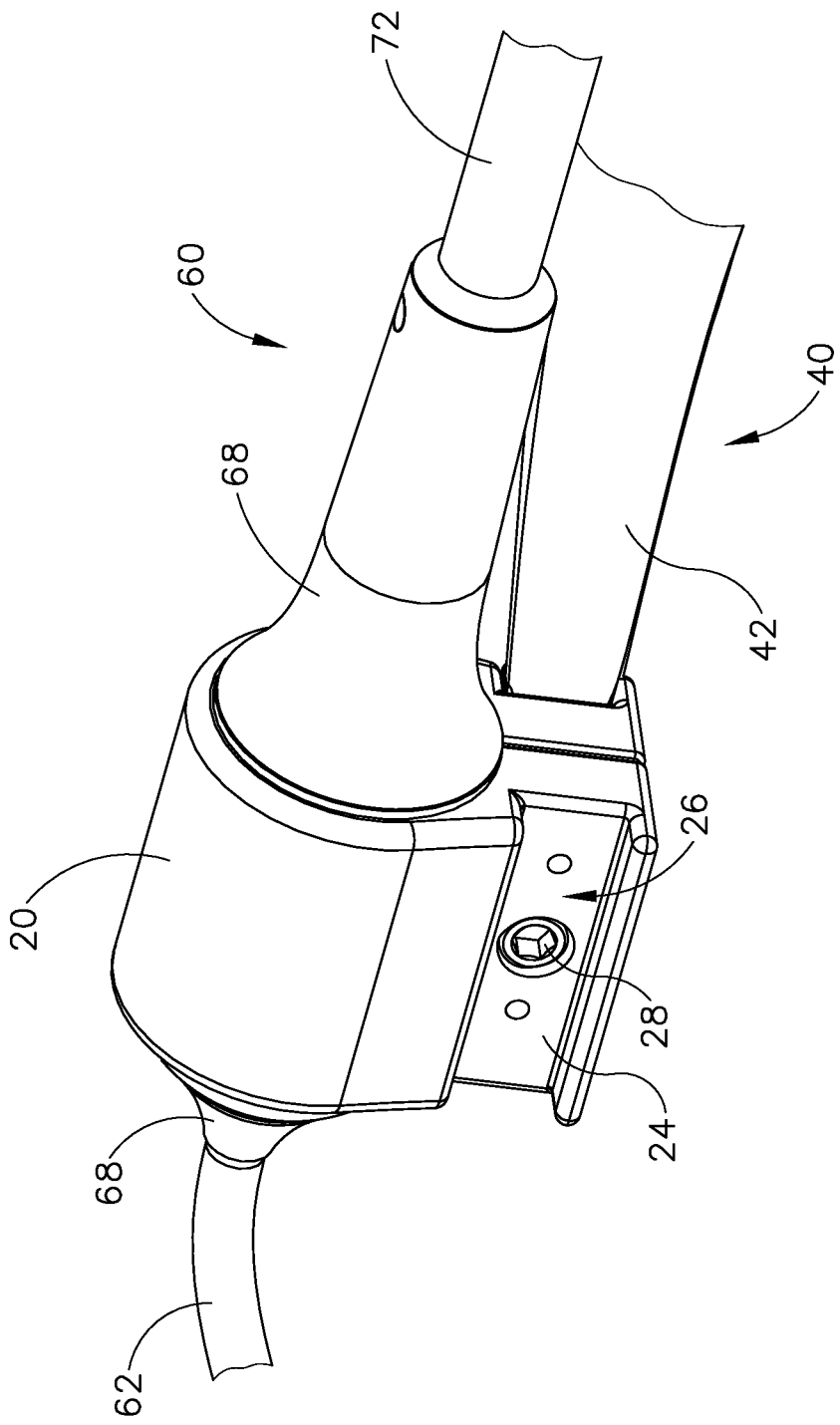
FIG. 9 depicts a perspective view of the housing of FIG. 6, with a tine removed.

FIG. 8 shows housing (20) in cross section. Clamping portion (24) defines a gap (25) that enables clamping portion (24) to be deformed outwardly to receive transducer (80) in bore (22); then be brought back inwardly to clamp onto transducer (80). In the present example, one clamping portion (24) is attached to the other with a screw (28) to maintain a clamping force on transducer (80), thereby securing housing (20) to transducer (80). As can be seen, one clamping portion (24) may be threaded such that screw (28) can engage that portion. Similarly, another clamping portion (24) may have a counter bore (29) to permit screw (28) tighten beneath groove (26). Counter bore (29) may be on either clamping portion (24), though the alignment procedure described below may warrant positioning counter bore (29) on the clamping portion (24) that receives active tine (46). Screw (28) may be tightened to draw each clamping portion (24) closer to the other—closing gap (25) between clamping portions (24). Drawing the clamping portions (24) closer to each other may accordingly permit the size of acoustic assembly receiving bore (22) to be reduced—clamping acoustic assembly (60) within housing (20) to prevent axial and rotational movement of acoustic assembly (60). Acoustic assembly receiving bore (22) may include flats, annular shoulders, and/or etc. to further secure acoustic assembly (60) relative to housing (20). Screw (28) may also be loosened to permit clamping portions to move away from one another, enlarging gap (25). Gap (25) may permit acoustic assembly receiving bore (22) to expand to a point where acoustic assembly (60) may be inserted into acoustic assembly receiving bore (22) along an axial path. As can be seen in FIG. 9, when acoustic assembly (60) is sufficiently tightened within housing (20), screw (28) may rest below the surface of groove (26) thus permitting attachment of tines (42, 46).

Acoustic assembly receiving bore (22) may also comprise gaskets, seals, or the like to seal transducer (80) within housing. Seals or gaskets may be comprised of any suitable material to seal transducer (80) and permit various suitable sterilization processes (e.g., steam, low temperature hydrogen peroxide plasma, ethylene oxide, etc.). Of course, other variations of clamping acoustic assembly (60) within housing (20) will be apparent to those of ordinary skill in the art in view of the teachings herein.

To mount and align tines (42, 46) and acoustic assembly (60) in housing (20), passive tine (42) may first be mounted to housing (20). Acoustic assembly (60) may then be inserted into the acoustic assembly receiving bore (22), aligning the axis of transducer (80) with the axis of acoustic assembly receiving bore (22). Foot (44) of passive tine (42) may then be aligned with ultrasonic blade (66) by clamping foot (44) and ultrasonic blade (66) together. Screw (28) may then be tightened to clamp acoustic assembly receiving bore (22) about acoustic assembly (60). As described above, counter bore (29) for screw (28) may be on the clamping portion (24) opposite of passive tine (42) because passive tine (42) may be secured to housing (20) before tightening of screw (28). Once screw (28) is tightened, active tine (46) may be inserted onto waveguide assembly (64) and attached to housing (20). Other suitable alignment procedures will be apparent to those of ordinary skill in the art in view of the teachings herein.

B. Exemplary Ultrasonic Transducer

Figure 10:
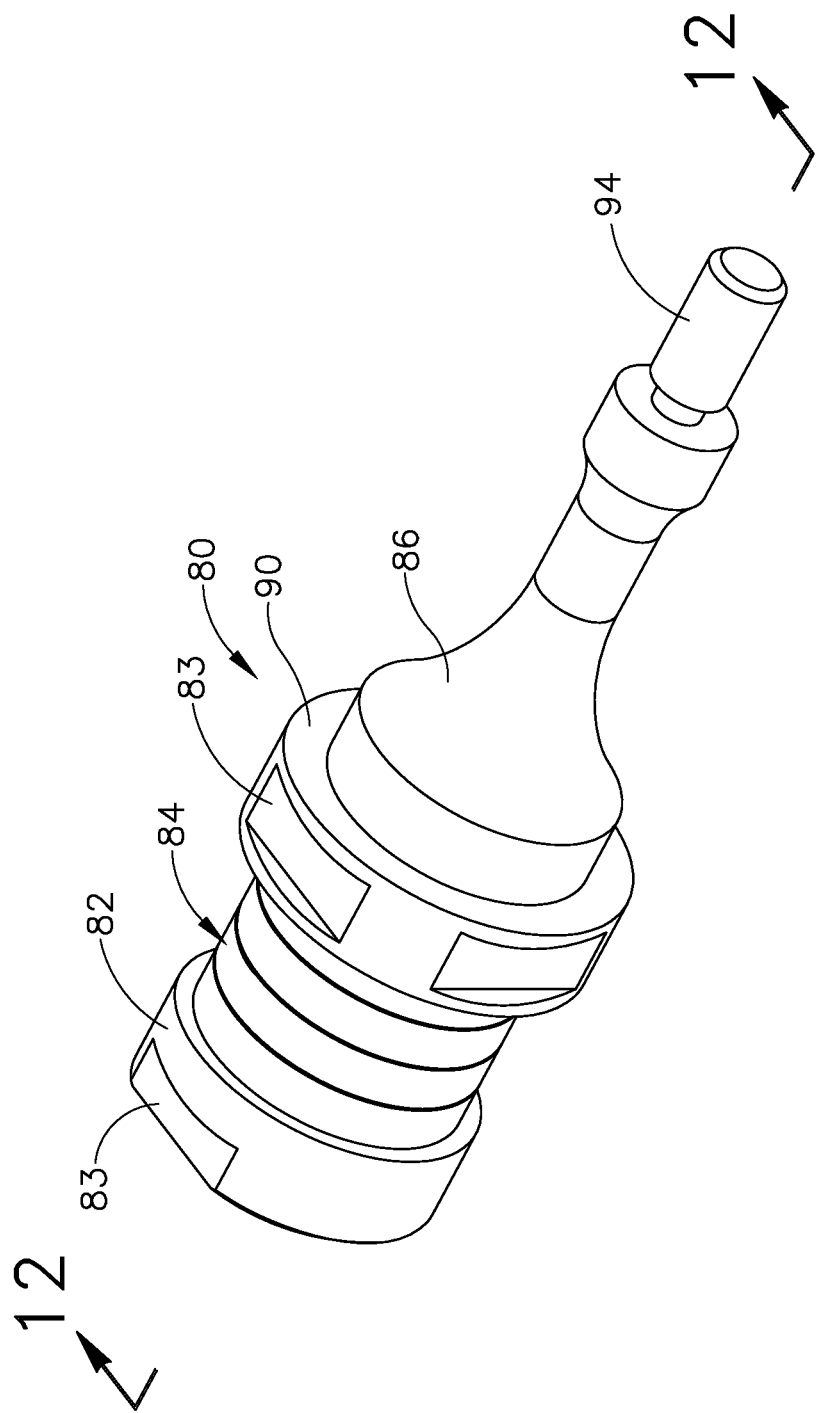
FIG. 10 depicts a perspective view of an ultrasonic transducer of the ultrasonic forceps of FIG. 1.
Figure 11:
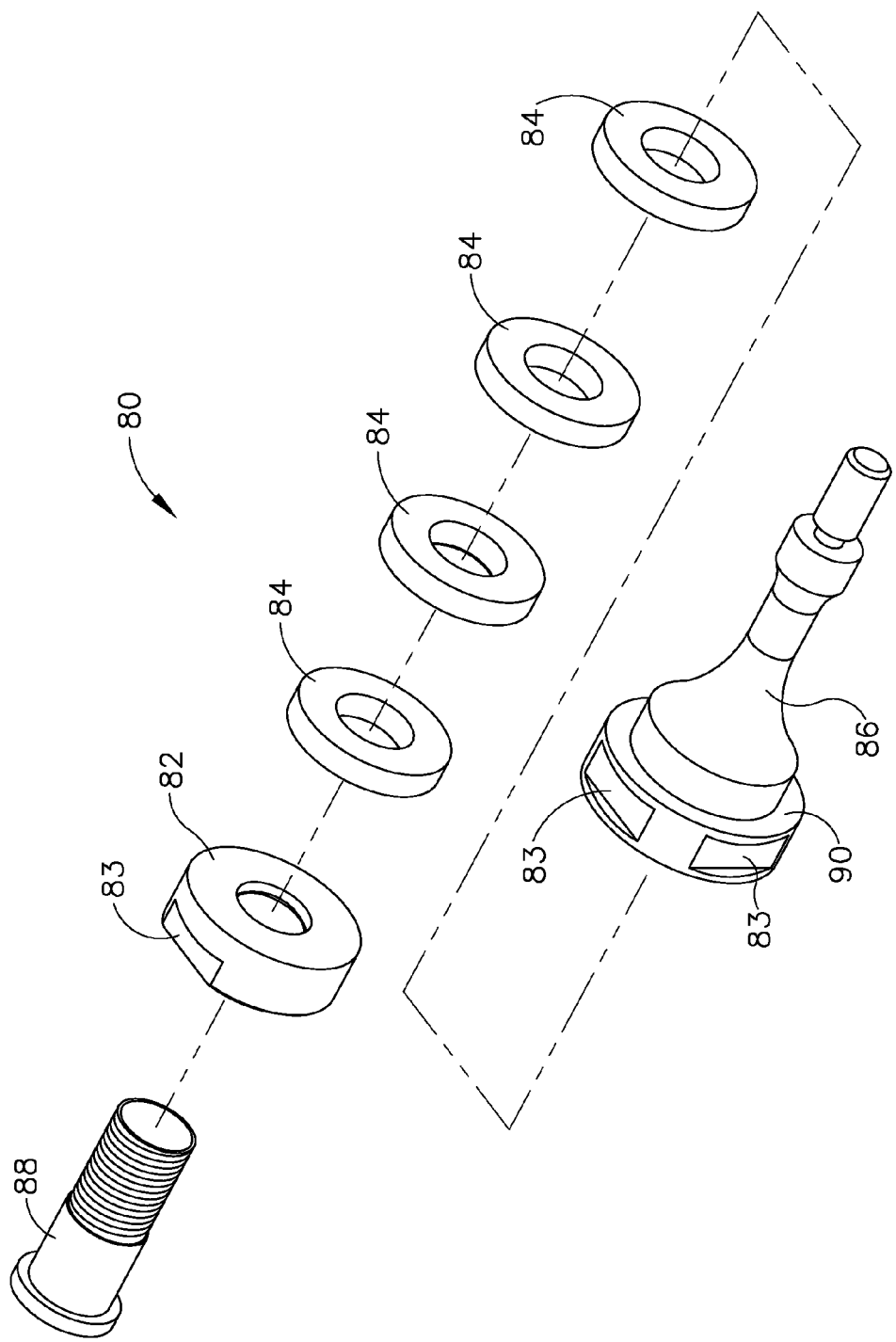
FIG. 11 depicts an exploded view of the ultrasonic transducer of FIG. 10.

FIG. 10 shows a perspective view of transducer (80). As can be seen in FIG. 11, transducer (80) comprises an end mass (82), four piezoelectric discs (84), a horn (86) and a bolt (88). The components of transducer (80) are aligned along a longitudinal axis. Four piezoelectric discs (84) are sandwiched between end mass (82) and horn (86) with bolt (88) securing end mass (82) and horn (86) together. End mass (82) may act as a flange to secure piezoelectric discs (84) proximally relative to transducer (80). Flats (83) may be added to the surface of end mass (82) to provide a surface by which housing (20) may fixedly secure transducer (80). End mass (82) may be comprised of a metallic compounds such as stainless steel, carbon steel, or the like. Piezoelectric discs (84) comprise any suitable piezoelectric material which may allow the piezoelectric discs (84) to expand or contract, in a rapidly vibrating fashion, in response to electric current such as lead zicronate titanate, quartz, or the like.

Horn (86) comprises a flange portion (90) and a threaded stud (94). Flange portion (90) may act as a flange to secure the distal position of piezoelectric discs (84) relative to transducer (80). Flange portion (90) may be configured with geometric features to fixedly secure transducer (80) in housing. To reduce transverse displacement of transducer (80) caused by vibrations, flange portion (90) is positioned at a nodal plane relative to piezoelectric discs (84). In other words, flange portion (90) is located at a longitudinal position corresponding to a node associated with ultrasonic vibrations generated by piezoelectric discs (84). The longitudinal thickness of flange portion (90) may be limited by the wavelength of the ultrasonic vibrations generated by piezoelectric discs (84). In the present example, flange portion (90) has a longitudinal width of approximately 8% of the ultrasonic wavelength generated by piezoelectric discs (84). Although such a width may vary between approximately 3 to 8% of the wavelength generated by piezoelectric discs (84). It should be understood, that in other examples longitudinal width of flange portion may vary depending on a variety of factors such as the ultrasonic vibrations utilized, transducer length and/or shape, waveguide length and/or shape, and the like.

Horn (86) is configured to direct vibrations from piezoelectric discs (84) such that the vibrations may be communicated to waveguide assembly (64). Threaded stud (94) is configured to mechanically and acoustically couple horn (86) with waveguide (78). In the present example, horn (86) is of a unitary design comprising a single material. Horn (86) may be constructed of any material suitable to communicate vibrations from piezoelectric discs (84) such as titanium, stainless steel, carbon steel tungsten or the like.

Bolt (88) is shown as using a threaded shaft and a collar to secure horn (86) to end mass (82). In other examples, bolt (88) may be omitted in lieu of another means of connecting end mass (82) and horn (86). For instance, horn (86) may be equipped with cylindrical member extending proximally from the proximal end of horn (86). Such an extension may then be welded to end mass. Still other examples for securing end mass (82) to horn (86) to compress piezoelectric discs (84) will be apparent to those of ordinary skill in the art in view of the teachings herein.

Figure 12:
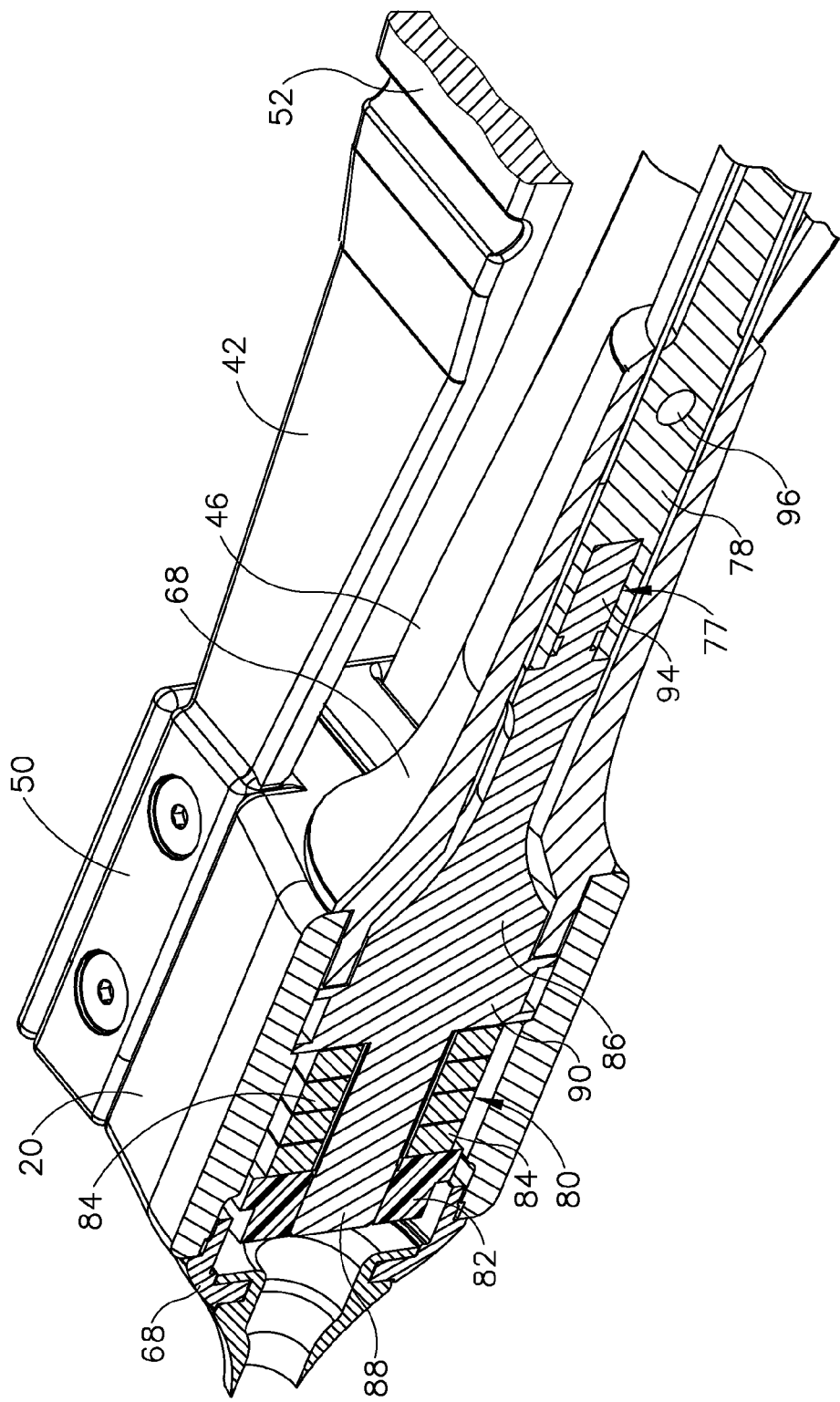
FIG. 12 depicts a cross-sectional view of the ultrasonic transducer of FIG. 10 inserted into the housing of FIG. 6, with the cross section taken along line 12-12 of FIG. 10.

FIG. 12 shows transducer (80) attached to housing (20) in cross section. As can be seen, acoustic assembly receiving bore (22) may fixedly secure transducer (80) by engaging flange portion (90) of horn (86) and flats (83) of end mass (82). Horn (86) extends distally from housing (20) where it may connect to waveguide assembly (64) using a connection suitable to communicate vibrations to waveguide assembly (64). In particular, threaded stud (94) of horn (86) may engage a cooperatively threaded recess (77) in waveguide (78).

As described above, transducer (80) may receive electrical power from the generator. In particular, transducer (80) may convert that power into ultrasonic vibrations through piezoelectric principals. By way of example only, the generator may comprise a GEN 300 or a GEN 11 sold by Ethicon Endo-Surgery, Inc. of Cincinnati, Ohio. In addition or in alternative, the generator may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 4, 2015, the disclosure of which is incorporated by reference herein.

Ultrasonic vibrations that are generated by transducer (80) may be communicated to waveguide assembly (64) via horn (86). Waveguide assembly (64) may then communicate ultrasonic vibrations to ultrasonic blade (66). As noted above, when ultrasonic blade (66) is in an activated state (i.e., vibrating ultrasonically), ultrasonic blade (66) is operable to effectively cut through and seal tissue, particularly when the tissue is being clamped between passive tine (42) and ultrasonic blade (66).

C. Exemplary Ultrasonic Waveguide

Figure 13:
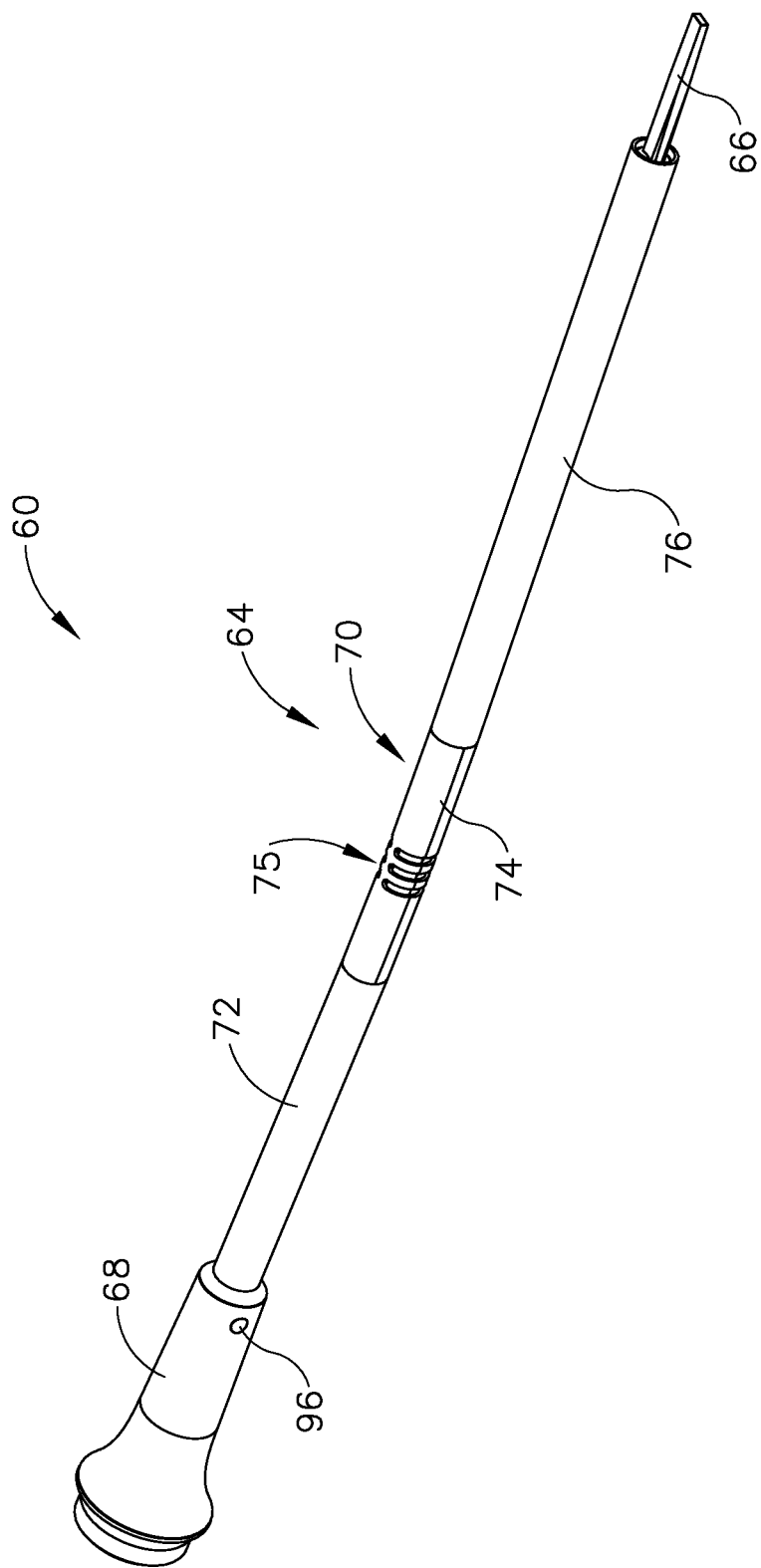
FIG. 13 depicts a perspective view of the waveguide assembly of the ultrasonic forceps of FIG. 1.

FIG. 13 shows a perspective view of waveguide assembly (64). Waveguide assembly (64) comprises a three piece sheath (70) and a waveguide (78). Three piece sheath (70) comprises a straight proximal portion (72), a bendable slotted portion (74), and a straight distal portion (76).

Proximal and distal portions (72, 76) are configured to align coaxially with waveguide (78) along portions of waveguide (78) that are correspondingly straight. Proximal portion (72) may be inserted into transducer housing member (68). By way of example only, proximal portion (72) is fixedly secured to transducer housing member (68) by a pin (96) inserted through holes in proximal portion (72) and transducer housing member (68). Pin (96) is inserted transversely through waveguide (78) at a longitudinal position corresponding to a node associated with ultrasonic vibrations communicated through waveguide (78). In other examples proximal portion (72) may be fixedly secured to transducer housing member (68) by any suitable means such as snap fits, adhesive bonds, welding and/or etc.

Slotted portion (74) is configured to align coaxially with waveguide (78) along portions of waveguide (78) that are bent and/or curved. Transverse slots (75) cut into slotted portion (74) may permit slotted portion (74) to flex and/or bend to conform to the corresponding bend and/or curve of waveguide (78). The proximal and distal ends of slotted portion (74) may align with proximal portion (72) and distal portion (76), respectively, and be joined by any suitable joining method, such that proximal portion (72), slotted portion (74), and distal portion (76) form a unitary sheath around waveguide (78). Suitable means of joining proximal portion (72), slotted portion (74), and distal portion (76) may include laser welding, ultrasonic welding, adhesive bonding, and the like. Of course, a sheath surrounding waveguide (78) may take many alternative configurations, as will be described in greater detail below.

Figure 14:
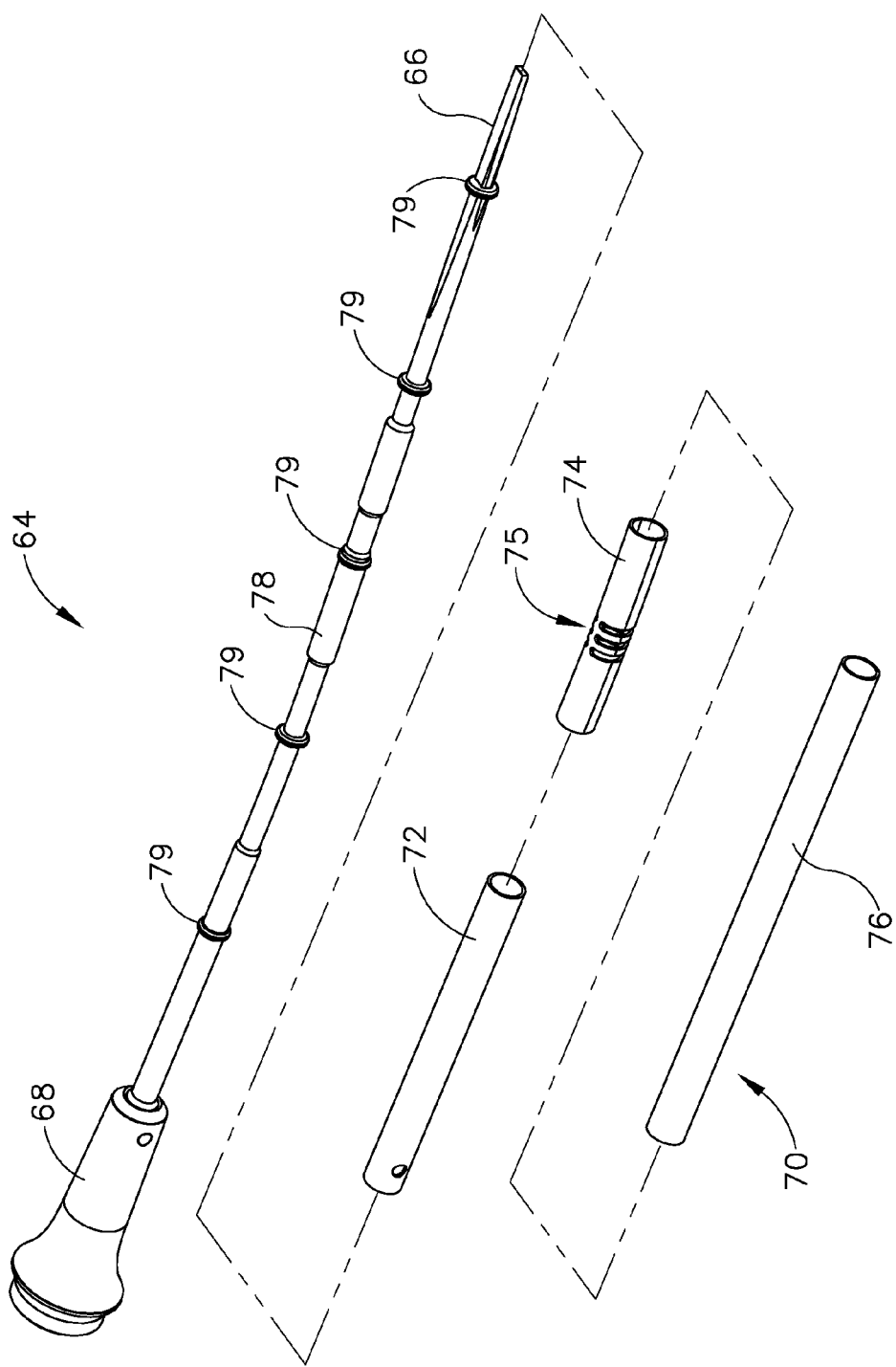
FIG. 14 depicts a partially exploded view of the waveguide assembly of FIG. 13.

Waveguide (78) comprises a generally cylindrical shaft extending distally from horn (86) of transducer (80). The distal end of waveguide (78) is shaped into ultrasonic blade (66). As shown in FIG. 14, a plurality of spacer rings (79) is disposed along the length of waveguide (78). Spacer rings (79) are added to maintain suitable spacing between waveguide (78) and proximal portion (72), slotted portion (74), or distal portion (76). Spacer rings (79) are located at longitudinal positions corresponding to nodes associated with ultrasonic vibrations communicated through waveguide (78). Although five spacer rings (79) are shown, it should be understood that any suitable number of spacer rings (79), having any suitable spacing, may be used. Moreover, spacer rings (79) may be separate from waveguide (78) or integrally formed by waveguide (78). Where spacer rings (79) are formed separately from waveguide (78), spacer rings (79) may comprise rubber o-rings. Other suitable configurations of spacer rings (79) will be apparent to those of ordinary skill in the art in view of the teachings herein.

Waveguide (78) may require a precision bend and/or curve so that ultrasonic blade (66) may contact passive tine (42). Accordingly, in some instances, waveguide (78) may be bent or curved prior to installing proximal portion (72), slotted portion (74), and distal portion (76) on waveguide (78). When such a bend or curve in waveguide (78) is used, the bend or curve may be located at a longitudinal position corresponding to an anti-node associated with ultrasonic vibrations communicated along waveguide (78), to thereby minimize transverse motion in waveguide (78). Once waveguide is bent or curved, slotted portion (74) may be first installed on waveguide (78). Slotted portion (74) may then be bent and/or shaped to align with the bend or curve of waveguide (78). Subsequently, proximal portion (72) and distal portion (76) may be placed on waveguide where they may be fixedly secured to slotted portion (74), as described above. Three piece sheath (70) may also include a seal (not shown) such as a heat shrink tubing placed over the slotted portion. Seal may prevent tissue, fluids, or other foreign materials from entering the space between sheath (70) and waveguide (78), thus improving the reusability of waveguide assembly (64). The proximal end of sheath (70) may be sealed by capturing the seal within transducer housing member (68). Likewise, the distal end of sheath (70) may be sealed using the distal most spacer ring (79). Of course, seal is entirely optional and may be omitted entirely. In other examples, a flexible thin-walled mechanical bellows (not shown) may be used in lieu of slotted portion (74), thus eliminating the need for seal. In such a configuration, proximal and distal portions (72, 76) may have a snug fit over or inside the ends of bellows to aid in sealing sheath (70).

As noted above, ultrasonic blade (66) is operable to cut through and seal tissue when ultrasonic blade (66) is in an activated state. It should be understood that waveguide (78) may be configured to amplify mechanical vibrations transmitted through waveguide (78) from transducer (80). Furthermore, waveguide (78) may include features operable to control the gain of the longitudinal vibrations along the waveguide (78) and/or features to tune the waveguide (78) to resonant frequency of the system.

In the present example, the distal end of ultrasonic blade (66) is located at a position corresponding to an anti-node associated with resonant ultrasonic vibrations communicated through waveguide (78), in order to tune the acoustic assembly (60) to a preferred resonant frequency $f_o$ when the acoustic assembly is not loaded by tissue. Ultrasonic blade (66) may have an active length of approximately 7 mm, though the active length could be as long as approximately 9 mm. When transducer (80) is energized, the distal end of ultrasonic blade (66) is configured to move longitudinally in the range of, for example, approximately 10 to 500 microns peak-to-peak, and in some instances in the range of about 20 to about 200 microns at a predetermined vibratory frequency $f_o$ of, for example, 60 to 120 kHz. Other vibratory frequency $f_o$ ranges could include, for example, 20 to 200 kHz, 60 to 150 kHz, or 90 to 115 kHz. By way of example only, nominal frequencies may include 115 kHz, 90 kHz, or 80 kHz, depending on transducer (80) design, power applied thereto, and/or other variables. Additionally, transducer (80) may be driven at power levels ranging from 12 to 50 watts with power levels being potentially dependent on variables such as desired frequency, ultrasonic blade (66) design, transducer (80) design, and/or the like. When transducer (80) of the present example is activated, these mechanical oscillations are transmitted through waveguide (78) to reach ultrasonic blade (66), thereby providing oscillation of ultrasonic blade (66) at the resonant ultrasonic frequency. Thus, when tissue is secured between ultrasonic blade (66) and passive tine (42), the ultrasonic oscillation of ultrasonic blade (66) may simultaneously sever the tissue and denature the proteins in adjacent tissue cells, thereby providing a coagulate effect with relatively little thermal spread. In some examples, as will be described in greater detail below, an electrical current may also be provided through ultrasonic blade (66) and/or passive tine (42) to also seal the tissue using electrocautery.

II. Exemplary Alternative Features for Ultrasonic Forceps

In some instances it may be desirable to have alternative features of forceps (10). Variations of features utilized with forceps (10) may permit forceps (10) to be used in a more robust array of surgical procedures or with a larger variety of surgical techniques. To the extent that any of the examples discussed below are shown and described in the context of a variation of one particular feature of forceps (10), it should be understood that the same teachings may be readily applied to the other variations of features utilized with forceps (10). Each example described below should therefore not be viewed as only having applicably to that particular feature of forceps (10). Furthermore, it is contemplated that the teachings below may be readily applied to other kinds of forceps (10), not just variations of the features utilized with forceps (10).

A. Exemplary Alternative Tine Having Piezoelectric Material

FIG. 15 shows an exemplary alternative tine (140). Tine (140) may be used in addition to or in lieu of tines (42, 46) described above. Tine (140) may combine many of the same elements and features of tines (42, 46) discussed above, with some modifications as will be described below. In the present example, tine (140) has a shape similar to passive tine (42), above. Similarly, tine (140) has an attachment member (150), and a gripping portion (152). Although tine (140) is shown as having a foot (144) of similar shape to foot (44) discussed above, it should be understood that foot (144) may be configured with a geometry similar to ultrasonic blade (66). In contrast to passive tine (42), tine (140) has piezoelectric pads (142) affixed to tine (140). Piezoelectric pads (142) are shown as being oriented near gripping portion (152), though they could be placed in any suitable position (e.g., at the distal end of tine (140)).

It should be understood that piezoelectric pads (142) may be integrated into tine (140) to form a bimorph. Tine (140) is shown as having a piezoelectric pad (142) on two opposing surfaces of tine (140). Piezoelectric pads (142) may be coupled with a cable via wires, traces, and/or any other suitable kinds of electrical conduits. A generator may thereby provide electrical power to piezoelectric pads (142) to selectively activate piezoelectric pads (142). Because piezoelectric pads (142) deliver ultrasonic vibrations directly to tine (140), which may be held by a user, gripping portions (152) may be configured to be vibrationally isolated from piezoelectric pads. In some versions, at least a portion of tine (140) may be constructed of a bimetallic material (not shown) that may be used in lieu of piezoelectric pads (142). For instance, the bimetallic material may expand and contract through an application of an external stimulus such as localized heat or electrical power.

Figure 16A:
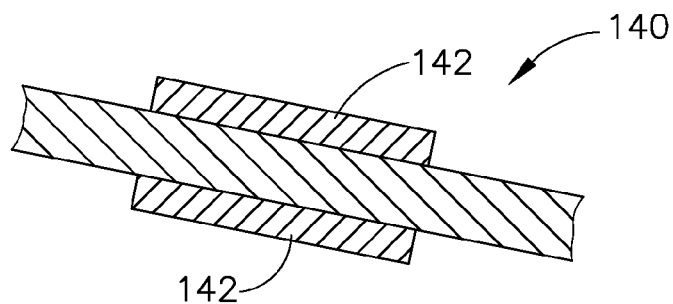
FIG. 16A depicts a cross-sectional view of the tine of FIG. 15, with the cross section taken along line 16-16 of FIG. 15.
Figure 16B:
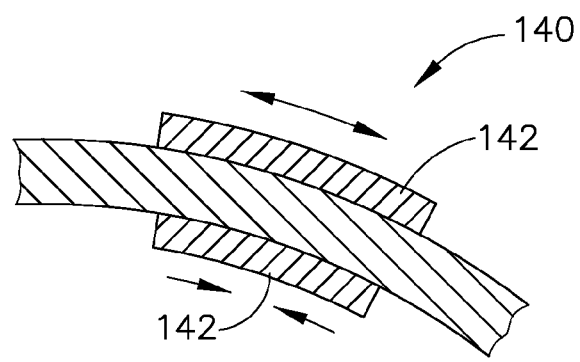
FIG. 16B depicts a cross-sectional view of the tine of FIG. 15 in a first bent state, with the cross section taken along line 16-16 of FIG. 15.
Figure 16C:
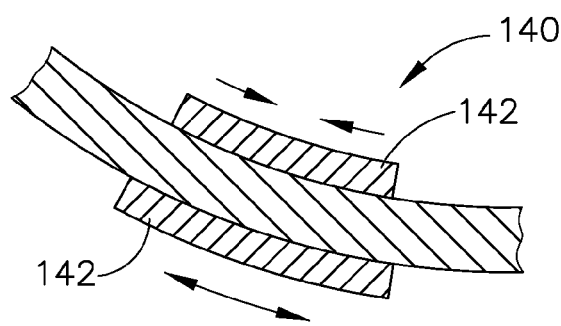
FIG. 16C depicts a cross-sectional view of the tine of FIG. 15 in a second bent state, with the cross section taken along line 16-16 of FIG. 15.
Figure 17:
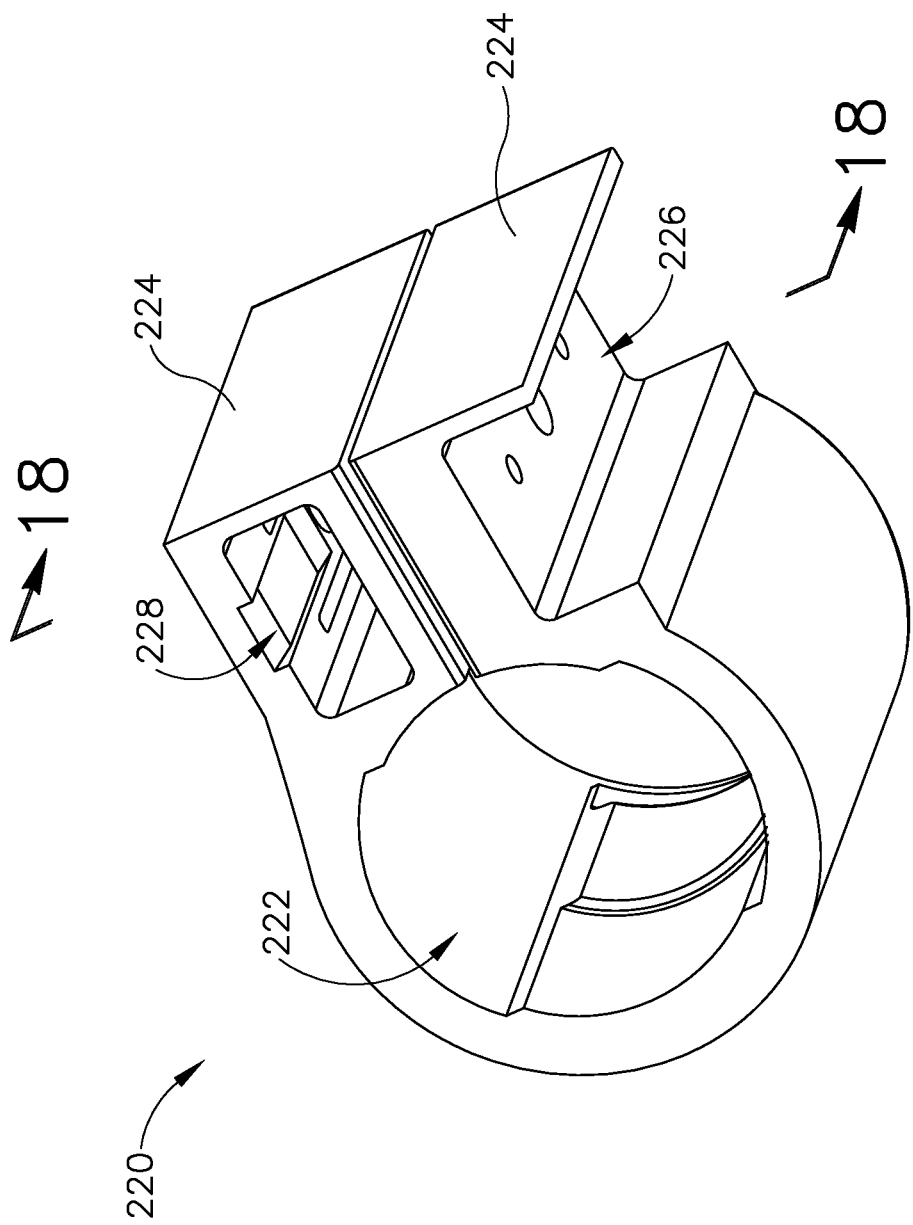
FIG. 17 depicts a perspective view of an exemplary alternative housing that may be incorporated into the ultrasonic forceps of FIG. 1.
Figure 18:
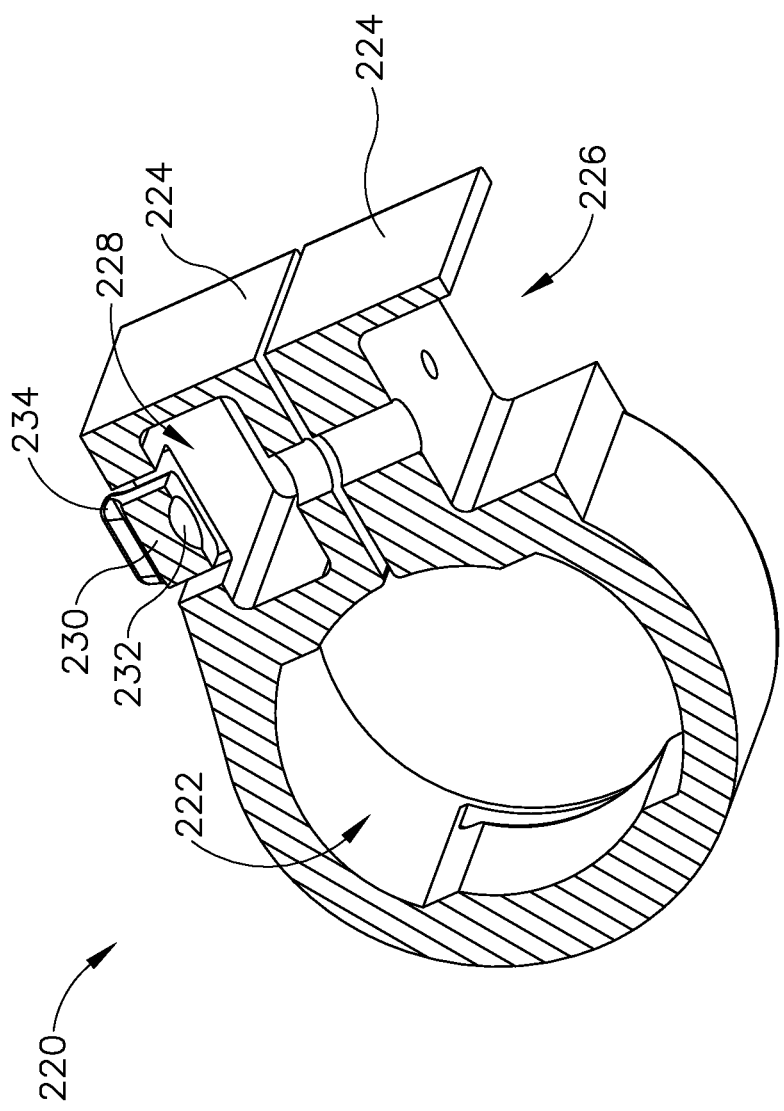
FIG. 18 depicts a cross-sectional view of housing of FIG. 17, with the cross section taken along line 18-18 of FIG. 17.

Piezoelectric pads (142) may be operable to cooperatively induce ultrasonic vibrations in tine (140). In particular, FIGS. 16A-16C show tine (140) in various stages of operation that may create ultrasonic vibrations in tine (140). In FIG. 16A, piezoelectric pads (142) have not been activated. Accordingly, the portion of tine (140) surrounded by piezoelectric pads (142) has substantially zero transverse displacement.

In FIG. 16B, piezoelectric pads (142) are shown in an activated state. In particular, an electric current has been applied to each piezoelectric pad (142) with each pad (142) having a different polarity applied thereto. Accordingly, one pad (142) may respond to the current by expanding and the other by contracting. As can be seen, when piezoelectric pads (142) oppose one another by opposingly expanding or contracting, piezoelectric pads (142) may cause the portion of tine (140) surrounded by piezoelectric pads (142) to have some transverse displacement. This effectively may create a slight bend in tine (140).

FIG. 16C shows an operational condition substantially the same as that shown in FIG. 16B, except an electric current of opposite polarity is applied to piezoelectric pads (142). This may create a transverse displacement or bend in tine (140) that is the inverse of that seen in FIG. 16B. Accordingly, piezoelectric pads (142) may be cycled through the operational states shown in FIGS. 16B and 16C rapidly to stimulate ultrasonic vibrations in tine (140). It should be understood that other configurations or operational states may similarly stimulate ultrasonic vibrations. For instance, piezoelectric pads (142) may be of differing shapes and/or sizes. In other examples, only one piezoelectric pad (142) may be active at a time. Other piezoelectric pad (142) configurations or operational states will be apparent to those of ordinary skill in the art in view of the teachings herein.

B. Exemplary Alternative Housing and Removable Tine

FIGS. 17 through 21 shows an exemplary alternative housing (220). Housing is generally substantially the same as housing (20) shown above with certain exceptions described below. Housing (220) comprises an acoustic assembly receiving bore (222), two clamping portions (224), and a groove (226). These elements of housing (220) are substantially the same as for housing (20) described above. In contrast to housing (20), housing (220) has a tine receiving channel (228) instead of a second groove (26).

Tine receiving channel (228) is configured to permit a tine (240) to quickly be removed from housing (220) without the need for additional tools. As can be seen in FIGS. 17 through 21, tine receiving channel (228) comprises a resiliently biased locking member (230). Locking member (230) is resiliently biased to engage complementary geometry of an attachment member (250) of a tine (240). As can best be seen in FIG. 21, tine (240) may be inserted into tine receiving channel (228) where a raised portion (254) of tine (240) may engage a corresponding indented portion (232) in locking member (230). In other words, raised portion (254) may be received in indented portion (232) like a detent. Similarly, a user may remove tine (240) by applying force to a disengagement member (234) thus lifting indented portion (232) of locking member (230) out of engagement with raised portion (254) of tine (240). Thus, when raised portion (254) is disposed in indented portion (232), tine (240) is selectively secured to housing (220).

The selective removability of tine (240) relative to housing (220) permits tine (240) to be a disposable part within an otherwise reusable forceps (10). For instance, the distal end of tine (240) may comprise a PTFE/Teflon pad that may wear out over time. When the PTFE/Teflon pad wears out, tine (240) may be replaced instead of the entire forceps (10). Moreover, the selective removability of tine (240) may permit tine (240) to be part of a suite of tines (240) configured for different surgical procedures or techniques. Thus, an operator could use the same forceps (10) with different tines (240) corresponding to different surgical procedures; and/or the operator could switch out tines (240) during a surgical procedure. It should be understood that in other examples tine receiving channel (228) may have various alternative configurations and/or geometries that may be suitable to allow quick release of tine (240). Furthermore, tine receiving channel (228) may be configured for use with a tine (240) having the characteristics of an active or passive tine, similar to those discussed above. Other configurations and/or geometries will be apparent to those of ordinary skill in the art in view of the teachings herein.

Figure 19:
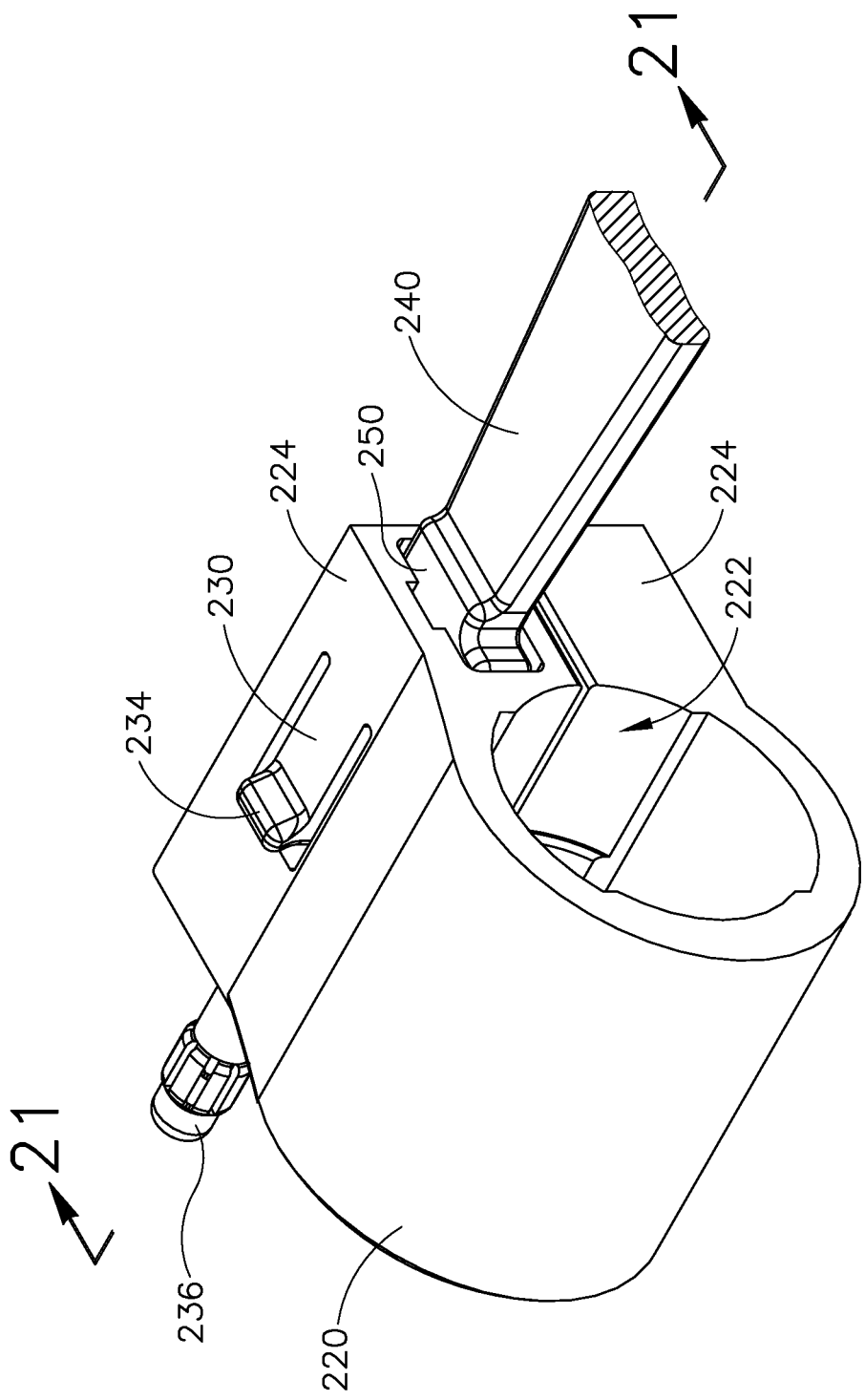
FIG. 19 depicts a perspective view of the housing of FIG. 17, with a removable tine inserted into the housing.
Figure 20:
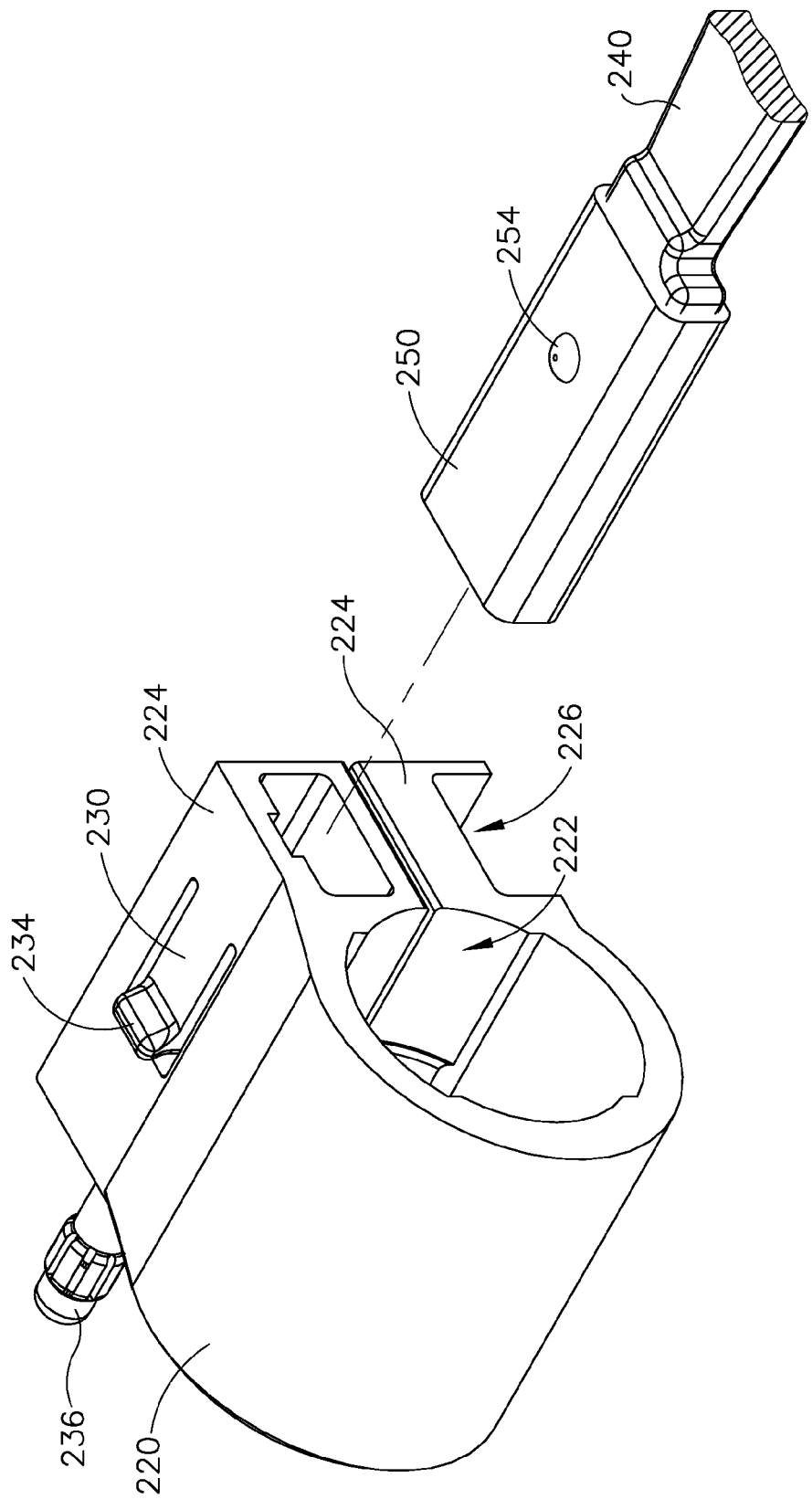
FIG. 20 depicts a partially exploded view of the housing and tine of FIG. 19.
Figure 21:
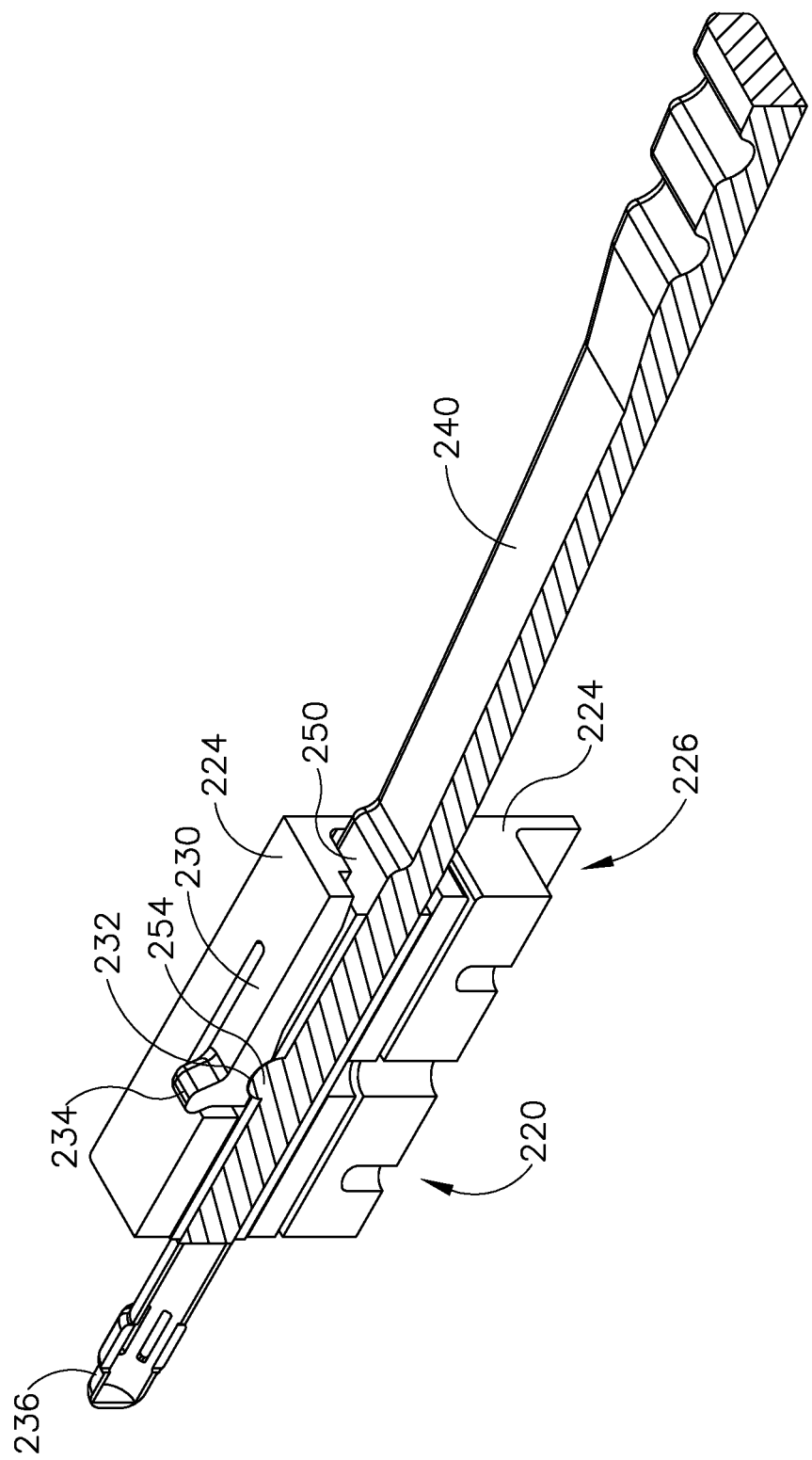
FIG. 21 depicts a cross sectional view of the housing of FIG. 19, with the cross section taken along line 21-21 of FIG. 19.

FIGS. 19 through 21 also depict housing (220) as comprising a connector (236). Connector is configured to permit an electrical power source cable (not shown) to attach to housing (220) such that the power source cable may communicate electrical power to tine (240) to enable tine (240) to deliver RF energy to tissue. Accordingly, forceps (10) may be a combination ultrasonic/RF forceps (10) when equipped with housing (220). A combination ultrasonic/RF forceps (10) may utilize ultrasonic operational states separately from RF operational states depending on the surgical procedure in which forceps (10) is being used. For instance, ultrasonic operational states may be used with ear, nose and throat, or spinal surgical procedures. In contrast, RF operational states may be used in surgical procedures involving the brain. An operator may even selectively alternate between an ultrasonic mode and an RF mode within the same surgical procedure (e.g., based on the location of the anatomy and/or the state of the anatomy where forceps (10) are being used at that particular moment in the procedure). It is also contemplated that tine (240) may be used in an ultrasonic mode and an RF mode simultaneously (or at least in a rapidly alternating fashion). By way of example only, forceps (10) may be operable to alternate between ultrasonic activation of tine (240) and RF activation of tine (240), in an interlaced fashion, during a single transection of tissue. In other words, tine (240) may rapidly and automatically alternate between ultrasonic and RF power while tine (240) is in contact with tissue. As yet another merely illustrative example, forceps (10) may provide a combination of ultrasonic and RF capabilities in accordance with at least some of the teachings of U.S. patent application Ser. No. 14/086,085, entitled "Ultrasonic Surgical Instrument with Electrosurgical Feature," filed Nov. 21, 2013, published as U.S. Publication No. 2015/0141981 on May 21, 2015, issued as U.S. Pat. No. 9,949,785 on Apr. 24, 2018, the disclosure of which is incorporated by reference herein.

To utilize RF operational states, housing (220) may fully or partially comprise an electrically insulative material (e.g., plastic, etc.) such that housing (220) is configured to electrically isolate tine (240) from an operator's hand and/or from other components of forceps (10). For additional insulative properties, a plastic or epoxy boot (not shown) may be overmolded onto attachment member (250) of tine (240). Additionally, to protect an operator when tine (240) is electrically activated, a substantial part of the region of tine (240) that is distal to attachment member (250) may be overmolded with a stiff plastic (e.g., glass reinforced plastic) or rubber. Of course, the distal-most tip of tine (240) may be exposed from such an insulative material in order to enable the tip to apply electrical energy to tissue. RF signals may then be communicated from the electrical power source to tine (240) permitting tine to use RF energy to simultaneously cut and seal tissue. Although connector (236) is shown as being attached to housing (220), it should be understood that connector (236) may be alternatively attached to tine (240) and housing (220) may merely provide a space through which connector (236) may penetrate. In other words, connector (236) may be a unitary and integral feature of tine (240), extending proximally from attachment member (250). Thus, when tine (240) is removed from housing (220) and a non-RF tine (42) is secured to housing (220), there may be no connector (236) extending proximally from connector (220).

In the present example housing (220) is shown as having a single connector (236). Thus, only a single tine (240) may be in communication with RF instrument (not shown) making forceps (10) a mono-polar forceps. In other examples, housing (220) may be configured with a second connector (not shown) for another tine (e.g., similar to tine (246) described above) making forceps (10) a bi-polar forceps. In such a configuration, the second connector may be internally connected to an electrically conductive transducer (80), permitting RF energy communication to ultrasonic blade (66). In such a configuration, tine (240) may form one pole and another tine (e.g., active tine (46) discussed above) may form another pole. It should also be understood that housing (220) and just a single connector (236) may be configured to provide power to a transducer (80) and to provide bi-polar RF energy, such that two separate connectors (236) are not necessarily required in order to provide bi-polar RF energy. For instance, connector (236) may have two separate electrical paths (e.g., coaxial, etc.). Connector (236) may be of any suitable shape and/or geometry sufficient to communicate electrical power for application of RF energy by forceps (10). Other suitable connector configurations, shapes, and/or geometries will be apparent to those of ordinary skill in the art in view of the teachings herein.

C. Exemplary Alternative Passive Tine Ends

To the extent that any of the examples discussed below are shown and described in the context of a variation of tines (42, 46) of forceps (10), it should be understood that the same teachings may be readily applied to the other kind of tine (240). Thus, in addition to what is contemplated below, a user may select among the various available tines (42, 46, 240) to couple a particular tine (42, 46, 240) to housing (220).

Figure 22:
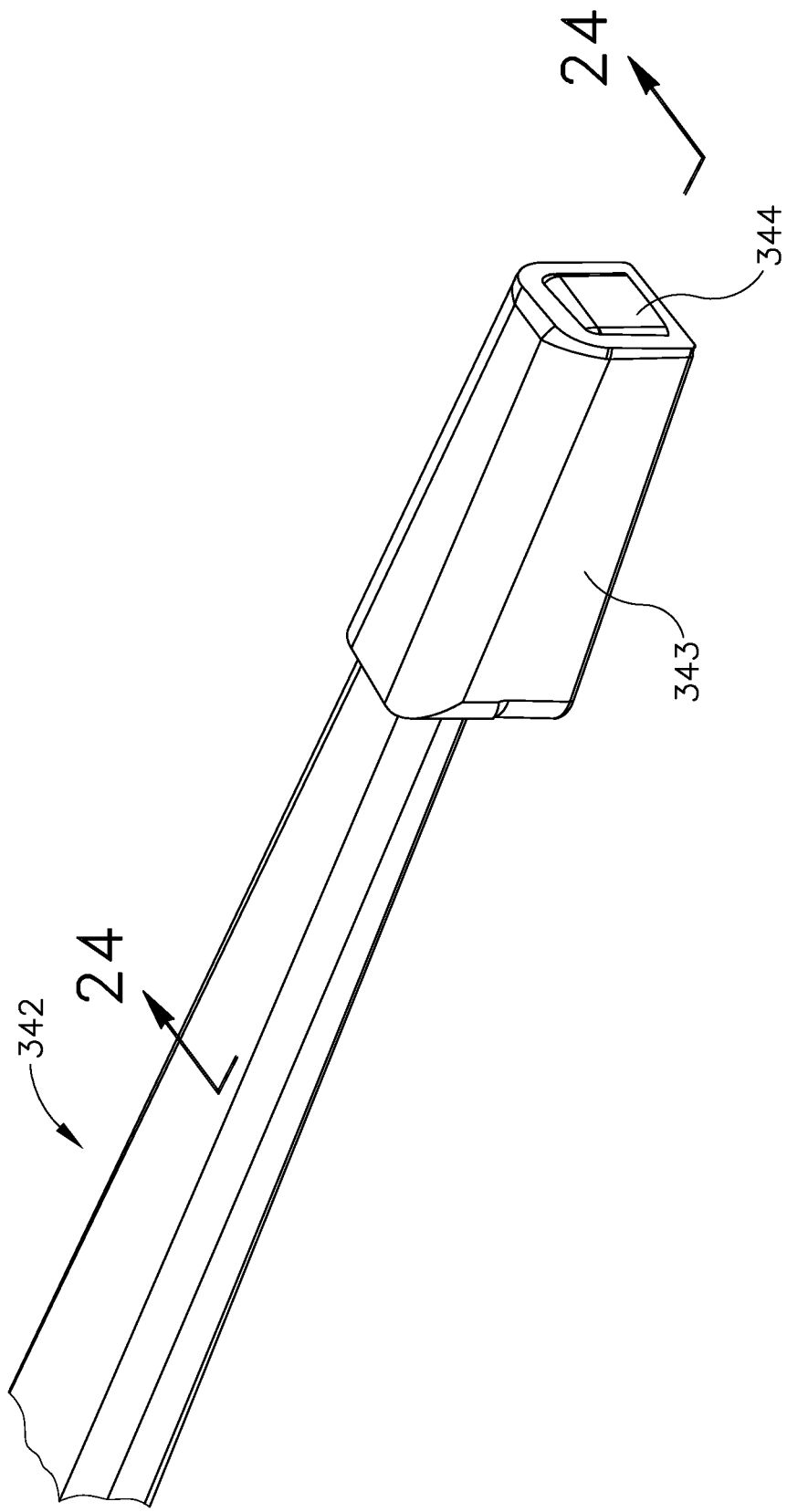
FIG. 22 depicts a perspective view of an exemplary alternative pad configuration that may be incorporated into the ultrasonic forceps of FIG. 1.
Figure 23:
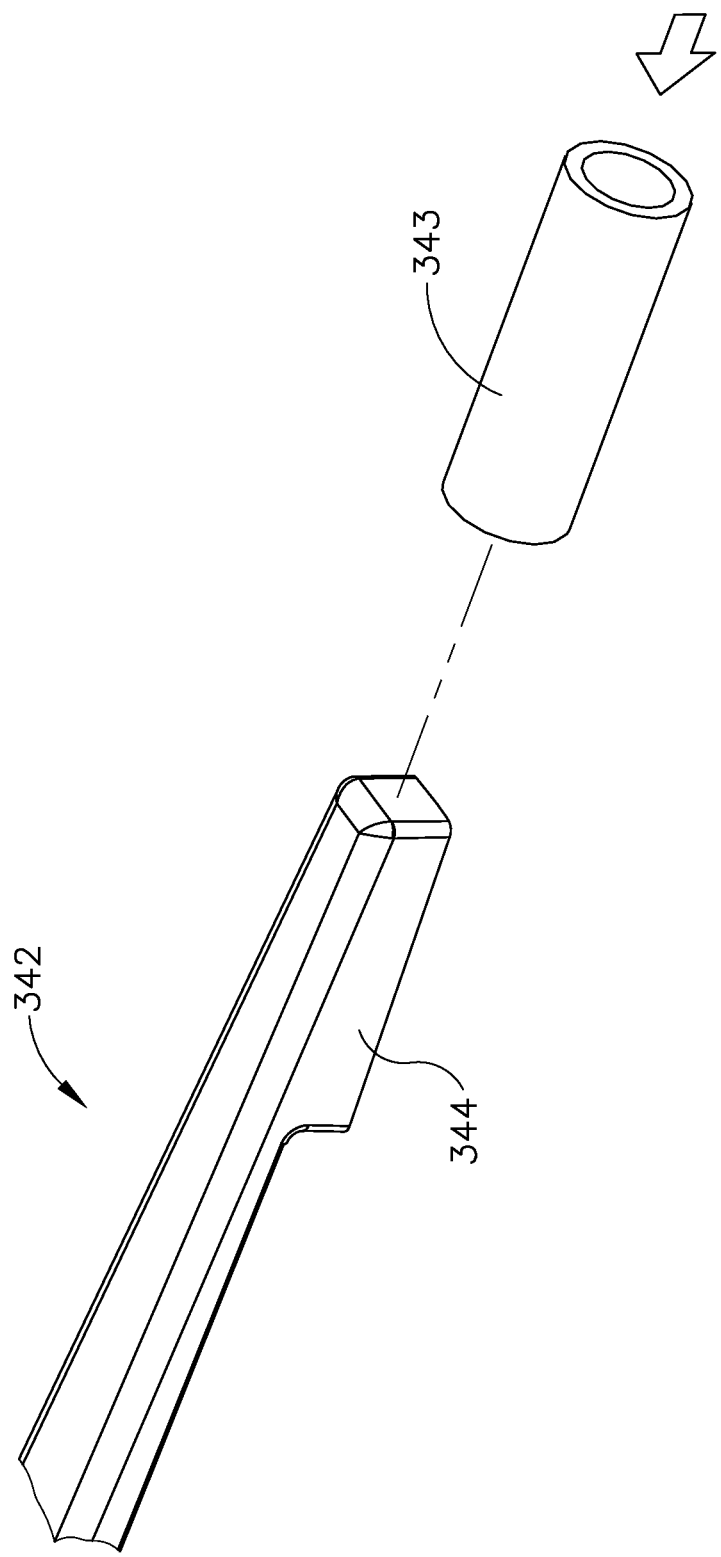
FIG. 23 depicts an exploded view of the pad configuration of FIG. 22.
Figure 24:
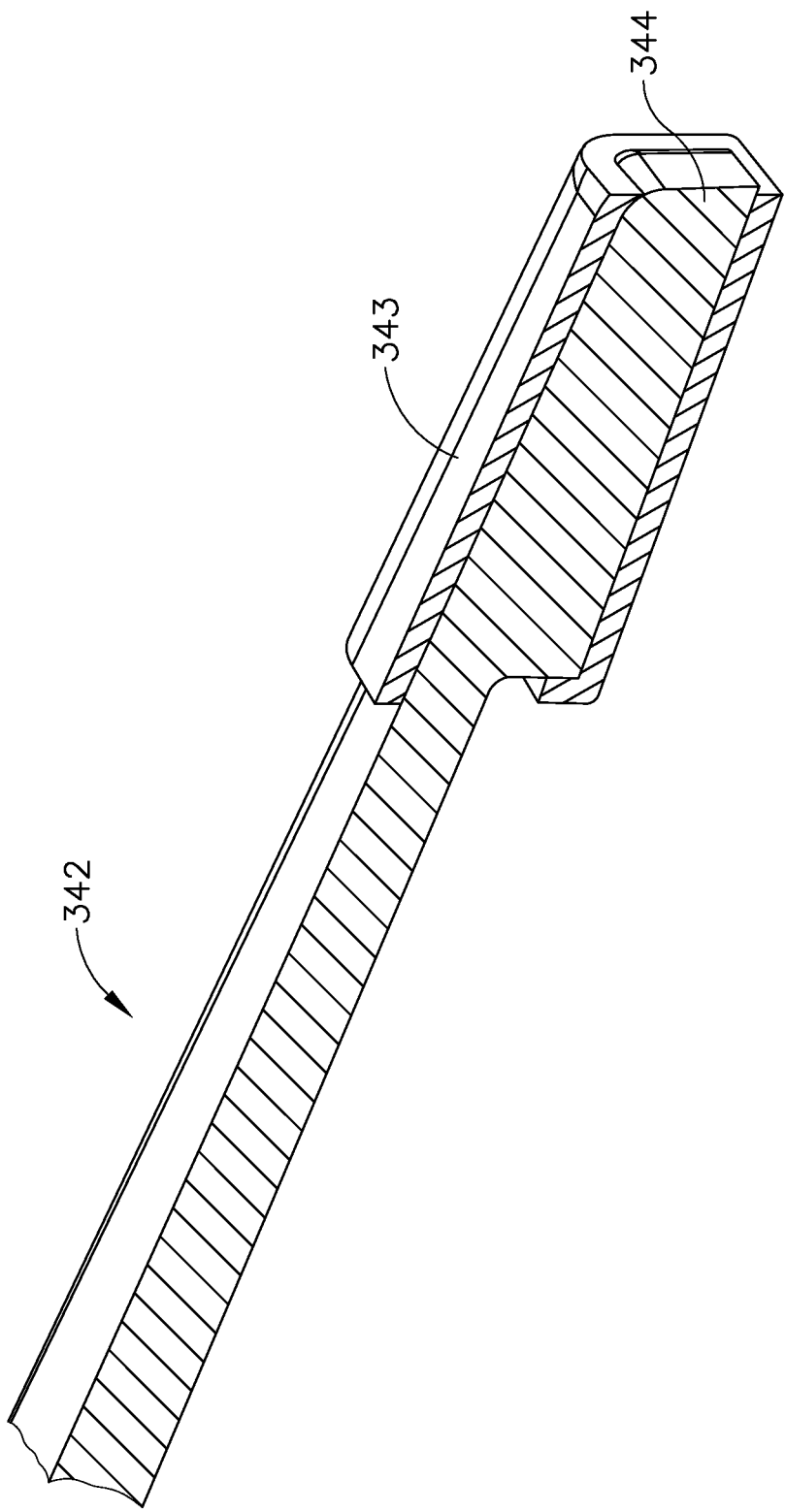
FIG. 24 depicts a cross-sectional view of the pad configuration of FIG. 22, with cross-section taken along line 24-24 of FIG. 22.

FIGS. 22 through 24 show an exemplary alternative passive tine (342). Passive tine (342) comprises similar features to that of passive tine (42) with certain exceptions noted below. In particular, passive tine (342) is shown as having a foot (344) shaped substantially the same as foot (44) of passive tine (42). In contrast to passive tine (42), passive tine (342) is configured with a low friction sleeve (343). As can be seen in FIG. 23, isolating sleeve is cylindrical in shape having an inner circumference smaller than the circumference of foot (44). Sleeve (343) may be comprised of a material having properties sufficient to permit sleeve (343) to stretch, and to provide low friction surface to passive tine (342) that may prevent tissue adhesion. During assembly, a stretching force may be applied to sleeve (343). While such a force is applied to sleeve (343), foot (344) of passive tine (342) may be inserted into sleeve (343). Subsequently, when the stretching force is removed, sleeve (343) may conform to the shape of foot (344).

Sleeve (343) may be comprised of any material suitable to provide a low friction surface and stretch around passive tine (342) such as PTFE/Teflon, rubber, or any other material having suitable properties. Additionally, if sleeve (343) is combined with an RF tine (e.g., similar to tine (240), above), the material of sleeve (343) may be suitable to conduct RF signals. For instance, a PTFE/Teflon sleeve (343) may be impregnated with electromagnetically conductive particles such that RF signals may flow therethrough. In other examples, PTFE/Teflon sleeve (343) may have plurality of openings filled with conductive gels or similar materials. In some other examples, sleeve (343) may comprise a carbon loaded PTFE/Teflon material or a high temperature PTC capable of conducting electric current.

FIG. 24 depicts passive tine (342) and sleeve (343) in cross section. As can be seen, sleeve (343) extends proximally past foot (344). In particular, the proximal extension of sleeve (343) permits sleeve (343) to wrap behind the proximal end/edge of foot (344). This aspect of sleeve (343) may provide sleeve (343) with additional longitudinal stability. It should be understood that such an extension is entirely optional, and may be omitted in other examples. Of course, other configurations and/or materials of sleeve (343) will be apparent to those of ordinary skill in the art in view of the teachings herein.

Figure 25:
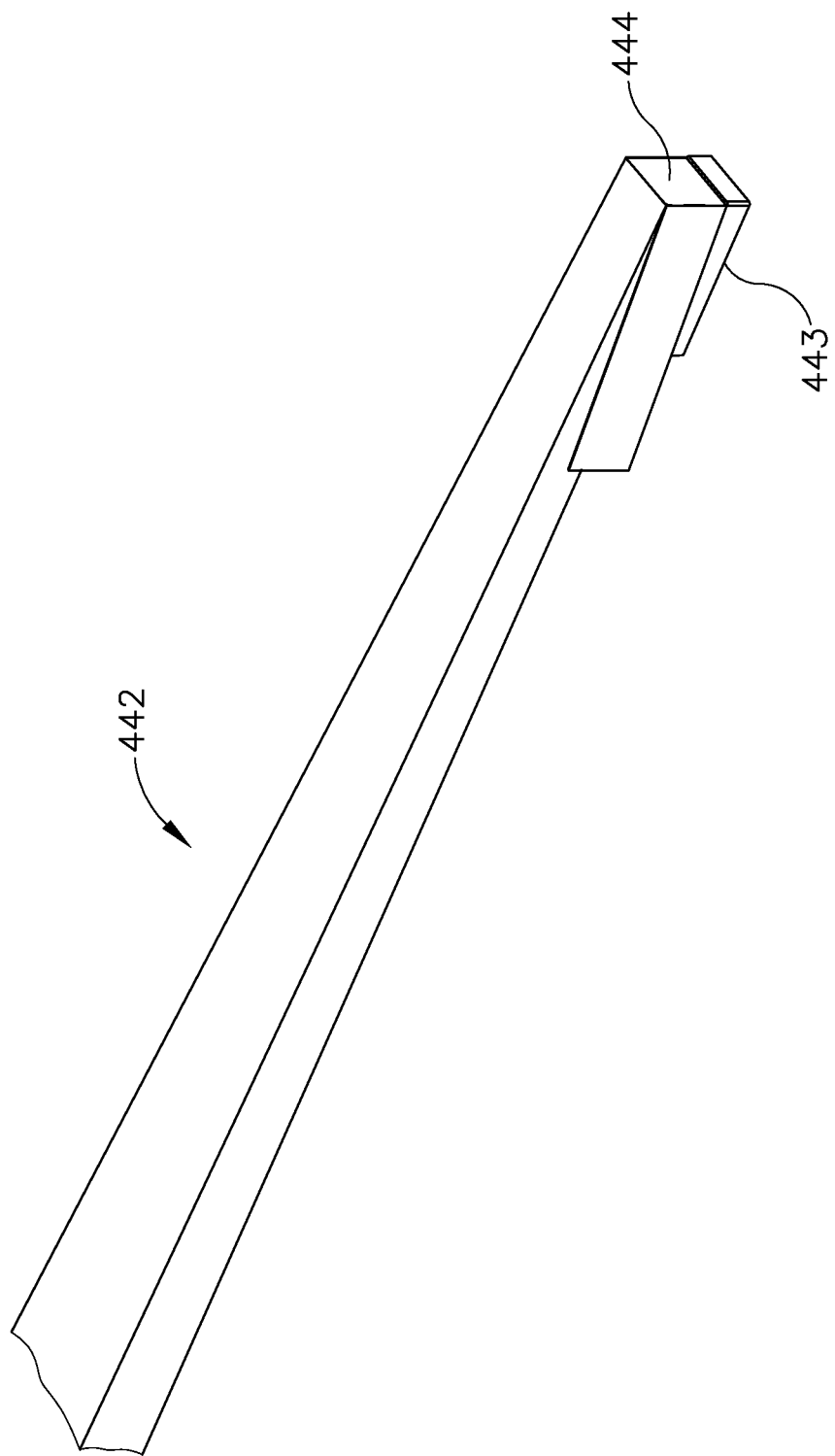
FIG. 25 depicts a perspective view of an exemplary alternative pad configuration that may be incorporated into the ultrasonic forceps of FIG. 1.

FIG. 25 depicts another exemplary alternative passive tine (442). Passive tine (442) is substantially the same as other passive tines (42, 342) discussed above with certain exceptions noted below. In particular, passive tine (442) comprises a foot (444) which is substantially similar to the feet (44, 344) described above. However, foot (444) of passive tine (442) has an isolating pad (443) attached thereto. Isolating pad (443) has the same principal function as sleeve (343) discussed above—to provide a low friction surface for passive tine (442) to resist tissue adhesion. As can be seen, however, isolating pad (443) is attached to passive tine (442) differently than sleeve (343). In particular, isolating pad (443) is fixedly secured to the bottom of foot (444). Isolating pad (443) may be fixedly secured to foot (444) by any suitable means such as adhesive bonding, ultrasonic welding, or the like.

Figure 26:
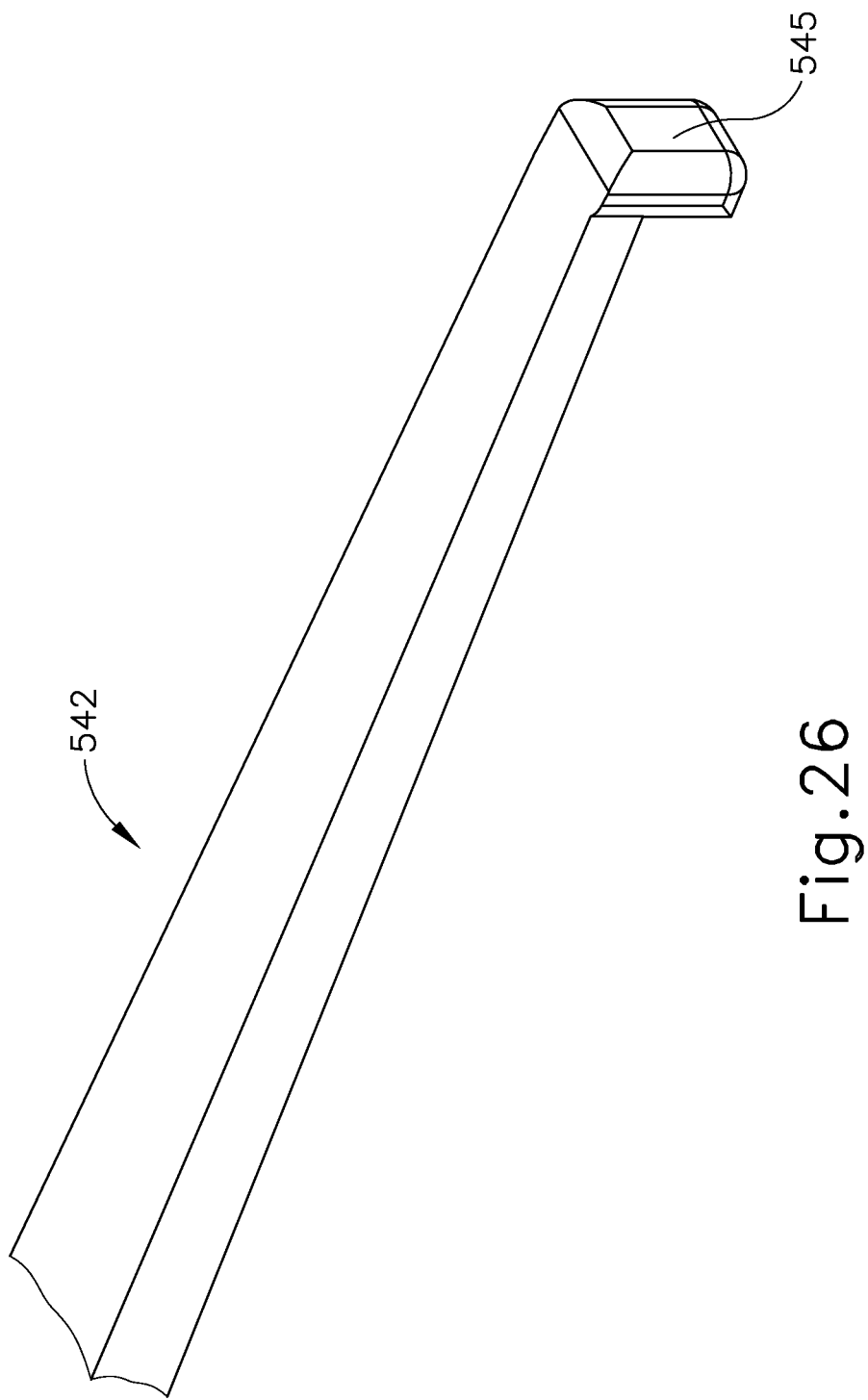
FIG. 26 depicts a perspective view of an exemplary alternative tine that may be incorporated into the ultrasonic forceps of FIG. 1.
Figure 27:
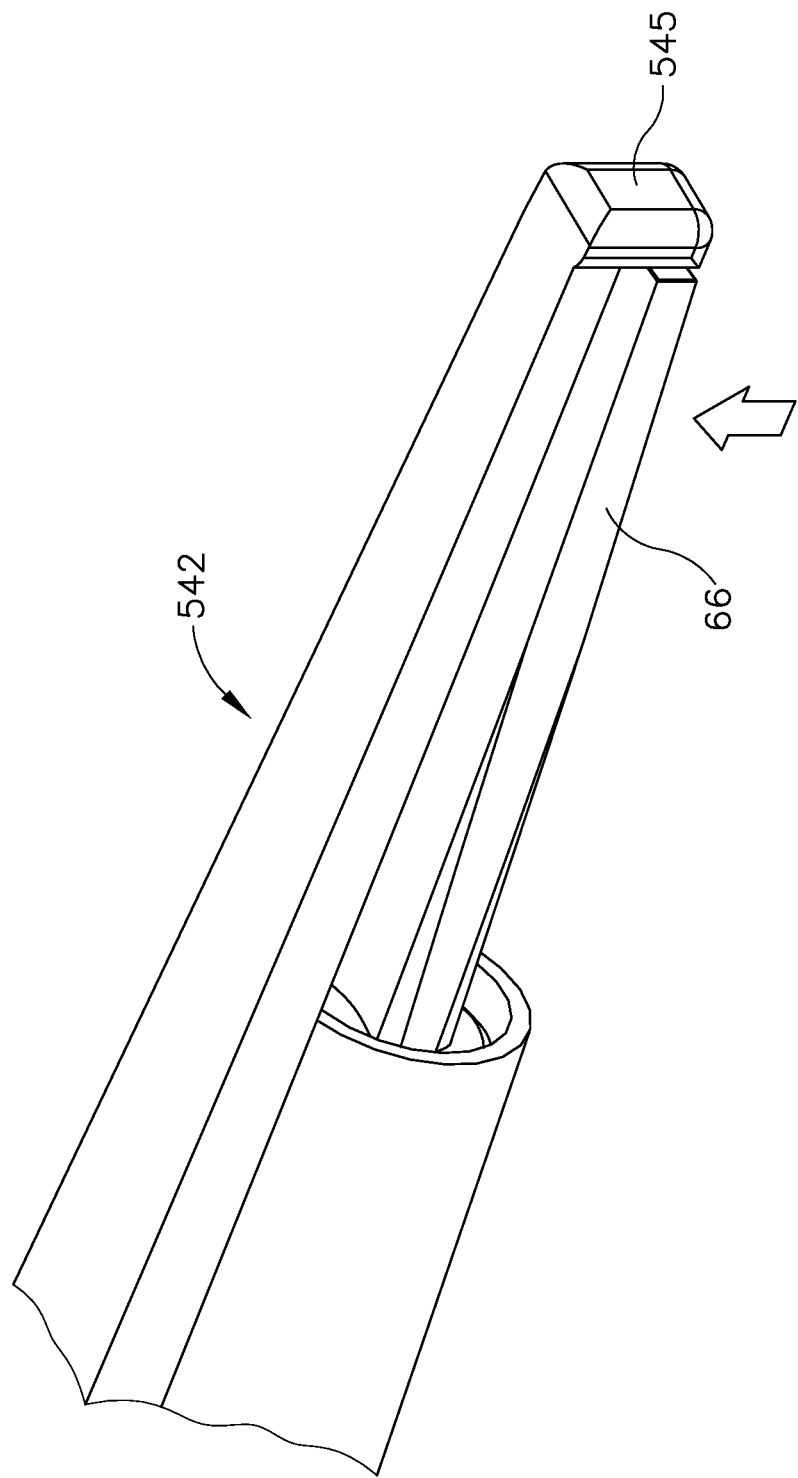
FIG. 27 depicts a perspective view of the tine of FIG. 26 in contact with an active tine.

FIGS. 26 and 27 show another exemplary alternative passive tine (542). Passive tine (542) is substantially the same as passive tines (42, 342, 442) discussed above except passive tine (542) is equipped with a transversely extending distal leg (545). As can be seen in FIG. 27, distal leg (545) may overlap the distal end of ultrasonic blade (66) when passive tine (542) is actuated by a user as described above. Distal leg (545) may operate to retain tissue during a surgical procedure. In other examples, passive tine (542) may be equipped with a variety of distal geometries corresponding to a particular surgical procedure and/or technique. Passive tine (542) may also include pads or sleeves (343, 443) as described above. Moreover, it should be understood that a plurality of passive tines (42, 342, 442, 542). May be used in conjunction with housing (220), described above, such that passive tines (42, 342, 442, 542) may be quickly swapped out for other passive tines (42, 342, 442, 542) in response to changes in surgical procedure or technique. Similarly, passive tine (42, 342, 442, 542) may be omitted entirely and active tine (46) may be used as a single cutter/dissector. Of course, other tines (42, 342, 442, 452) having different configurations, materials, and/or uses will be apparent to those of ordinary skill in the art in view of the teachings herein.

D. Exemplary Alternative Waveguide Assemblies

Figure 28:
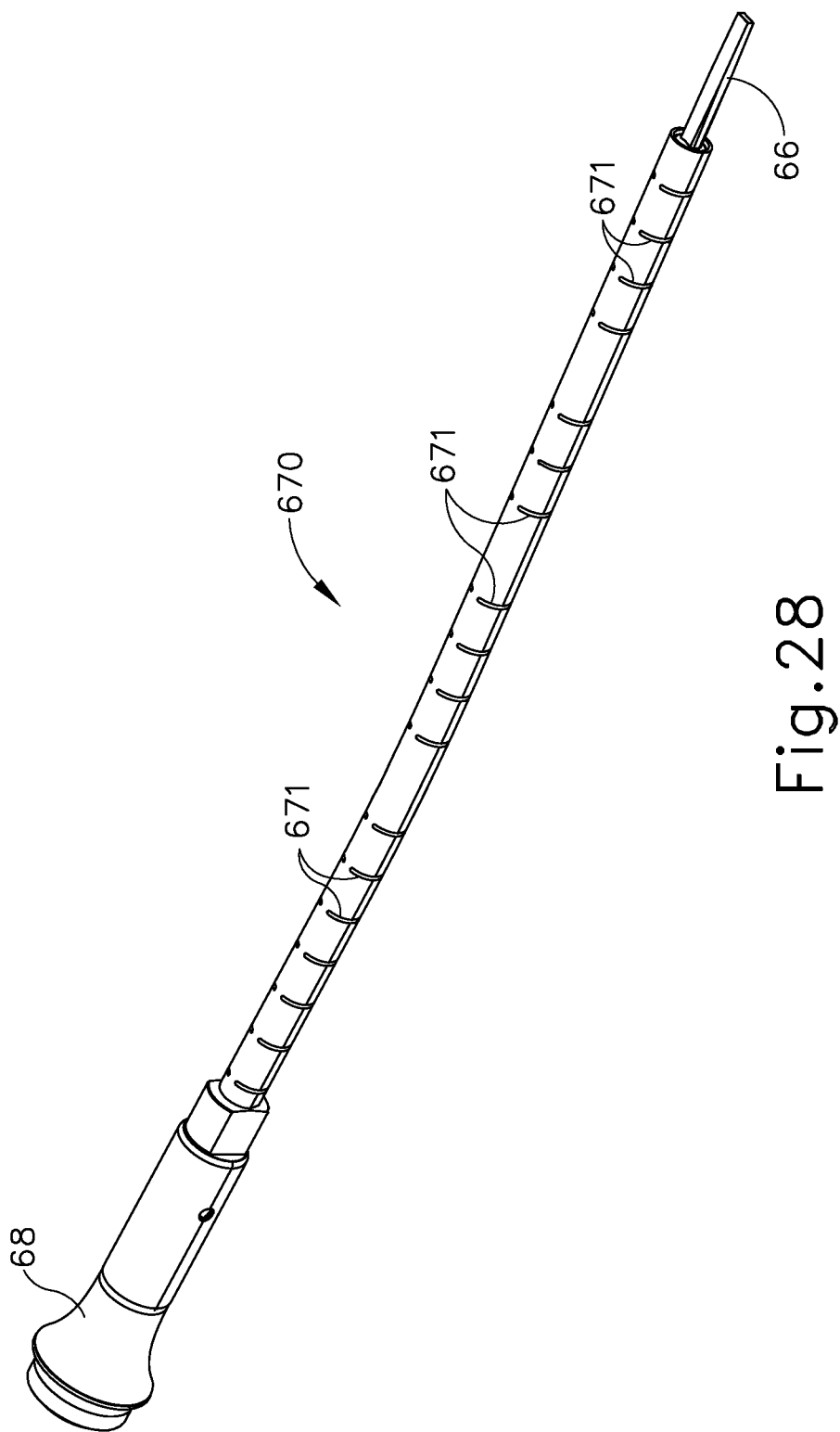
FIG. 28 depicts a perspective view of an exemplary alternative waveguide assembly that may be incorporated into the ultrasonic forceps of FIG. 1, having a slotted sheath.

FIG. 28 shows an exemplary alternative waveguide sheath (670) that may be used in conjunction with waveguide (78) of waveguide assembly (64). Waveguide sheath (670) is a single unitary sheath having a plurality of slots (671). Slots (671) are oriented along waveguide sheath (670) to permit waveguide sheath (670) to conform to the shape of waveguide (78). Sheath (670) may thus be particularly suited for versions of waveguide (78) that are curved (e.g., with a single curve, with a double curve or dogleg configuration, etc.). In particular, slots (671) may begin at the proximal end of sheath (670) and continue at to at least a point past any bends and/or curves in the waveguide (78). In such a configuration, waveguide (78) may be first attached to transducer (80) and then waveguide sheath (670) may be introduced onto waveguide (78) from the proximal end of waveguide sheath (670). In the present example, slots (671) are arranged along the length of waveguide sheath (670) in groups of slots (671) having consistent spacing. In such a configuration, spacing between slots (671) may increase at the longitudinal positions corresponding to nodes associated with ultrasonic vibrations communicated along waveguide (78), to permit waveguide sheath (670) to completely cover spacer rings (79) or seals of waveguide (78). It should be understood that this feature is merely optional and slots (671) may have variable or consistent spacing along waveguide sheath (670).

Although waveguide sheath (670) is shown as a substantially solid tube having slots (671) therein, it should be understood that in other versions waveguide sheath (670) may use something other than a tube-slot design. For instance, waveguide sheath (670) may comprise a flat helical spring extending the entire length of waveguide sheath (670). In such an example, slots (671) may be formed by the spaces between each rotation of the flat helical spring. Yet in other examples, the tube of waveguide sheath (670) may be combined with a flat helical spring. Like with waveguide sheath (70) discussed above, waveguide sheath (670) may be sealed to prevent fluid, tissue, or other substances from entering the space between waveguide sheath (670) and waveguide (78). Of course, this feature is merely optional and may be omitted entirely. It should also be understood that waveguide sheath (670) may include an outer covering such as a plastic cover, shrink wrap, and/or other kind of cover to prevent fluid and/or tissue from entering slots (671). Other configurations of waveguide sheath (670) will be apparent to those of ordinary skill in the art in view of the teachings herein.

Figure 29:
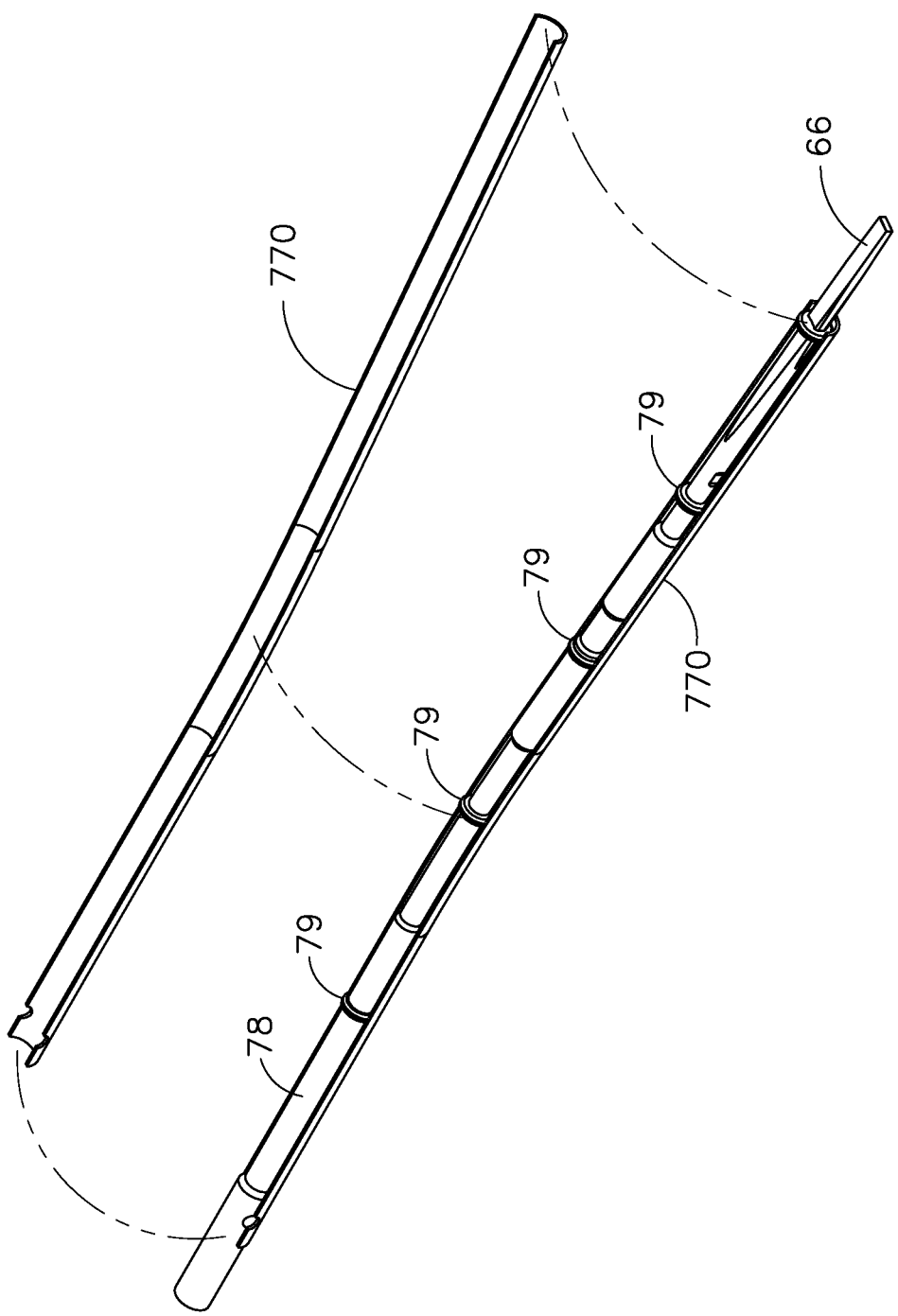
FIG. 29 depicts a partially exploded view of an exemplary alternative waveguide assembly that may be incorporated into the ultrasonic forceps of FIG. 1, having a clam shell sheath.
Figure 30:
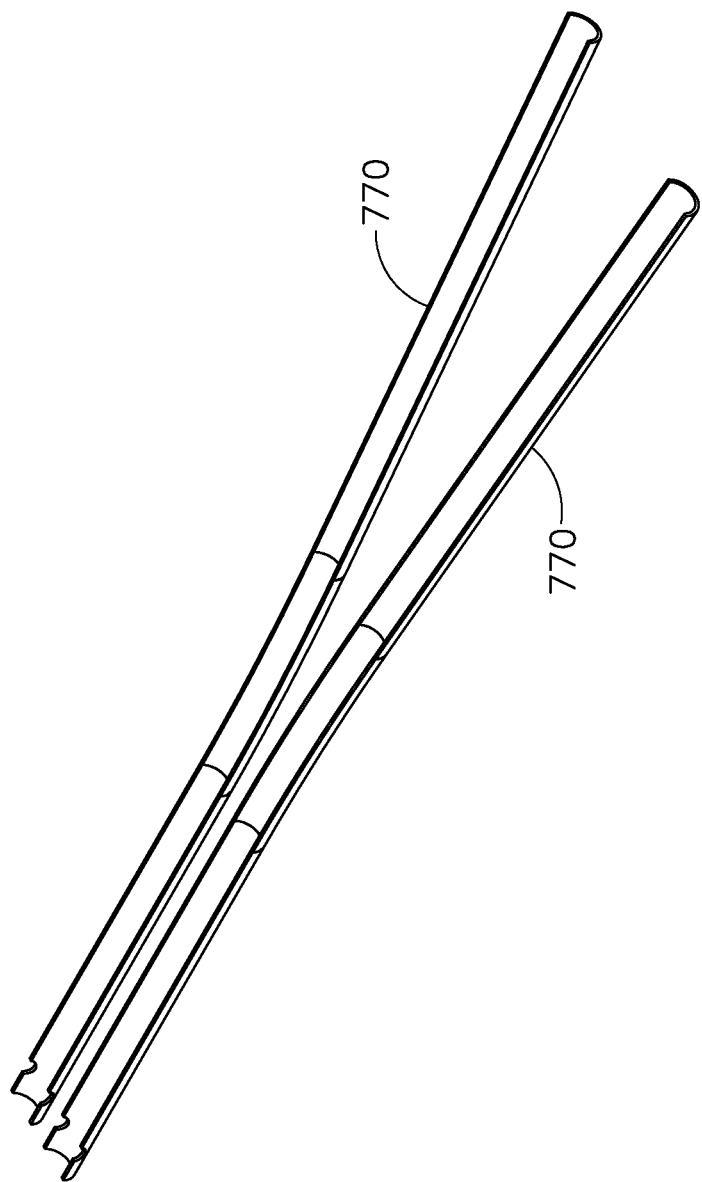
FIG. 30 depicts a perspective view of the clam shell sheath of FIG. 29.
Figure 31:
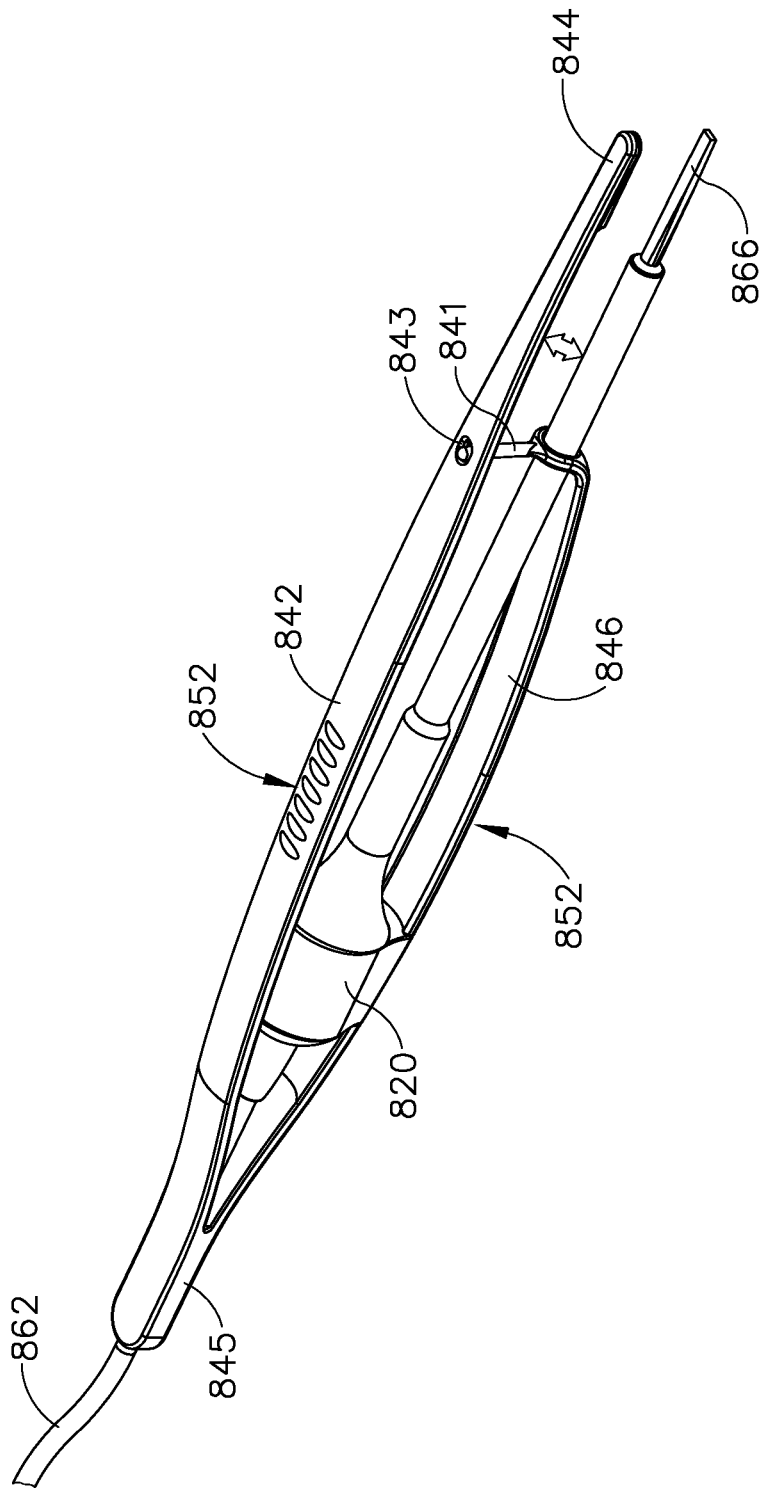
FIG. 31 depicts a perspective view of an exemplary alternative ultrasonic forceps.
Figure 34:
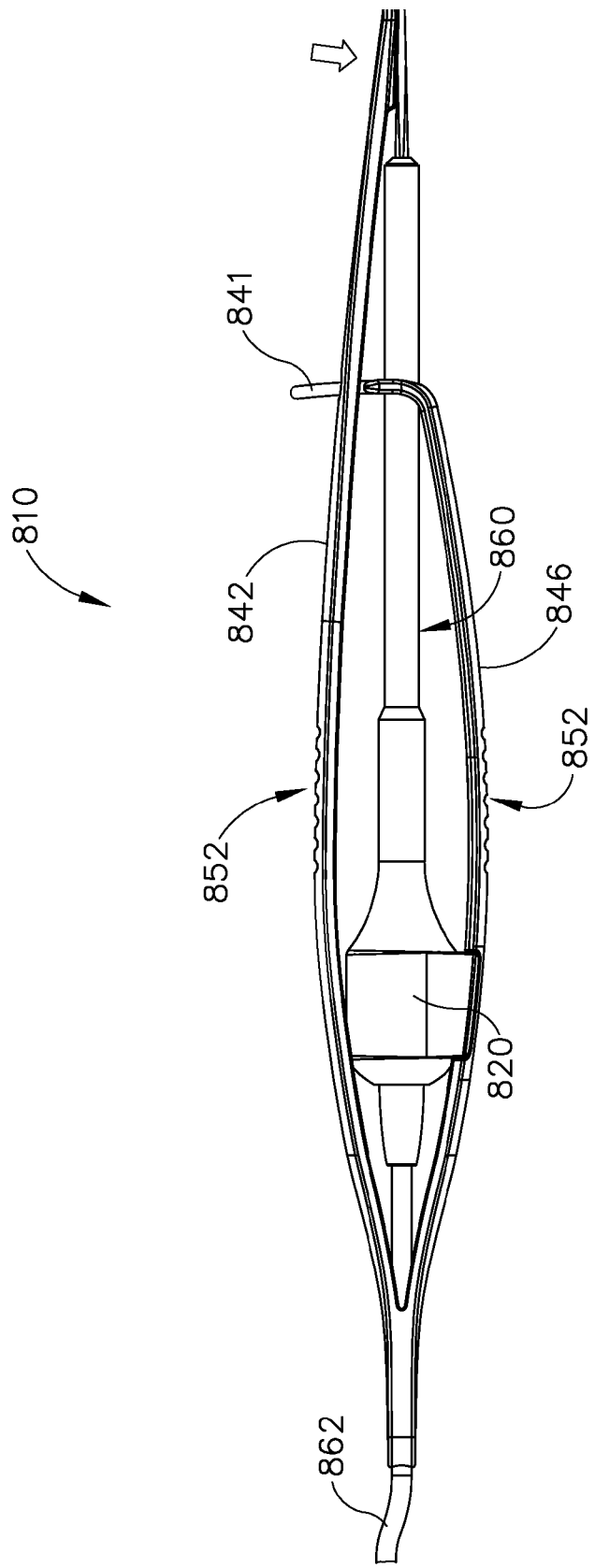
FIG. 34 depicts a side elevational view of the ultrasonic forceps of FIG. 31, with tines depressed.

FIGS. 29 and 30 show another exemplary alternative waveguide sheath (770). Waveguide sheath (770) is substantially the same as waveguide sheath (670), discussed above, except that waveguide sheath (770) is a substantially solid tube from proximal end to distal end. To accommodate any bend and/or curve in waveguide (78), waveguide sheath (770) is divided in half longitudinally. Thus, each half of waveguide sheath (770) may be placed on waveguide (78) and then each half of waveguide sheath (770) may be fixedly secured to the other. Each half of waveguide sheath (770) may be fixedly secured to the other by any suitable means such as ultrasonic welding, laser welding, adhesive bonding, or the like. Other suitable configurations of waveguide sheaths (670, 770) will be apparent to those of ordinary skill in the art.

III. Exemplary Alternative Ultrasonic Forceps Configurations

To the extent that any of the examples discussed below are shown and described in the context of a variation of one particular kind of forceps (10, 810, 910, 1010, 1110, 1210, 1310, 1410, 1510), it should be understood that the same teachings may be readily applied to the other kind of forceps (10, 810, 910, 1010, 1110, 1210, 1310, 1410, 1510). Each example described below should therefore not be viewed as only having applicability to either forceps (10), forceps (810), forceps (910), forceps (1010), forceps (1110), forceps (1210), forceps (1310), forceps (1410), or forceps (1510). Furthermore, it is contemplated that the teachings below may be readily applied to other kinds of surgical instruments, not just the variations of forceps (10, 810, 910, 1010, 1110, 1210, 1310, 1410, 1510).

FIGS. 31 through 34 show an exemplary alternative ultrasonic forceps (810) having a substantially straight configuration. Forceps (810) is substantially the same as forceps (10) having similar elements and functionality with certain expectations noted below. Forceps (810) comprises a housing (820), a pair of tines (842, 846) with grasping regions (852), an acoustic assembly (860) and a cable (862). Unlike housing (20) of forceps (10), housing (820) is configured to fit between tines (842, 846) rather than being offset. Similarly, tines (842, 846) and acoustic assembly (860) extend distally, along a straight longitudinal axis, without having a curve or a bend in contrast to tines (42, 46) and acoustic assembly (60) of forceps (10).

As can best be seen in FIG. 32, housing (820) may attach to one tine (846) and act as a pivot point (823) for another tine (842). Unlike housing (20) of forceps (10), housing (820) does not couple each tine (842, 846) together. Instead, the proximal end of each tine (842, 846) attaches to the other via an attachment region (845). Although tines (842, 846) are shown as being of integral construction, such that each tine (842, 846) extends proximally from a single proximal end, it should be understood that no such limitation is intended. Indeed, in other examples tines (842, 846) may be separate components, but yet have their proximal ends secured to one another by any suitable means such as welding, mechanical fastening, adhesive bonding, or the like.

Tines (840) may also be configured with a hole on the proximal end, through which cable (862) may be supported. Cable (862) may then be used to couple acoustic assembly (860) to the generator. The generator may have similar functionality and operational characteristics as the generator described above.

Like tine (42), tine (842) may be resiliently biased to maintain a gap between a foot (844) and an ultrasonic blade (866), but is bendable to drive foot (844) with a tissue pad toward ultrasonic blade (866). To maintain alignment of tines (842, 846) relative to acoustic assembly (860) along a consistent closure plane as foot (844) travels toward ultrasonic blade (866), tine (846) of the present example comprises a guide post (841). Tine (842) includes an opening (843) configured to receive guide post (841). Thus, as tine (842) is deformed and moved toward acoustic assembly (860), guide post (841) and opening (843) work cooperatively to maintain alignment of tines (842, 846) with acoustic assembly (860) along a consistent closure plane. Post (841) and opening (843) thus ensure alignment of foot (844) and ultrasonic blade (866) along the pivot/closure plane. Other configurations of forceps (810) incorporating elements of the various examples described above will be apparent to those of ordinary skill in the art in view of the teachings herein.

Figure 35:
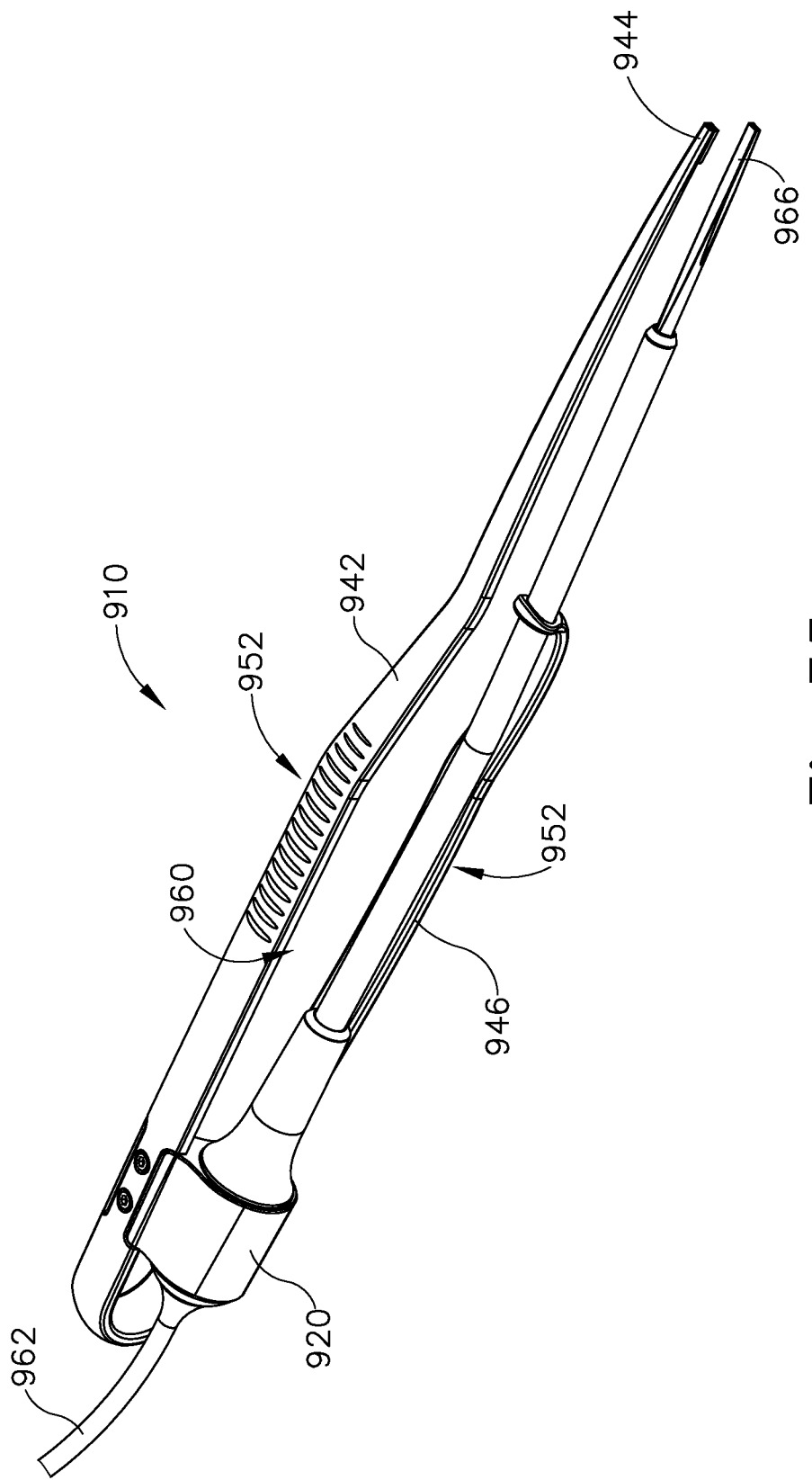
FIG. 35 depicts a perspective view of an exemplary alternative ultrasonic forceps.
Figure 36:
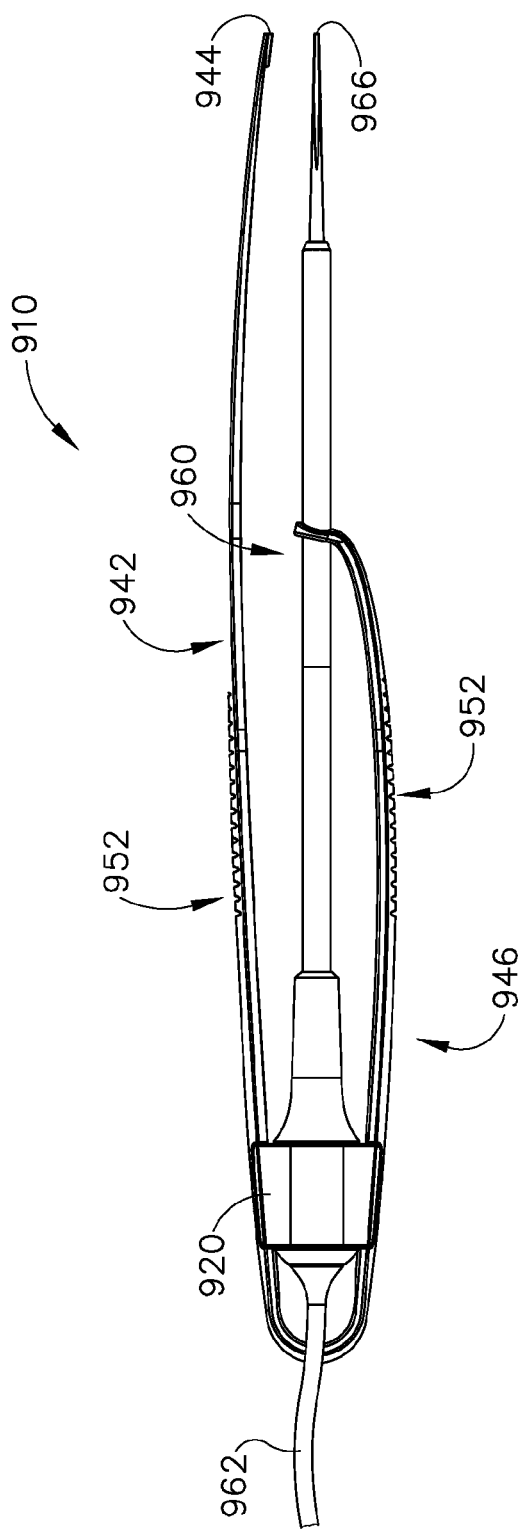
FIG. 36 depicts a side elevational view of the ultrasonic forceps of FIG. 35.
Figure 37:
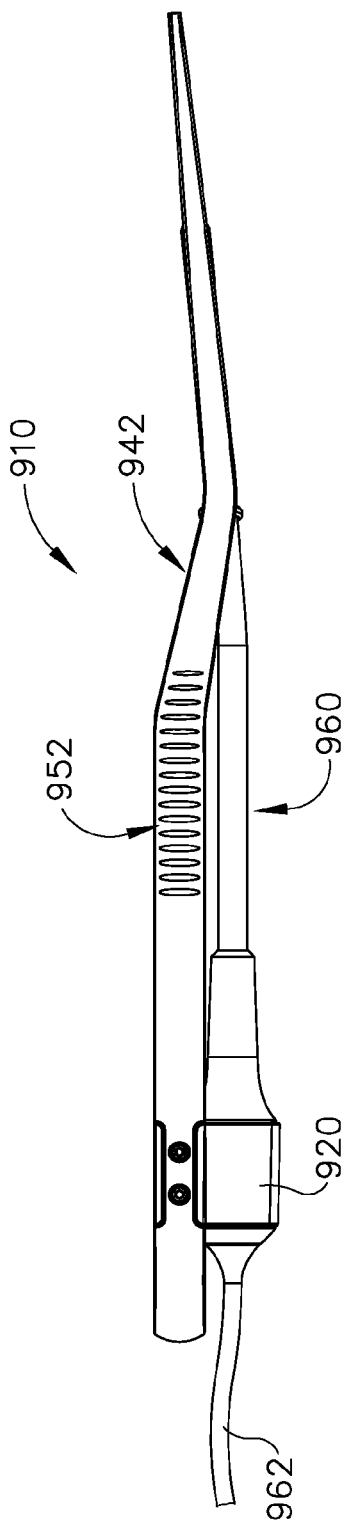
FIG. 37 depicts a top plan view of the ultrasonic forceps of FIG. 35.
Figure 42:
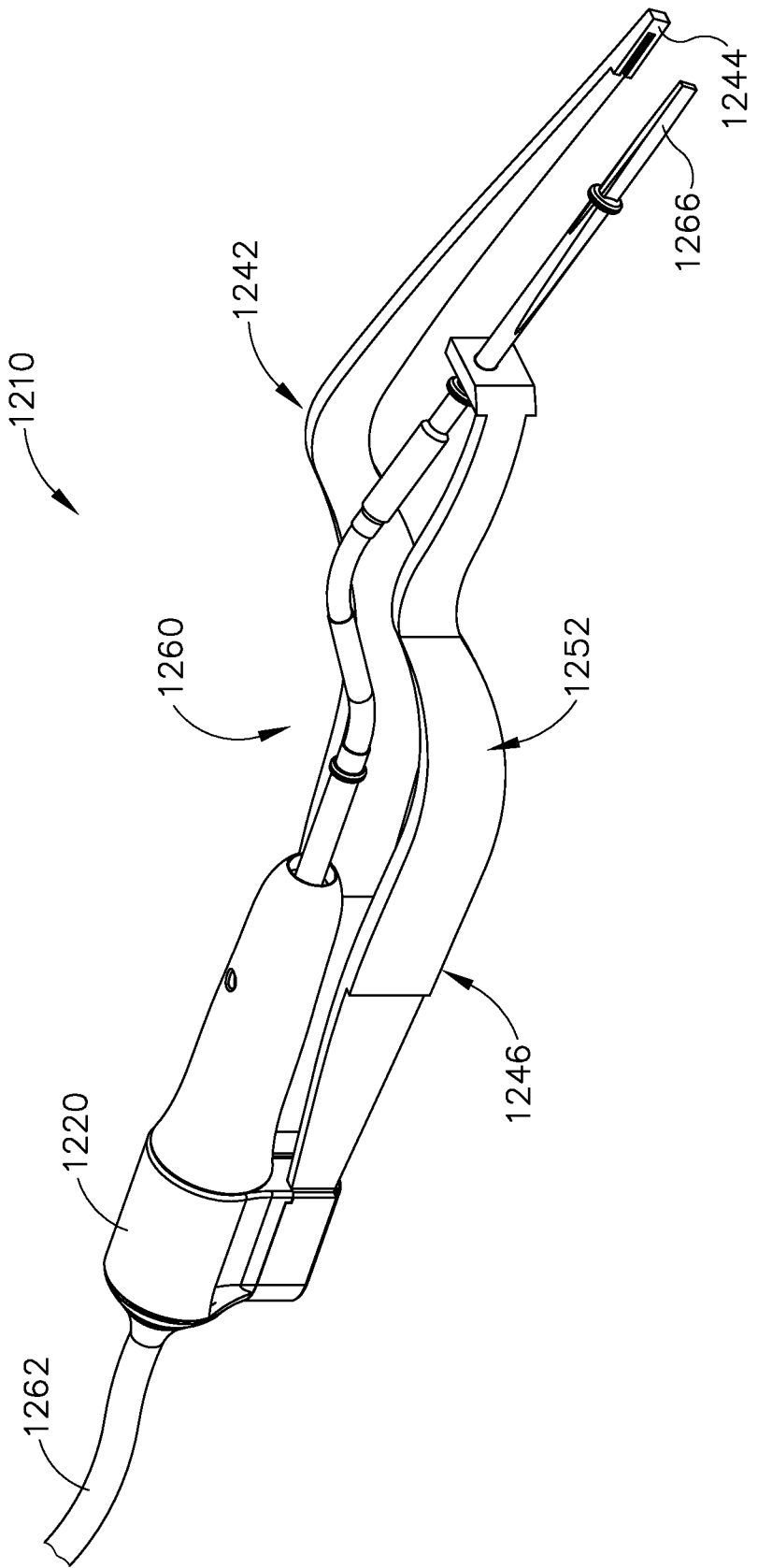
FIG. 42 depicts a perspective view of an exemplary alternative ultrasonic forceps having a two bend waveguide.
Figure 43:
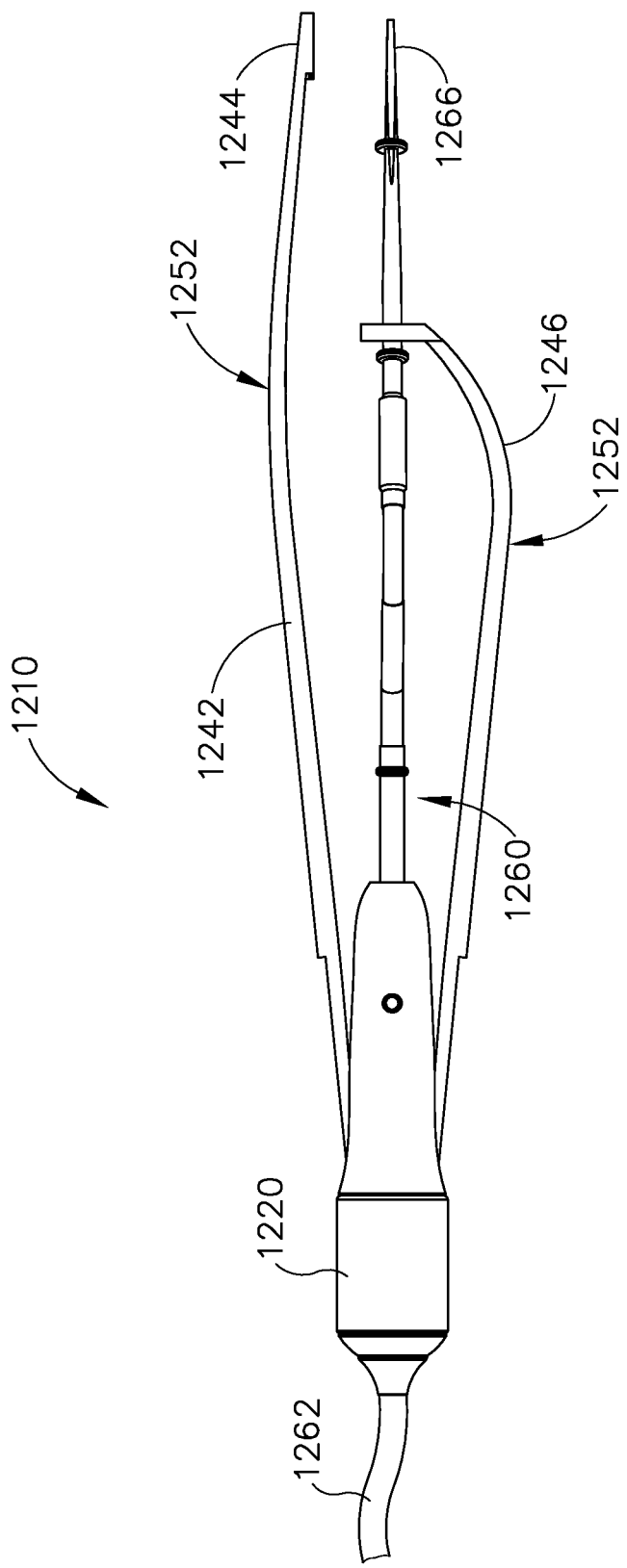
FIG. 43 depicts a top plan view of the ultrasonic forceps of FIG. 42.
Figure 44:
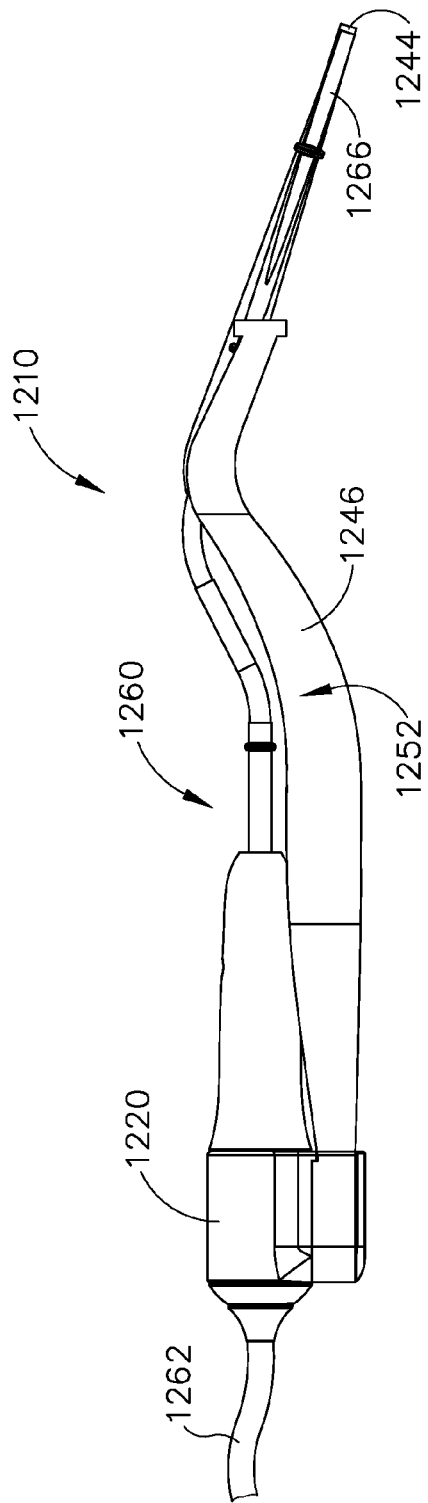
FIG. 44 depicts a side elevational view of the ultrasonic forceps of FIG. 42.
Figure 45:
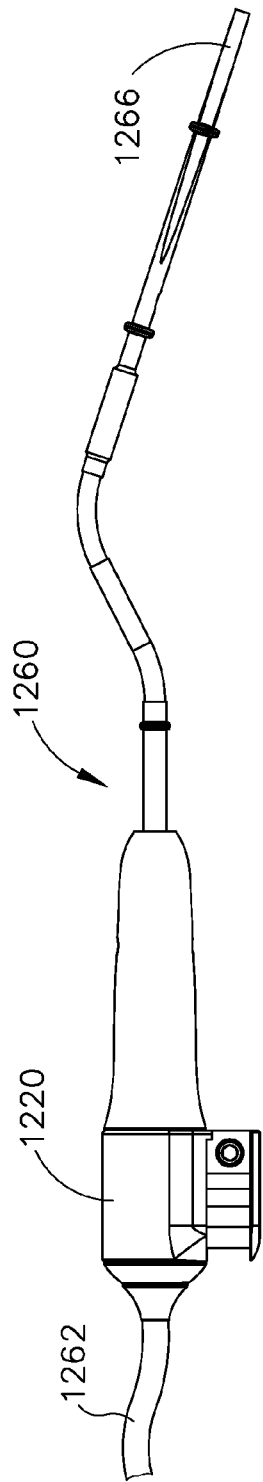
FIG. 45 depicts a side elevational view of the ultrasonic forceps of FIG. 42, with tines removed.

FIGS. 35 through 37 show another exemplary alternative ultrasonic forceps (910). Forceps (910) is substantially the same as forceps (10, 810) having similar elements and functionality with certain exceptions noted below. Forceps (910) comprises a housing (920), a pair of tines (942, 946) with grasping regions (952), an acoustic assembly (960) and a cable (962). Like tine (42), tine (942) is resiliently biased to maintain a gap between a foot (944) and an ultrasonic blade (966), but is bendable to drive foot (944) with a tissue pad toward ultrasonic blade (966). Forceps (910) combines elements of forceps (10) and forceps (810) to create a hybrid between the two. For instance, as in forceps (10), housing (920) attaches to, and is offset from, both tines (942, 946). However, housing (920) in this configuration may act as a force regulating member for tines (942, 946), rather than merely providing alignment and support for tines (942, 946). For instance, the position of housing (920) along the length of tine (942) may restrict the force with which foot (944) may compress tissue against blade (966), by effectively defining the bending length of tine (942). Positioning housing (920) further distally along tine (942) may decrease the force with which foot (944) may compress tissue against blade (966); while positioning housing (920) further proximally along tine (942) may increase the force with which foot (944) may compress tissue against blade (966).

Additionally, as in forceps (10), tines (942, 946) and acoustic assembly (960) are bent or curved for ergonomic grip and to maximize surgical site visibility. On the other hand, like forceps (810), the proximal end of each tine (942, 946) integrally connects to the other. The proximal end of each tine (942, 946), however, curves relative to the other to integrally connect. Tines (942, 946) thus together form a unitary structure in this example. Other examples of forceps (910) incorporating elements of the various examples described above will be apparent to those of ordinary skill in the art in view of the teachings herein.

FIGS. 38 and 39 show another exemplary alternative ultrasonic forceps (1010). Similar to forceps (810, 910) discussed above, forceps (1010) has similar elements and functionally as seen above with forceps (10). In particular, forceps (1010) comprises housing (1020), a pair of tines (1042, 1046) with grasping regions (1052), an acoustic assembly (1060), and a cable (1062). Unlike housing (20, 820, 920), housing (1020) is integrated into forceps (1042, 1046). Similarly, acoustic assembly (1060) is integrated into one tine (1046), and includes a waveguide that is curved, following the curved path of tine (1046). Accordingly, one tine (1046) may act as a pivot for the other tine (1042), thus allowing housing (1020) and acoustic assembly (1060) to pivot, moving a foot (1044) with a tissue pad toward an ultrasonic blade (1066). Of course, other examples of forceps (1010) incorporating elements of the various examples described above will be apparent to those of ordinary skill in the art in view of the teachings herein.

FIGS. 40 and 41 show another exemplary alternative ultrasonic forceps (1110). Forceps (1010) is substantially the same as forceps (10, 810, 910, 1010) having similar elements and functionality with certain exceptions noted below. Forceps (1110) comprises a housing (1120), a pair of tines (1142, 1146) with grasping regions (1152), an acoustic assembly (1160) and a cable (1162). Forceps (1110) is similar to forceps (910) in that it combines elements of forceps (10) and forceps (810) to create a hybrid between the two. For instance, like forceps (10), housing (1120) is offset from both tines (1142, 1146). Additionally, like forceps (10), tines (1142, 1146) are bent or curved for ergonomic grip and to maximize surgical site visibility. On the other hand, like forceps (810), only a single tine (1142, 1146) is attached to housing. Similarly, acoustic assembly (1160) extends distally without having a bend or curve. Also like forceps (810), the proximal end of each tine (1142, 1146) integrally connects to the other. The proximal end of each tine (1142, 1146), however, curves relative to the other to integrally connect. Tines (1142, 1146) thus together form a unitary structure in this example.

Housing (1120) is also positioned such that it does not restrict the movement of tine (1142) as tine (1142) pivots from its resiliently biased position urging a foot (1144) toward an ultrasonic blade (1160). Similar to tines (842, 846), tines (1142, 1146) are equipped with a guide post (1141) and an opening (1143) configured to receive guide post (1141). As noted above with forceps (810), this feature maintains longitudinal alignment of tines (1142, 1146) relative to acoustic assembly (1160) as tines (1142, 1146) transition between an open configuration and a closed configuration. Other examples of forceps (1110) incorporating elements of the various examples described above will be apparent to those of ordinary skill in the art in view of the teachings herein.

FIGS. 42-45 show another exemplary alternative ultrasonic forceps (1210). Forceps (1210) is substantially the same as forceps (10, 810, 910, 1010, 1110) having similar elements and functionality with certain expectations noted below. Forceps (1210) comprises a housing (1220), a pair of tines (1242, 1246) with grasping regions (1252), an acoustic assembly (1260) and a cable (1262). Housing (1220) is offset from tines (1242, 1246) which wrap around housing (1220) and may be fixedly secured thereto. Like tine (42), tine (1242) is resiliently biased to maintain a gap between a foot (1244) and an ultrasonic blade (1266), but is bendable to drive foot (1244) with a tissue pad toward ultrasonic blade (1266). Similar to tines (42, 46) and acoustic assembly (60) of forceps (10), tines (1242, 1246) and acoustic assembly (1260) are bent or curved. However, unlike tines (42, 46) and acoustic assembly (60), tines (1242, 1246) and acoustic assembly (1260) have two bends or curves. Additionally, instead of each tine (1242, 1246) being separately secured to housing, each tine (1242, 1246) curves around housing (1220) and integrally connects to the other. Of course, other configurations of forceps (1210) incorporating elements of the various examples described above will be apparent to those of ordinary skill in the art in view of the teachings herein. It should also be understood that a waveguide sheath is omitted from FIGS. 42-45 for clarity. Some versions of forceps (1210) may include a sheath about the waveguide of acoustic assembly (1260) (e.g., to provide protection to the waveguide and/or acoustic isolation relative to the operator's hand, etc.).

Figure 46:
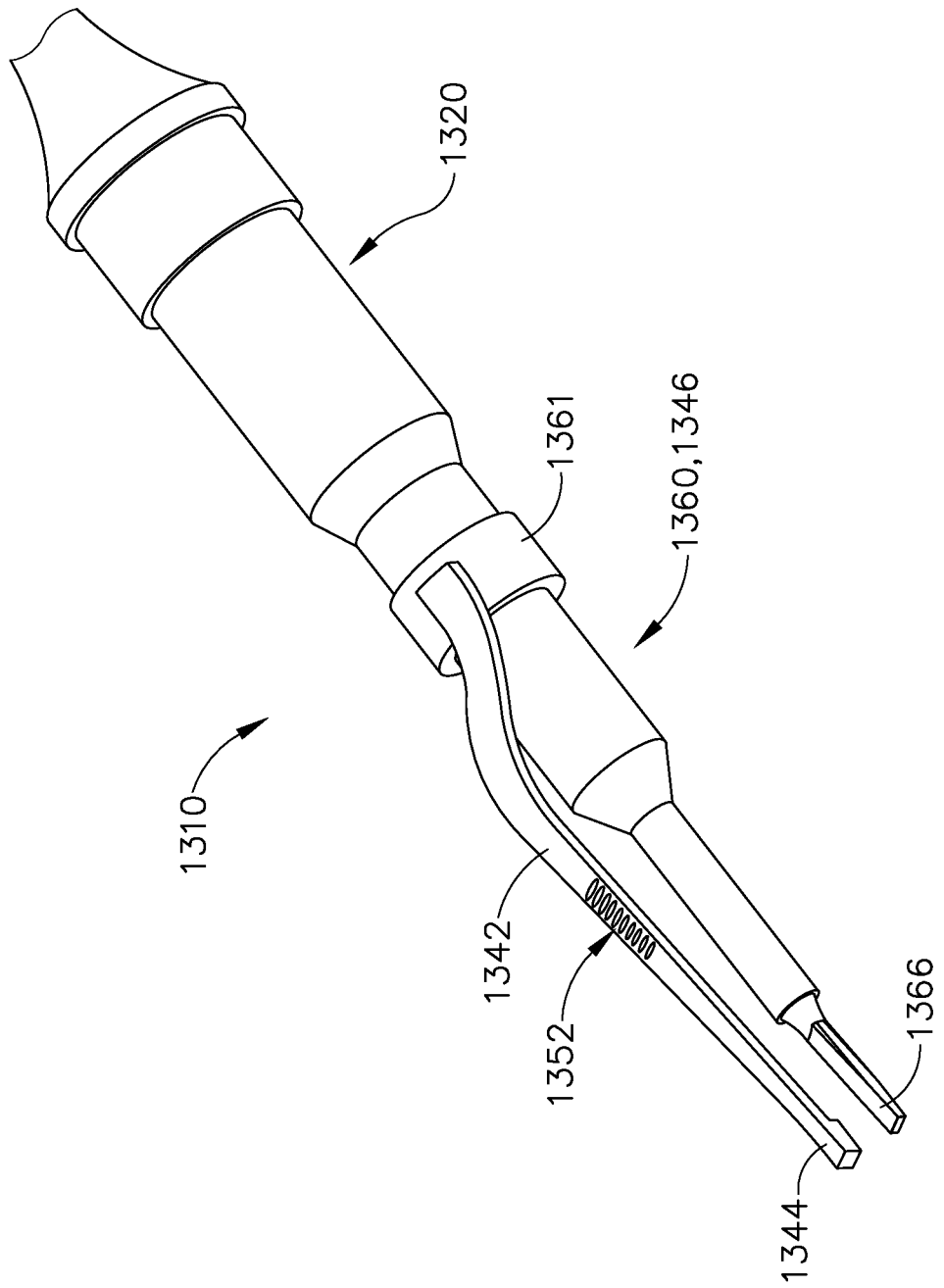
FIG. 46 depicts a perspective view of an exemplary alternative ultrasonic forceps having a passive tine attached to a collar.

FIG. 46 shows another exemplary alternative ultrasonic forceps (1310). Forceps (1310) is substantially the same as forceps (10, 810, 910, 1010, 1110, 1210) having similar elements and functionality with certain expectations noted below. Forceps (1310) comprises a housing (1320), a tine (1342), an acoustic assembly (1360) and a cable (not shown). Tine (1342) includes a gripping feature (1352). Like tine (42), tine (1342) is resiliently biased to maintain a gap between a pad (1343) and a blade (1366), but is bendable to drive pad (1343) toward blade (1366). Unlike forceps (10, 810, 910, 1010, 1110, 1210) discussed above, forceps (1310) has a single tine (1342) while acoustic assembly (1360) acts as a second tine (1346). Acoustic assembly (1360) extends distally without having a curve and/or bend. Moreover, housing (1320) does not connect tine (1342) to acoustic assembly (1360). Instead, acoustic assembly (1360) includes a collar (1361), which provides a structure for securing tine (1342) to acoustic assembly (1360). Tine (1340) may be fixedly secured to collar (1361) by any suitable means such as welding, adhesive bonding, mechanical fastening or the like.

In some versions, blade (1366) has a non-circular cross-sectional profile. In addition or in the alternative, blade (1366) may have a cross-sectional profile that is asymmetric. In either kind of versions, collar (1361) may be rotatable about the longitudinal axis of acoustic assembly (1360), thereby providing orbital movement of tine (1342) and pad (1343) about the longitudinal axis of acoustic assembly (1360). Such selective orbital positioning may enable a pad (1343) to be driven toward different geometrical features of a blade (1366) (e.g., toward a flat surface of blade, toward a sharp edge of blade, etc.). Thus, collar (1361) may be rotated to provide different orbital orientations of pad (1343) relative to blade (1366), corresponding to different modes of operation (e.g., sharp edge for mechanical cutting, flat surface for ultrasonic cutting or tissue sealing, etc.). Other configurations of forceps (1310) incorporating elements of the various examples described above will be apparent to those of ordinary skill in the art in view of the teachings herein.

Figure 47:
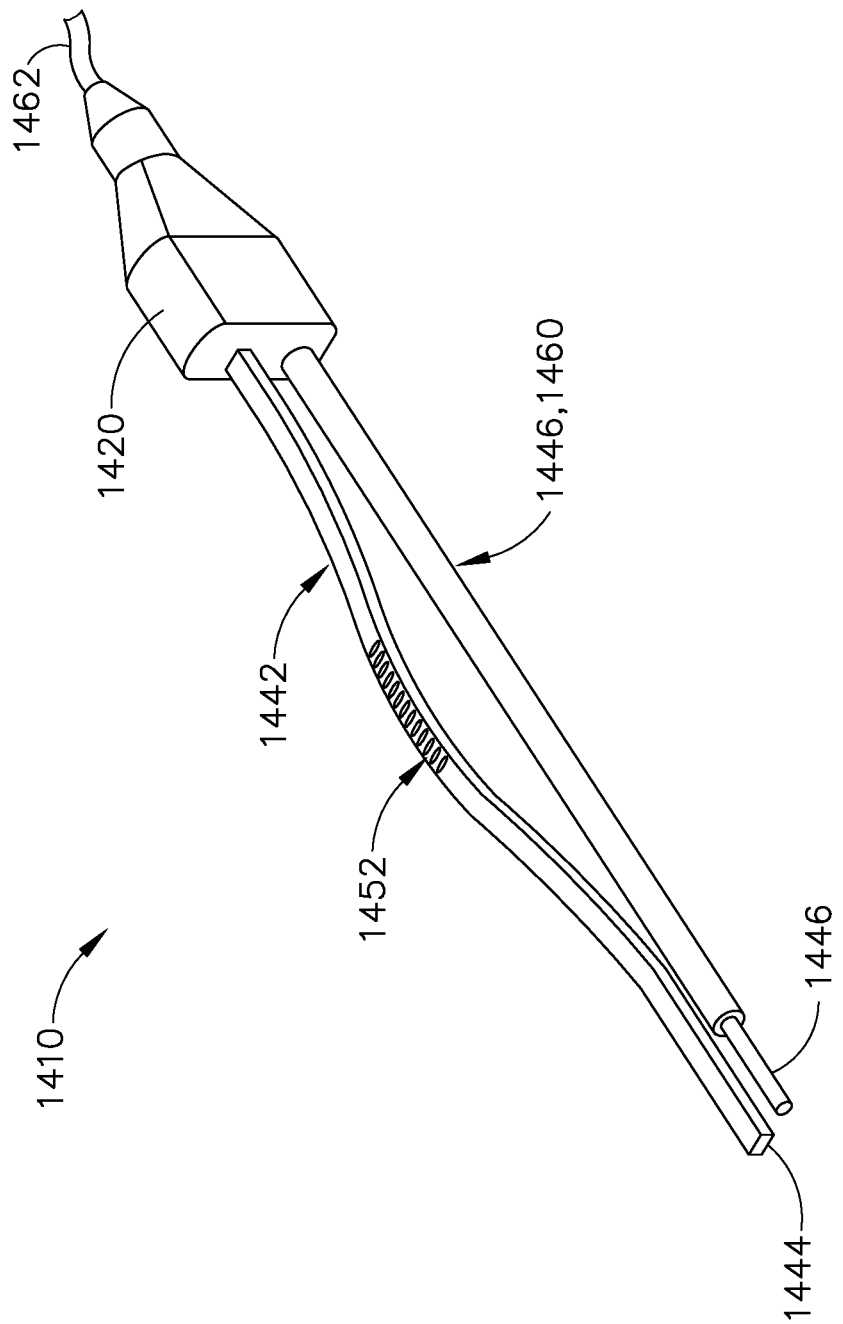
FIG. 47 depicts a perspective view of an exemplary alternative ultrasonic forceps.
Figure 49:
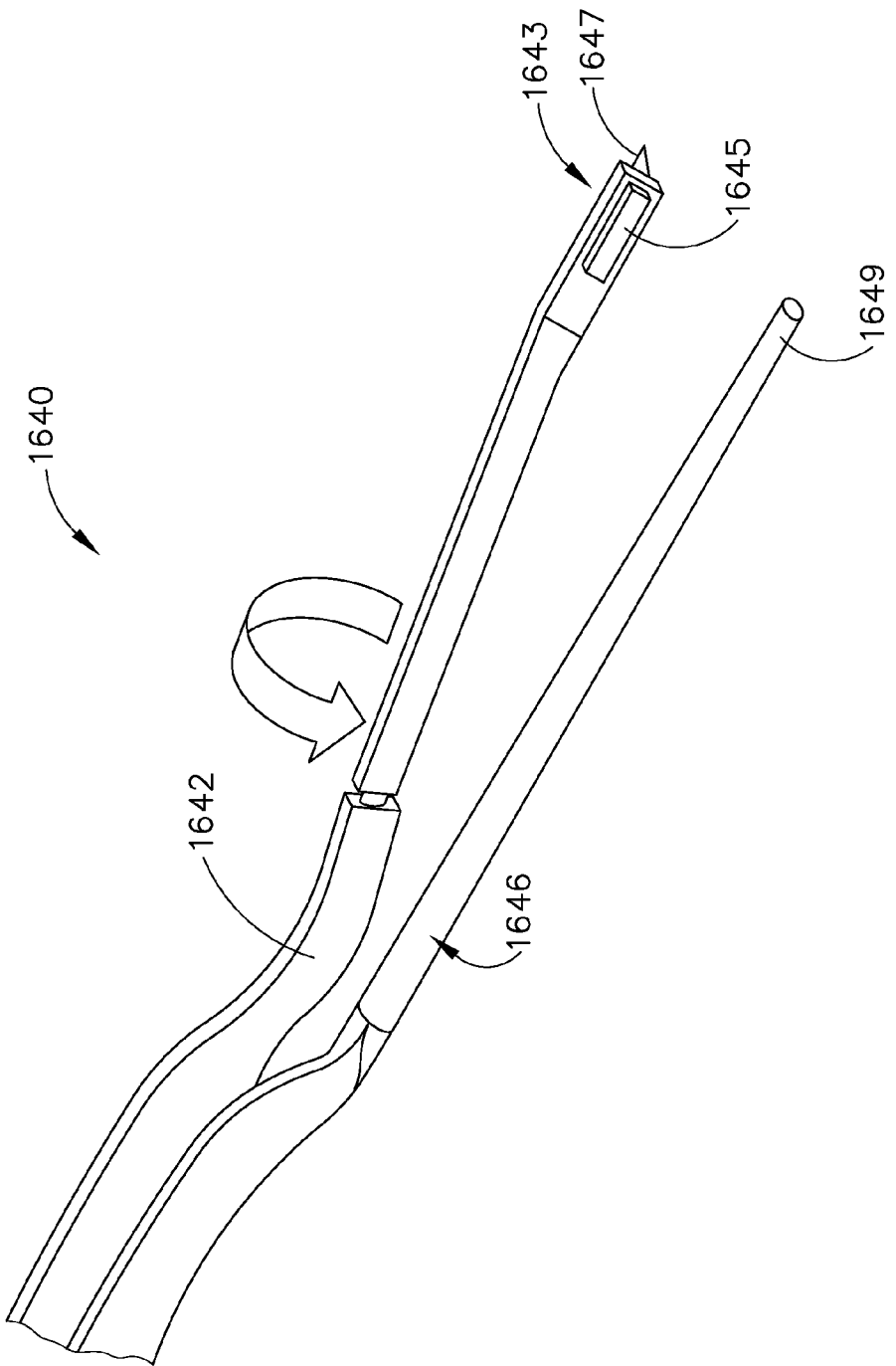
FIG. 49 depicts a perspective view of an exemplary alternative set of tines including a rotatable passive tine.

FIG. 47 shows another exemplary alternative ultrasonic forceps (1410). Forceps (1410) is substantially the same as forceps (10, 810, 910, 1010, 1110, 1210, 1310) having similar elements and functionality with certain expectations noted below. Forceps (1410) comprises a housing (1420), a tine (1442, 1446), an acoustic assembly (1460) and a cable (1462). Like with forceps (1310), forceps (1410) has a single tine (1442) with acoustic assembly (1460) acting as an active tine (1446). Tine (1442) includes a gripping feature (1452). Both tine (1442, 1446) and acoustic assembly (1460) are fixedly secured to housing (1420) and extend distally therefrom. Tine (1442) is resiliently biased to maintain a gap between a foot (1444) and an ultrasonic blade (1466), but is bendable to drive foot (1444) with a tissue pad toward ultrasonic blade (1466). A transducer (not shown) may be integrated into housing (1420) to provide ultrasonic vibrations to acoustic assembly (1460). Of course, other examples of forceps (1410) incorporating elements of the various examples described above will be apparent to those of ordinary skill in the art in view of the teachings herein.

FIGS. 48A and 48B show another exemplary alternative ultrasonic forceps (1510). Forceps (1510) is substantially the same as forceps (10, 810, 910, 1010, 1110, 1210, 1310, 1410) having similar elements and functionality with certain expectations noted below. Forceps (1510) comprises a housing (1520), a pair of tines (1542, 1546) with grasping regions (1552), an acoustic assembly (1560) and a cable (1562). Like with housing (1420) of forceps (1410), housing (1510) has tines (1542, 1546) and acoustic assembly (1560) fixedly secured thereto and extending distally therefrom. Also like housing (1420), housing (1520) has a transducer (1580) integrated therein. However, unlike forceps (1410), forceps (1510) comprise two tines (1542, 1546). Tine (1542) is resiliently biased to maintain a gap between a foot (1544) and an ultrasonic blade (1566), but is bendable to drive foot (1544) with a tissue pad toward ultrasonic blade (1566). Another tine (1546) is configured to arc toward and meet with ultrasonic blade (1566) at a node or acoustically isolated feature, such that tine (1546) and the acoustic assembly form an integrated unit. As can best be seen in FIG. 48B, one tine (1542) may be configured to be selectively removed from housing (1520). Forceps (1510) additionally comprises a button (1521) which may be used to selectively switch between operational states described above. Of course, other examples of forceps (1510) incorporating elements of the various examples described above will be apparent to those of ordinary skill in the art in view of the teachings herein.

FIGS. 49 through 54 show an exemplary alternative set of tines (1640). Tines (1640) are substantially the same as tines (42, 46) having similar elements and functionality with certain exceptions noted below. Tines (1640) are shown as having a passive tine (1642) and an active tine (1646). Unlike passive tine (42), the distal end (1643) of passive tine (1642) is configured to selectively rotate about the longitudinal axis of passive tine (1642) such that differing tissue pads (1645, 1645) may face active tine (1646). In particular, distal end (1643) of passive tine (42) includes a substantially flat tissue pad (1645) and a substantially triangular tissue pad (1647) in this example. Triangular tissue pad (1647) includes a relatively narrow contact flat (1650). Flat tissue pad (1645) has a cross-sectional height that is greater than the diameter of ultrasonic blade (1649); while contact flat (1650) has a cross-sectional height that is less than the diameter of ultrasonic blade (1649). In some versions, the cross-sectional height of contact flat (1650) is approximately the diameter of ultrasonic blade (1649).

Figure 50B:
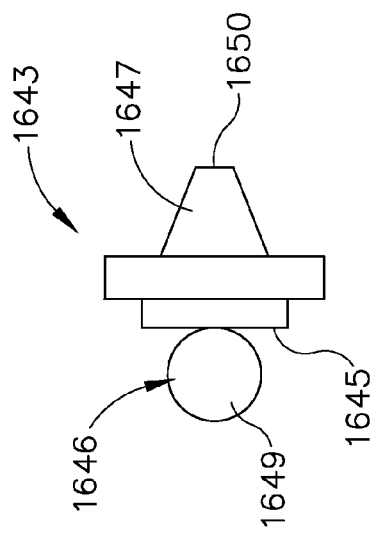
FIG. 50B depicts an end view of the tines of FIG. 50A, with the tines depressed.
Figure 50A:
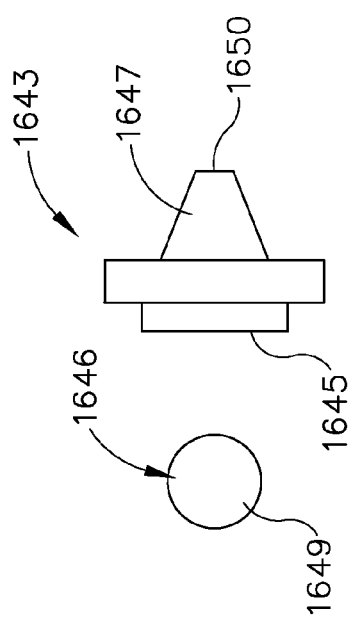
FIG. 50A depicts an end view of the tines of FIG. 49, with a broad side of a passive tine rotated toward an active tine.
Figure 50D:
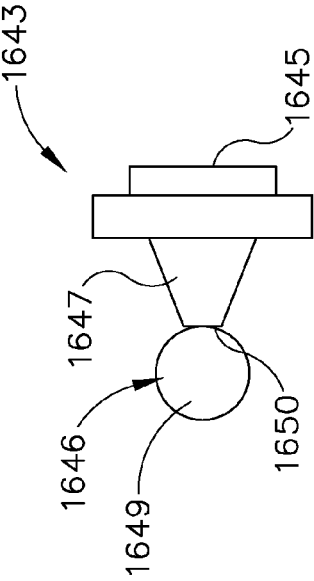
FIG. 50D depicts an end view of the tines of FIG. 50C, with the tines depressed.
Figure 50C:
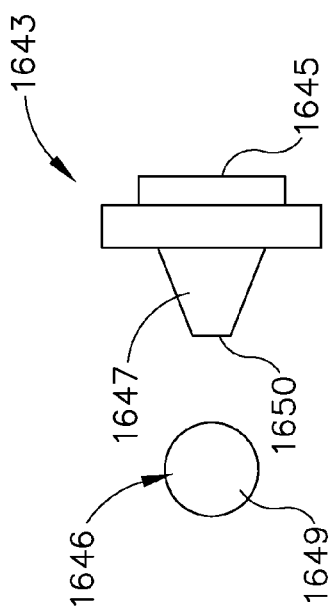
FIG. 50C depicts an end view of the tines of FIG. 49, with a cutting side of the passive tine rotated toward the active tine.

In FIGS. 50A-50B, distal end (1643) of passive tine (1646) is oriented such that flat tissue pad (1645) faces the ultrasonic blade (1649) of active tine (1646). In FIG. 50A, passive tine (1642) is spaced from active tine (1646) such that tissue may be received in a gap between flat tissue pad (1645) and ultrasonic blade (1649) of active tine (1646). In FIG. 50B, passive tine (1642) is driven toward active tine (1646), which would result in compression of tissue between flat tissue pad (1645) and ultrasonic blade (1649) of active tine (1646). In some instances, this may provide sealing of the tissue and/or relatively slow cutting of the tissue. In FIGS. 50C-50D, distal end (1643) of passive tine (1646) is oriented such that triangular tissue pad (1647) faces ultrasonic blade (1649) of active tine (1646). In FIG. 50C, passive tine (1642) is spaced from active tine (1646) such that tissue may be received in a gap between triangular tissue pad (1647) and ultrasonic blade (1649) of active tine (1646). In FIG. 50D, passive tine (1642) is driven toward active tine (1646), which would result in compression of tissue between triangular tissue pad (1647) and ultrasonic blade (1649) of active tine (1646). In some instances, this may provide relatively fast cutting of the tissue. The smaller surface area of contact flat (1650), as compared to the surface area of flat tissue pad (1645), may provide higher compression of tissue than flat tissue pad (1645). It should also be understood that triangular tissue pad (1647) may provide mechanical cutting of tissue without ultrasonic blade (1649) of active tine (1646) being ultrasonically activated.

Figure 52:
FIG. 52 depicts a perspective view of an exemplary alternative pad of the ultrasonic forceps of FIG. 1, having a hexagonal shape.
Figure 54:
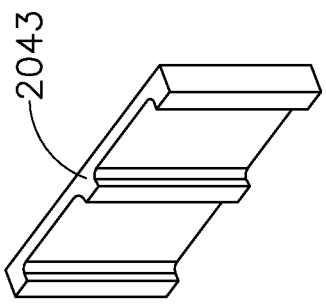
FIG. 54 depicts a perspective view of an exemplary alternative pad of the ultrasonic forceps of FIG. 1, having a plurality of grasping members.
Figure 51:
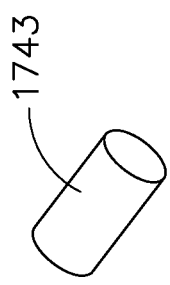
FIG. 51 depicts a perspective view of an exemplary alternative pad of the ultrasonic forceps of FIG. 1, having a cylindrical shape.
Figure 53:
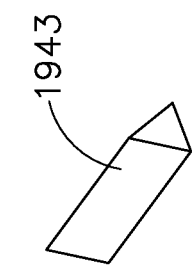
FIG. 53 depicts a perspective view of an exemplary alternative pad of the ultrasonic forceps of FIG. 1, having a triangular shape.

FIGS. 51 through 54 show varying alternative exemplary end geometries (1743, 1843, 1943, 2043) which may be used in addition to and/or in lieu of the geometries of tissue pads (1645, 1647) described above. In particular, FIG. 51 shows an end geometry (1743) having a circular cross-sectional profile. FIG. 52 shows an end geometry (1843) having an octagonal cross-sectional profile. FIG. 53 shows an end geometry (1943) having a triangular cross-sectional profile. FIG. 54 shows an end geometry (2043) having a series of flats separated by a series of ridges. It should be understood that any of these end geometries (1743, 1843, 1943, 2043) may be incorporated into one or more tissue pads at the distal end of passive tine (1642). It should also be understood that end geometries (1743, 1843, 1943, 2043) need not necessarily be provided on passive tine (1642). Indeed, active tine (1646) may also be equipped with any of the end geometries (1645, 1647, 1843, 1943, 2043) described above. It should also be understood that the end geometry of a passive tine (1642) may vary along the length of passive tine (1642), such that one tissue contacting area of passive tine (1642) may have one geometry, while another tissue contacting area of passive tine (1642) may have another geometry. Various suitable configurations and permutations will be apparent to those of ordinary skill in the art in view of the teachings herein.

FIG. 55 shows exemplary alternative tines (2140) having an active tine (2146) with a distal end (2143) that is rotatable about the longitudinal axis of active tine (2146). This rotatability may provide selective variability in the geometries that are exposed to a tissue pad (2141) of passive tine (2142). In other words, an operator may select a particular geometric configuration to engage tissue between distal end (2143) and tissue pad (2141). It should be understood that active tine (2146) may also incorporate any of the alternative end geometries (1643, 1743, 1843, 1943, 2043) discussed above. Other configurations of tines (1640, 2140) incorporating elements of the various examples described above will be apparent to those of ordinary skill in the art in view of the teachings herein.

In some instances, an instrument provides a combination of features of forceps (1310) with features of tine (1642) and/or features of tine (2146). For instance, one exemplary instrument may provide an orbital motion of a passive tine about the longitudinal axis of blade (1366), in combination with rotatability of the distal end (1643) of a passive tine (1642) about the longitudinal axis of passive tine (1642). This may provide even further variations in the combinations of geometries between which tissue may be compressed, particularly when both blade (1366) and distal end (1643) each have asymmetric cross-sectional profiles. As another merely illustrative example, an instrument may provide an orbital motion of a passive tine about the longitudinal axis of blade (1366), in combination with rotatability of the distal end (2143) of an active tine (2146) about the longitudinal axis of active tine (2146). As yet another merely illustrative example, an instrument may provide a combination of rotatability of the distal end (1643) of a passive tine (1642) about the longitudinal axis of passive tine (1642) with rotatability of the distal end (2143) of an active tine (2146) about the longitudinal axis of active tine (2146). Other suitable combinations will be apparent to those of ordinary skill in the art in view of the teachings herein.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a housing;
   (b) an acoustic assembly supported by the housing, wherein the acoustic assembly comprises:
      (i) a transducer, wherein the transducer extends along a transducer axis and is operable to generate ultrasonic vibrations,
      (ii) a waveguide acoustically coupled with the transducer and extending distally from the transducer, and
      (iii) an ultrasonic blade extending from a distal end of the waveguide, wherein the ultrasonic blade is configured to vibrate in response to ultrasonic vibrations communicated through the waveguide from the transducer;
   (c) a first tine secured relative to the housing, wherein the first tine extends distally along the acoustic assembly and includes a distal end configured to move toward the ultrasonic blade to directly contact and grasp tissue therebetween in response to movement of the first tine relative to the acoustic assembly; and
   (d) a second tine secured relative to the housing, wherein the second tine extends distally along the acoustic assembly, wherein the first and second tines define a distally extending tine gap therebetween,
   wherein the housing is configured to support the transducer relative to the first and second tines such that the transducer axis is laterally offset from the tine gap.

2. The surgical instrument of claim 1, wherein proximal portions of the first and second tines extend distally along a tine plane, wherein the transducer axis is offset from the tine plane.

3. The surgical instrument of claim 1, wherein a distal end of the second tine is configured to couple with a portion of the acoustic assembly containing the waveguide.

4. The surgical instrument of claim 1, wherein the housing is coupled to at least one of the first tine or the second tine.

5. The surgical instrument of claim 4, wherein the housing is coupled to the first tine and the second tine.

6. The surgical instrument of claim 1, wherein the housing comprises:
   (i) a first tine coupling feature configured to couple with a proximal portion of the first tine,
   (ii) a second tine coupling feature configured to couple with a proximal portion of the second tine, and
   (iii) a transducer receiving portion configured to receive and support the transducer, wherein the transducer receiving portion defines a central axis configured to align with the transducer axis.

7. The surgical instrument of claim 6, wherein at least one of the first or second tine coupling features comprises a groove, wherein the groove is configured to receive the proximal portion of the respective tine.

8. The surgical instrument of claim 1, wherein the waveguide includes at least one bend at a location proximally of the ultrasonic blade.

9. The surgical instrument of claim 8, wherein the first tine includes a bend that corresponds to the bend of the waveguide.

10. The surgical instrument of claim 9, further comprising a sheath configured to cover the waveguide, wherein the sheath is configured to assume a non-linear configuration to accommodate the bend of the waveguide.

11. The surgical instrument of claim 10, wherein the sheath includes a plurality of slots configured to promote flexing of the sheath.

12. The surgical instrument of claim 10, wherein the sheath includes a rigid proximal portion, a rigid distal portion, and a flexible medial portion configured to align with the bend of the waveguide.

13. The surgical instrument of claim 12, wherein the flexible medial portion includes at least one slot configured to promote flexing of the flexible medial portion.

14. The surgical instrument of claim 1, wherein the first tine includes a first gripping feature and the second tine includes a second gripping feature, wherein the transducer is arranged proximally of each of the first and second gripping features.

15. The surgical instrument of claim 1, wherein one of the first tine or the second tine includes a guide post and the other of the first tine or the second tine includes an opening configured to receive the guidepost when the first tine is moved toward the second tine to thereby promote alignment of the first tine with the second tine.

16. A surgical instrument comprising:
   (a) a housing;
   (b) an acoustic assembly supported by the housing, wherein the acoustic assembly comprises:
      (i) a transducer operable to generate ultrasonic vibrations,
      (ii) an ultrasonic blade configured to be driven by the transducer with ultrasonic vibrations, and
      (iii) a waveguide acoustically coupling the transducer with the ultrasonic blade, wherein the waveguide includes a proximal end coupled with the transducer, a distal end coupled with the ultrasonic blade, and a medial portion extending therebetween, wherein the medial portion is bent relative to a longitudinal axis of the transducer; and (c) a tine secured relative to the housing, wherein the tine extends distally along the acoustic assembly and includes a distal end configured to move toward the ultrasonic blade in response to movement of the tine relative to the acoustic assembly.

17. The surgical instrument of claim 16, wherein the tine defines a first tine having a first gripping feature, wherein the acoustic assembly defines a second tine having a second gripping feature.

18. The surgical instrument of claim 16, wherein the medial portion of the waveguide includes first and second bends.

19. The surgical instrument of claim 16, wherein the acoustic assembly further comprises a waveguide sheath configured to cover the waveguide, wherein the waveguide sheath is configured to assume a non-linear configuration to accommodate the bent medial portion of the waveguide.

20. A surgical instrument comprising:
(a) a first tine having a proximal end, a distal end, and a first gripping feature arranged therebetween;
(b) a second tine having a proximal end, a distal end, and a second gripping feature arranged therebetween, wherein the first and second tines are coupled with one another at the proximal ends, wherein the first and second tines are spaced apart from one another at the distal ends, wherein the first tine is movable toward the second tine for engaging tissue with at least the distal end of the first tine; and
(c) at least one piezoelectric element provided on a surface of the first tine between the distal end thereof and the gripping feature, wherein the piezoelectric element is configured to drive the distal end of the first tine with ultrasonic vibrations.

* * * * *